(12) United States Patent
Souda et al.

(10) Patent No.: US 9,463,151 B2
(45) Date of Patent: Oct. 11, 2016

(54) COSMETIC CONTAINING LIQUID ORGANOPOLYSILOXANE

(75) Inventors: Tatsuo Souda, Ichihara (JP); Seiki Tamura, Ichihara (JP); Naoki Suzuki, Sunto-gun (JP); Haruhiko Furukawa, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 202 days.

(21) Appl. No.: 13/997,777

(22) PCT Filed: Dec. 26, 2011

(86) PCT No.: PCT/JP2011/080570
§ 371 (c)(1),
(2), (4) Date: Sep. 24, 2013

(87) PCT Pub. No.: WO2012/091155
PCT Pub. Date: Jul. 5, 2012

(65) Prior Publication Data
US 2014/0004065 A1  Jan. 2, 2014

(30) Foreign Application Priority Data
Dec. 27, 2010  (JP) .................................. 2010-289722

(51) Int. Cl.
| | | |
|---|---|---|
| *A61K 8/89* | (2006.01) | |
| *A61K 8/895* | (2006.01) | |
| *A61K 8/92* | (2006.01) | |
| *A61Q 1/02* | (2006.01) | |
| *A61Q 1/12* | (2006.01) | |
| *A61Q 19/00* | (2006.01) | |
| *C08G 77/20* | (2006.01) | |
| *C08G 77/50* | (2006.01) | |
| *C08L 83/14* | (2006.01) | |
| *A61Q 15/00* | (2006.01) | |
| *A61Q 17/04* | (2006.01) | |
| *A61Q 5/00* | (2006.01) | |
| *A61Q 5/12* | (2006.01) | |

(52) U.S. Cl.
CPC ................ *A61K 8/89* (2013.01); *A61K 8/895* (2013.01); *A61K 8/92* (2013.01); *A61Q 1/02* (2013.01); *A61Q 1/12* (2013.01); *A61Q 5/00* (2013.01); *A61Q 15/00* (2013.01); *A61Q 17/04* (2013.01); *A61Q 19/00* (2013.01); *C08G 77/20* (2013.01); *C08G 77/50* (2013.01); *C08L 83/14* (2013.01); *A61K 2800/10* (2013.01); *A61Q 5/12* (2013.01)

(58) Field of Classification Search
CPC ...... A61K 8/891; A61K 8/894; A61K 8/898; A61K 2800/412; A61K 8/02; A61K 8/042; A61K 8/06; A61K 8/064; A61K 8/375; A61K 8/585; A61K 8/895; A61Q 19/00; A61Q 1/02; A61Q 1/10; A61Q 5/12
See application file for complete search history.

(56) References Cited

U.S. PATENT DOCUMENTS

| | | | |
|---|---|---|---|
| 4,980,167 A | 12/1990 | Harashima et al. | |
| 5,412,004 A * | 5/1995 | Tachibana et al. | ............. 524/27 |
| 5,628,989 A | 5/1997 | Harashima et al. | |
| 5,817,302 A | 10/1998 | Berthiaume et al. | |
| 5,939,478 A | 8/1999 | Beck et al. | |
| 5,981,680 A | 11/1999 | Petroff et al. | |
| 7,723,443 B1 | 5/2010 | O'Lenick et al. | |

FOREIGN PATENT DOCUMENTS

| | | |
|---|---|---|
| EP | 2014701 A2 | 1/2009 |
| JP | H02243612 A | 9/1990 |
| JP | H0812524 A | 1/1996 |
| JP | H0812545 A | 1/1996 |
| JP | H0812546 A | 1/1996 |
| JP | H 08-319351 A | 12/1996 |
| JP | H09241511 A | 9/1997 |
| JP | H1036219 A | 2/1998 |
| JP | H11193331 A | 7/1999 |
| JP | 2000038450 A | 2/2000 |
| JP | 2000281523 A | 10/2000 |
| JP | 2001512164 A | 8/2001 |
| JP | 2007532754 A | 11/2007 |
| JP | 2009185296 A | 8/2009 |
| JP | 2010502780 A | 1/2010 |
| WO | WO 99/06473 A1 | 2/1999 |
| WO | WO 2005/100444 A1 | 10/2005 |
| WO | WO 2008/027497 A2 | 3/2008 |

OTHER PUBLICATIONS

English language abstract for JP H02243612 extracted from espacenet.com database on Jan. 30, 2014, 2 pages. Also, see English language equivalent U.S. Pat. No. 4,980,167.
English language machine translation and abstract for JP H0812524 extracted from espacenet.com database on Jan. 30, 2014, 17 pages.
English language abstract for JP H0812545 extracted from espacenet.com database on Jan. 30, 2014, 1 pages. Also, see English language equivalent U.S. Pat. No. 5,628,989.
English language abstract for JP H0812526 extracted from espacenet.com database on Jan. 30, 2014, 1 page. Machine translation extracted from JPO on 9 pages.

(Continued)

*Primary Examiner* — Audrea Buckley
(74) *Attorney, Agent, or Firm* — Howard & Howard Attorneys PLLC

(57) ABSTRACT

The present invention provides a cosmetic exhibiting superior feeling to the touch and a superior uniformity using a novel organopolysiloxane. The cosmetic contains a liquid organopolysiloxane having fluidity at 25° C. and having a crosslinked three-dimensional network structure. The aforementioned liquid organopolysiloxane has a loss factor, tan δ, at a shear frequency of 10 Hz, which is 1 or more.

19 Claims, 3 Drawing Sheets

(56) References Cited

OTHER PUBLICATIONS

English language abstract for JP H09241511 extracted from espacenet.com database on Jan. 30, 2014, 1 pages. Machine translation extracted from JPO on 9 pages.
English language abstract for JP H1036219 extracted from espacenet.com database on Jan. 30, 2014, 1 pages. Machine translation extracted from JPO on 13 pages.
English language abstract for JP H11193331 extracted from espacenet.com database on Jan. 30, 2014, 2 pages. Also see English language equivalent U.S. Pat. No. 5,939,478.
English language abstract for JP2000038450 extracted from espacenet.com database on Jan. 30, 2014, 2 pages. Also see English language equivalent U.S. Pat. No. 5,981,680.
English language abstract for JP2000281523 extracted from espacenet.com database on Jan. 30, 2014, 2 pages. Machine translation extracted from JPO on 33 pages.
English language abstract for JP2001512164 extracted from espacenet.com database on Jan. 30, 2014, 2 pages. Also see English language equivalent WO 99/06473.
English language abstract for JP2007532754 extracted from espacenet.com database on Jan. 30, 2014, 1 pages. Also see English language equivalent WO2005/100444.
English language abstract for JP2009185296 extracted from espacenet.com database on Jan. 30, 2014, 2 pages. Machine translation extracted from JPO on 73 pages.
English language abstract for JP20105027804 extracted from espacenet.com database on Jan. 30, 2014, 1 pages. Also see English language equivalent WO2008/027497.
PCT International Search Report for PCT/JP2011/080570, dated Feb. 28, 2012, 3 pages.
English language abstract for JPH 08-319351 extracted from espacenet.com database on Sep. 24, 2015, 2 pages.
English language abstract and translation for JP 2009185296 extracted from PAJ database, 136 pages, published Aug. 20, 2009.
English language abstract for JP 2010502780 extracted from espacenet.com database on Jan. 30, 2014, 18 pages. Also see English language equivalent WO 2008/027497.
English language abstract for JP H0812546 extracted from espacenet.com database on Jan. 30, 2014, 16 pages. Machine translation extracted from JPO on 9 pages.

\* cited by examiner

000
COSMETIC CONTAINING LIQUID ORGANOPOLYSILOXANE

TECHNICAL FIELD

The present invention relates to a cosmetic containing a liquid organopolysiloxane having a microcrosslinking structure.

This application is the National Stage of International Patent Application No. PCT/JP2011/080570, filed on Dec. 26, 2011, which claims priority to and all the advantages of Japanese Patent Application No. 2010-289722, filed on Dec. 27, 2010, the content of which is incorporated herein by reference.

BACKGROUND ART

Heretofore, various silicones such as a silicone oil with a low viscosity, a silicone gum with a high degree of polymerization, and the like have been blended in a cosmetic as a cosmetic raw material. The silicone elastomer particles obtained by crosslinking a crosslinkable organopolysiloxane have also been used as a cosmetic raw material.

The silicone elastomer particles can be obtained by, for example, dispersing an uncrosslinked crosslinkable organopolysiloxane in water, heating the dispersion to carry out crosslinking, and then drying. However, in the preparation of the silicone elastomer particles in accordance with the aforementioned method, a drying step for removing water is necessary, and the preparation process is complicated.

Therefore, blending the silicone elastomer particles in the state of an aqueous dispersion in which the particles are dispersed in water in a cosmetic has also been proposed. However, in the aqueous dispersion of the silicone elastomer particles, an emulsifier used in order to disperse the uncrosslinked crosslinkable organopolysiloxane in water is usually present. If the aqueous dispersion in which the emulsifier remains is blended in a cosmetic, feeling to the touch of the cosmetic may be impaired, depending on the types of the emulsifiers.

On the other hand, an oil-based dispersion in which silicone elastomer particles are dispersed in an oil such as a silicone oil or the like has been known as a cosmetic raw material. The aforementioned oil-based dispersion can be produced by crosslinking an organopolysiloxane in an oil. However, as long as the aforementioned oil-based dispersion contains the silicone elastomer with an increased elastic force in the form of solid particles, a cosmetic blending the aforementioned oil-based dispersion exhibits a poor smooth sensation, and poor compatibility with the skin. In addition, the aforementioned oil-based dispersion is a non-uniform system in which the particles are dispersed in the oil, and for this reason, even if the dispersion is mixed with other oil agents, particles may remain. Therefore, a uniform oil phase cannot be obtained.

In addition, a paste or a gel obtained by absorbing an oil such as a silicone oil or the like in a silicone elastomer has also been known as a cosmetic raw material. For example, Japanese Unexamined Patent Application, First Publication No. 2009-185296 describes a paste in which an organopolysiloxane having a specific crosslinking structure contains an oil and swells. However, the paste or gel is not a liquid, and for this reason, it is difficult to uniformly mix with a liquid oil that is used in a cosmetic in many cases. Therefore, if the aforementioned paste or gel is blended in a cosmetic, the paste or gel may remain in the form of particles in the oil phase. In this case, the same problem as that described in the case of the aforementioned oil-based dispersion containing the silicone elastomer in the form of solid particles may occur.

On the other hand, Published Japanese Translation No. 2010-502780 of the PCT International Application discloses a branched polysiloxane, but fails to describe use thereof in a cosmetic.

DISCLOSURE OF INVENTION

Technical Problems

The present invention has been made in view of the circumstances of the aforementioned prior art. An objective of the present invention is to provide a cosmetic exhibiting superior feeling to the touch and superior uniformity using a novel organopolysiloxane useful as a cosmetic raw material.

Technical Solution

As a result of diligent studies in order to achieve the aforementioned objective, the inventors of the present invention have completed the present invention. The objective of the present invention can be achieved by blending a liquid organopolysiloxane having fluidity at 25° C. and having a crosslinked three-dimensional network structure in a cosmetic.

It is preferable that the aforementioned liquid organopolysiloxane have a loss factor, tan δ, at a shear frequency of 10 Hz, which is 1 or more.

The aforementioned liquid organopolysiloxane can be obtained by at least reacting
(a) at least one organopolysiloxane and/or at least one unsaturated aliphatic hydrocarbon, having more than one unsaturated bond on average per molecule,
(b) at least one organohydrogenpolysiloxane having more than one silicon atom-binding hydrogen atom on average per molecule, and
(c) a catalyst for a hydrosilylation reaction. It is preferable that at least one of the aforementioned components (a) and (b) contain, as a part of the component, at least three functional groups per molecule.

The aforementioned liquid organopolysiloxane preferably has a crosslinked three-dimensional network structure, represented by the following average composition formula (1):

$$M_a D_b D^{Link}_c T_d T^{Link}_e Q_f \qquad (1)$$

wherein
M represents an $R_3SiO_{1/2}$ unit;
D represents an $R_2SiO_{2/2}$ unit;
T represents an $RSiO_{3/2}$ unit;
Q represents a $SiO_{4/2}$ unit;
$D^{Link}$ represents an $RASiO_{2/2}$ unit;
$T^{Link}$ represents an $ASiO_{3/2}$ unit;
R represents an organic group selected from a substituted or non-substituted, and linear or branched monovalent hydrocarbon group having 1 to 30 carbon atoms, and a group represented by —$C_jH_{2j}O(C_kH_{2k}O)_mR'$ group, wherein j is an integer ranging from 2 to 20, k is an integer ranging from 2 to 4, m is an integer ranging from 2 to 100, and R' is a hydrogen atom, a substituted or non-substituted, and linear or branched monovalent hydrocarbon group having 1 to 30 carbon atoms, or an acetyl group;
A is a divalent linking group having a group represented by the following formula (2), (3), (4) or (5):

$$-(CH_2)_n-SiR''_2O-(SiR''_2O)_p-SiR''_2-(CH_2)_n- \quad (2)$$

$$-C_sH_{2s}O-(C_tH_{2t}O)_u-C_sH_{2s}- \quad (3)$$

$$-C_vH_{2v}- \quad (4)$$

$$-SiR''_2O-(SiR''_2O)_p-SiR''_2- \quad (5)$$

wherein each R" independently represents a substituted or non-substituted, and linear or branched monovalent hydrocarbon group having 1 to 30 carbon atoms, and having no aliphatic unsaturation group; n is an integer ranging from 2 to 20; p is an integer ranging from 0 to 500; u is an integer ranging from 2 to 100; s is an integer ranging from 2 to 20; t is an integer ranging from 2 to 4; and v is an integer ranging from 2 to 20, $a \geq 0$, $b \geq 0$, $c \geq 0$, $d \geq 0$, $e \geq 0$, and $f \geq 0$, with the proviso that $a+b+c+d+e+f=1$, and $c+e$ ranges from 0.001 to 0.6.

The cosmetic of the present invention can comprise, in addition to the aforementioned, (A) liquid organopolysiloxane, (B) at least one oil agent which is liquid at 25° C.

The aforementioned cosmetic preferably comprises a uniform oil phase, and/or preferably substantially comprises no gel particles in the oil phase.

The aforementioned (B) oil agent is preferably one having compatibility with the aforementioned (A) liquid organopolysiloxane, and is more preferably a silicone oil.

The cosmetic of the present invention preferably further comprises (C) at least one oil agent other than the aforementioned (B) oil agent.

The cosmetic of the present invention preferably further comprises (D) at least one surfactant.

The cosmetic of the present invention preferably further comprises (E) at least one alcohol.

The cosmetic of the present invention preferably further comprises (F1) at least one thickening agent and/or (F2) at least one gelling agent.

The cosmetic of the present invention preferably further comprises (G1) at least one powder and/or (G2) at least one coloring agent.

The cosmetic of the present invention preferably further comprises (H) at least one UV-protective component.

The cosmetic of the present invention preferably further comprises (I) water.

The cosmetic of the present invention is suitably used in a skin care product, a hair product, an antiperspirant product, a deodorant product, a makeup product, or a UV-protective product.

Advantageous Effects of Invention

The organopolysiloxanes used in the present invention maintain the liquid form, while a film-forming sensation and an elastic sensation are provided. For this reason, they can be used as a cosmetic raw material which can exhibit distinct elastomeric feeling to the touch which is clearly different from the conventional silicone oils with a low viscosity, silicone gums with a high degree of polymerization, or silicone elastomers in the form of solid particles. In addition, at the time of producing the aforementioned organopolysiloxane, use of an emulsifier is not necessary. Therefore, complication of the production steps can be prevented, and use of the organopolysiloxanes is advantageous in view of production cost.

In addition, the cosmetic of the present invention comprises the aforementioned liquid organopolysiloxane, and for this reason, not only cosmetic properties such as water resistance, makeup durability and the like are superior, but also a superior sensation during use such as a smoothing sensation, compatibility with the skin or the like is also exhibited.

In addition, in the case in which the cosmetic of the present invention comprises a liquid oil agent together with the aforementioned liquid organopolysiloxane, superior feeling to the touch, and in particular, a superior smoothing sensation or a superior compatibility with the skin is exhibited, and a uniform condition in which a uniform oil phase is contained and/or particles such as gel particles are not substantially contained in the oil phase can be obtained.

BEST MODES FOR CARRYING OUT THE INVENTION

Figure 1:
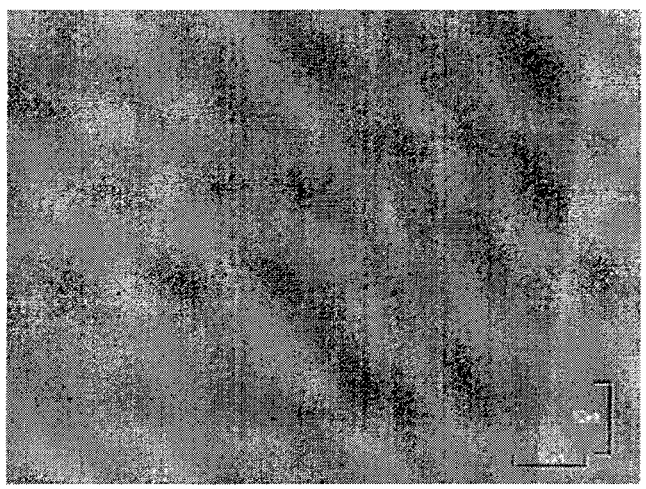
FIG. 1 shows an electron microscope photograph of a mixture of Silicone Compound No. 1 and decamethylpentacyclosiloxane (D5) (mixing ratio=2:8 (D5)).

The organopolysiloxane used in the present invention is a liquid product having fluidity at 25° C. "Having fluidity at 25° C." in the present invention means that when a liquid level of an organopolysiloxane in a specified contained is horizontal, if the container is inclined, the aforementioned liquid level moves or deforms, and preferably can be again horizontal, after 96 hours, preferably after 48 hours, and more preferably after 24 hours. Here, "being horizontal" means a level intersecting at a right angle with respect to the direction of gravitational force.

In addition, the aforementioned organopolysiloxane has a crosslinked three-dimensional network structure, with the proviso that the aforementioned organopolysiloxane has a low degree-crosslinked or micro-crosslinked molecular structure in which polysiloxane chains are loosely crosslinked in the form of a three-dimensional network. Therefore, the aforementioned organopolysiloxane is liquid such that fluidity is exhibited at room temperature.

The aforementioned organopolysiloxane preferably has a loss factor, tan δ, at a shear frequency of 10 Hz, which is 1 or more. The loss factor is a ratio (G"/G') of a storage shear elastic modulus (G') and a loss shear elastic modulus (G"), and indicates how much an object to be measured absorbs energy when the object is deformed. The loss factor, tan δ, can be measured by means of a dynamic viscoelasticity measuring instrument. In general, as the value of tan δ is increased, an ability of absorbing the energy and then converting into heat or the like is increased, and therefore, repulsion is reduced.

The aforementioned organopolysiloxane having a loss factor, tan δ, at a shear frequency of 10 Hz which is 1 or more has reduced repulsion, and does not exhibit a function as an elastic body such as a common rubber. In view of molecular structure, this means that a degree of crosslinking of the aforementioned organopolysiloxane is considerably reduced, as compared to common silicone rubbers. On the other hand, with a non-crosslinking liquid such as water on which torque is not exerted, a loss factor at a shear frequency of 10 Hz cannot be measured.

The aforementioned organopolysiloxane can be obtained by at least reacting
(a) at least one organopolysiloxane and/or at least one unsaturated aliphatic hydrocarbon, having more than one unsaturated bond on average per molecule,
(b) at least one organohydrogenpolysiloxane having more than one silicon atom-binding hydrogen atom on average per molecule, and
(c) a catalyst for a hydrosilylation reaction. It is preferable that at least one of the aforementioned components (a) and (b) contain, as a part of the component, at least three functional groups per molecule.

The structure of the aforementioned (a) at least one organopolysiloxane and/or at least one unsaturated aliphatic hydrocarbon, having more than one unsaturated bond on average per molecule, is not particularly restricted, as long as the compound has one or more, preferably 1.01 to 100, more preferably 1.1 to 50, further more preferably 1.2 to 25, and in particular, preferably 1.3 to 10 unsaturated bonds on average per molecule. Linear, branched or reticulated organopolysiloxanes and/or unsaturated aliphatic hydrocarbons can be used. The positions of the unsaturated bonds on the organopolysiloxane or the unsaturated aliphatic hydrocarbon are not restricted, and the unsaturated bonds may be present on the main chain or at the terminal. In view of a reduction of the degree of crosslinking, the unsaturated bonds are preferably present at the terminal.

The unsaturated bond is preferably present in the unsaturated aliphatic hydrocarbon group. The unsaturated aliphatic hydrocarbon group preferably has 2 to 30 carbon atoms, and more preferably has 2 to 20 carbon atoms. As examples of the monovalent unsaturated aliphatic hydrocarbon group having 2 to 30 carbon atoms, mention may be made of linear or branched alkenyl groups such as a vinyl group, a 1-propenyl group, an allyl group, an isopropenyl group, a 1-butenyl group, a 2-butenyl group, a pentenyl group, a hexenyl group, and the like; cycloalkenyl groups such as a cyclopentenyl group, a cyclohexenyl group and the like; cycloalkenylalkyl groups such as a cyclopentenylethyl group, a cyclohexenylethyl group, a cyclohexenylpropyl group and the like; and alkynyl groups such as an ethynyl group, a propargyl group and the like. An alkenyl group is preferable, and a vinyl group and a hexenyl group are, in particular, preferable.

In the case in which the aforementioned component (a) is the organopolysiloxane, the unsaturated aliphatic hydrocarbon group containing an unsaturated bond preferably binds to a silicon atom. In addition, in the case in which the aforementioned component (a) is the organopolysiloxane, the group binding to the silicon atom, other than the unsaturated aliphatic hydrocarbon, can be a substituted or non-substituted monovalent hydrocarbon group or monovalent organic group having a reactive functional group.

The substituted or non-substituted monovalent hydrocarbon group is typically a substituted or non-substituted monovalent saturated hydrocarbon group having 1 to 30 carbon atoms, preferably 1 to 10 carbon atoms, and more preferably 1 to 4 carbon atoms, or a monovalent aromatic hydrocarbon group having 6 to 30 carbon atoms and more preferably 6 to 12 carbon atoms. The aforementioned component (a) may have a hydroxyl group, or an alkoxy group having 1 to 12 carbon atoms such as a methoxy group, an ethoxy group, a propoxy group, a butoxy group, or the like, as the monovalent organic group.

As examples of monovalent saturated hydrocarbon groups having 1 to 30 carbon atoms, mention may be made of, for example, linear or branched alkyl groups such as a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, and the like; and cycloalkyl groups such as a cyclopentyl group, a cyclohexyl group, a cycloheptyl group, a cyclooctyl group, and the like.

As examples of monovalent aromatic hydrocarbon groups having 6 to 30 carbon atoms, mention may be made of, for example, aryl groups such as a phenyl group, a tolyl group, a xylyl group, a mesityl group and the like. A phenyl group is preferable. The aromatic hydrocarbon groups in the specification of the present application encompass groups in which aromatic hydrocarbons and aliphatic saturated hydrocarbons are combined, other than groups consisting of aromatic hydrocarbons. As examples of the groups in which aromatic hydrocarbons and saturated hydrocarbons are combined, mention may be made of, for example, aralkyl groups such as a benzyl group, a phenethyl group and the like.

The hydrogen atoms on the aforementioned monovalent hydrocarbon may be substituted with one or more substituents. The aforementioned substituents may be selected from the group consisting of halogen atoms such as a fluorine atom, a chlorine atom, a bromine atom, and an iodine atom, a hydroxyl group, an amide group, an ester group, a carboxyl group, and an isocyanate group. A monovalent saturated or aromatic hydrocarbon group having at least one substituent described above is preferable. In particular, as examples thereof, mention may be made of, for example, a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatepropyl group and the like.

As examples of monovalent organic groups having reactive functional groups, mention may be made of, for example, a monovalent saturated or aromatic hydrocarbon group having a reactive functional group selected from the group consisting of a hydroxyl group, a mercapto group, an epoxy group, an amino group, an amide group, an ester group, a carboxyl group, and an isocyanate group. The number of the reactive functional groups present on the monovalent organic group may be one or plural. Preferably, the monovalent organic group is a monovalent saturated or aromatic hydrocarbon group having at least one reactive functional group described above. As examples of reactive functional groups, mention may be made of, for example, a 3-hydroxypropyl group, a 3-(2-hydroxyethoxy)propyl group, a 3-mercaptopropyl group, a 2,3-epoxypropyl group, 3,4-epoxybutyl group, a 4,5-epoxypentyl group, a 2-glycidoxyethyl group, a 3-glycidoxypropyl group, a 4-glycidoxybutyl group, a 2-(3,4-epoxycyclohexyl)ethyl group, a 3-(3,4-epoxycyclohexyl)propyl group, an aminopropyl group, a N-methylaminopropyl group, a N-butylaminopropyl group, a N,N-dibutylaminopropyl group, a 3-(2-aminoethoxy)propyl group, a 3-(2-aminoethylamino)propyl group, a 3-carboxypropyl group, a 10-carboxydecyl group, a 3-isocyanatepropyl group and the like.

As the aforementioned component (a), a linear or branched polysiloxane is preferable. As the linear component (a), polymers containing diorganosiloxane units and triorganosiloxy units are preferable. As examples thereof, mention may be made of, for example, a dimethylpolysiloxane in which both molecular terminals are capped with dimethylvinylsiloxy groups, a copolymer of methylphenylsiloxane and dimethylsiloxane in which both molecular terminals are capped with dimethylvinylsiloxy groups, a copolymer of methylvinylsiloxane and dimethylsiloxane in which both molecular terminals are capped with dimethylvinylsiloxy groups, a copolymer of methylvinylsiloxane and dimethylsiloxane in which both molecular terminals are capped with trimethylsiloxy groups, a copolymer of methylphenylsiloxane, methylvinylsiloxane and dimethylsiloxane in which both molecular terminals are capped with trimethylsiloxy groups, a copolymer of methylvinylsiloxane and dimethylsiloxane in which both molecular terminals are capped with silanol groups, polymers in which a part of methyl groups of the aforementioned polymers is replaced with an alkyl group other than a methyl group, such as an ethyl group, a propyl group or the like, or a halogenated alkyl group such as a 3,3,3-trifluoropropyl group or the like, and a mixture of two or more types of the aforementioned polymers. In particular, a linear diorganopolysiloxane having unsaturated aliphatic hydrocarbon groups, and in particular, alkenyl groups, only at both molecular terminals.

As the aforementioned branched component (a), in particular, polymers containing diorganosiloxane units, organosilsesquioxane units, and triorganosiloxy units are preferable. As the silicon atom-binding organic groups in the aforementioned units, monovalent hydrocarbon groups such as alkyl groups such as a methyl group, an ethyl group, a propyl group and the like; alkenyl groups such as a vinyl group, an allyl group, a butenyl group, a hexenyl group and the like; aryl groups such as a phenyl group, a tolyl group and the like; a halogenated alkyl groups such as a 3,3,3-trifluoropropyl group and the like; and the like are preferable. Although the organic groups may have a trace amount of a hydroxyl group, and an alkoxy group such as a methoxy group or the like, at least two silicon atom-binding organic groups in the aforementioned polymer must be an unsaturated aliphatic hydrocarbon group, and in particular, an alkenyl group. In addition, the ratio of the aforementioned units is not particularly restricted. In the aforementioned polymer, it is preferable that the dioganosiloxane unit be in an amount ranging from 80.0% by mol to 99.65% by mol, the organosilsesquioxane unit be in an amount ranging from 0.10% by mol to 10.00% by mol, the triorganosiloxy unit be in an amount ranging from 0.10% by mol to 10.00% by mol, and the triorganosiloxy unit be in the remaining amount.

On the other hand, the aforementioned component (a) may be an unsaturated aliphatic hydrocarbon. As examples of unsaturated aliphatic hydrocarbons, mention may be made of, for example, various dienes, diynes, enynes and the like. In view of crosslinking, dienes, diynes, and enynes are preferable. The aforementioned dienes, diynes, and enynes are compounds having a structure in which at least two unsaturated bonds are separated by one or more, and preferably two or more single bonds in a molecule. The aforementioned unsaturated aliphatic hydrocarbon group may be present at the terminal of the molecular chain, or as a pendant group in the molecular chain.

As examples of unsaturated aliphatic hydrocarbons as the aforementioned component (a), mention may be made of, for example, α,ω-unsaturated alkene and alkyne having 2 to 30 carbon atoms. As examples thereof, mention may be made of, for example, 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, 1-hexen-5-yne, and the like.

The aforementioned component (a) can be used alone or together with two or more different types of organopolysiloxanes and/or unsaturated aliphatic hydrocarbons. Namely, the aforementioned component (a) may be a mixture of one or more types of organopolysiloxanes and one or more types of unsaturated aliphatic hydrocarbons. Therefore, "having more than one unsaturated bond on average" means having one or more unsaturated bond on average in the case of using two or more types of organopolysiloxanes and/or unsaturated aliphatic hydrocarbons.

The structure of the aforementioned (b) at least one organohydrogenpolysiloxane having more than one silicon atom-binding hydrogen atom on average per molecule, is not particularly restricted, as long as the compound has more than one, preferably 1.01 to 100, more preferably 1.1 to 50, further more preferably 1.2 to 25, and in particular, preferably 1.3 to 10 silicon atom-binding hydrogen atoms on average per molecule. Linear, branched or reticulated organopolysiloxanes can be used. The positions of the silicon atom-binding hydrogen atoms on the organopolysiloxane are not restricted, and the silicon atom-binding hydrogen atoms may be present on the main chain or at the terminal. In view of reduction of the degree of crosslinking, the silicon atom-binding hydrogen atoms are preferably present at the terminal.

As examples of the aforementioned component (b), mention may be made of, for example, 1,1,3,3-tetramethyldisiloxane, 1,3,5,7-tetramethylcyclotetrasiloxane, methylhydrogenpolysiloxane in which both molecular terminals are capped with trimethylsiloxy groups, a copolymer of methylhydrogensiloxane and dimethylsiloxane in which both molecular terminals are capped with trimethylsiloxy groups, dimethylsiloxane in which both molecular terminals are capped with dimethylhydrogensiloxy groups, dimethylpolysiloxane in which both molecular terminals are capped with dimethylhydrogensiloxy groups, a copolymer of methylhydrogensiloxane and dimethylsiloxane in which both molecular terminals are capped with dimethylhydrogensiloxy groups, a copolymer of diphenylsiloxane and methylhydrogensiloxane in which both molecular terminals are capped with trimethylsiloxy groups, a copolymer of dimethylsiloxane, diphenylsiloxane and methylhydrogensiloxane in which both molecular terminals are capped with trimethylsiloxy groups, a copolymer formed from $(CH_3)_2HSiO_{1/2}$ units and $SiO_{4/2}$ units, and a copolymer formed from $(CH_3)_2HSiO_{1/2}$ units, $SiO_{4/2}$ units and $(C_6H_5)SiO_{3/2}$ units.

It is preferable that at least one of the aforementioned components (a) and (b) contain molecules having at least three functional groups per molecule.

The aforementioned (c) hydrosilylation reaction catalyst is a catalyst for accelerating an addition reaction of the unsaturated bonds in the aforementioned component (a) and the silicon atom-binding hydrogen atoms in the aforementioned component (b). As examples of the aforementioned component (c), mention may be made of, for example, a platinum-based catalyst such as chloroplatinic acid, an alcohol solution of chloroplatinic acid, a complex of platinum and an olefin, a complex of platinum and 1,3-divinyl-1,1,3,3-tetramethyldisiloxane, powders on which platinum is carried, and the like; a palladium-based catalyst such as tetrakis (triphenylphosphine) palladium, palladium black, a mixture with triphenylphosphine and the like; and a rhodium-based catalyst. A platinum group metal-based catalyst such as a platinum-based catalyst, a palladium-based catalyst or the like is preferable. A platinum-based catalyst is more preferable.

The blending amount of the aforementioned component (c) is a catalytic amount. In the case of using a platinum-based catalyst as the aforementioned component (c), the practical amount of the platinum metal of the catalyst preferably ranges from 0.01 to 1,000 ppm in a weight (mass) unit with respect to the total weight (mass) of the aforementioned components (a) to (c). In particular, the amount preferably ranges from 0.1 to 500 ppm.

When the organopolysiloxane used in the present invention is produced, at least one (d) other component may be optionally reacted with the aforementioned component (a) and component (b). As examples of the aforementioned component (d), mention may be made of, for example, polyethers having unsaturated aliphatic hydrocarbon groups.

The aforementioned polyethers having unsaturated aliphatic hydrocarbon groups preferably have unsaturated hydrocarbon groups at the terminal of the molecular chain. For example, those represented by the following formula are preferable.

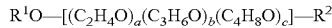
$$R^1O-[(C_2H_4O)_a(C_3H_6O)_b(C_4H_8O)_c]-R^2$$

wherein $R^1$ represents a monovalent unsaturated aliphatic hydrocarbon group having 2 to 30 carbon atoms; $R^2$ represents a hydrogen atom, an acyl group, or a monovalent saturated hydrocarbon group having 1 to 30 carbon atoms; a ranges from 0 to 100; b ranges from 0 to 100; c ranges from 0 to 100, with the proviso that 0<a+b+c.

Examples of the monovalent unsaturated aliphatic hydrocarbon group having 2 to 30 carbon atoms and examples of the monovalent saturated hydrocarbon group having 1 to 30 carbon atoms are the same as those described above. As described above, by reacting a component having an oxyalkylene group together with the aforementioned component (a) and component (b), compatibility with an aqueous component commonly used in a cosmetic such as water, a lower alcohol or the like can be imparted to the organopolysiloxane used in the present invention.

As examples of the aforementioned polyethers having unsaturated aliphatic hydrocarbon groups, mention may be made of, for example, $H_2C=CHCH_2O(C_2H_4O)_aH$, $H_2C=CHCH_2O(C_2H_4O)_aCH_3$, $H_2C=CHCH_2O(C_2H_4O)_aC(O)CH_3$, $H_2C=CHCH_2O(C_2H_4O)_a(C_3H_6O)_bH$, $H_2C=CHCH_2O(C_2H_4O)_a(C_3H_6O)_bCH_3$, $H_2C=CHCH_2(C_2H_4O)_aC(O)CH_3$, $H_2C=C(CH_3)CH_2O(C_2H_4O)_aH$, $H_2C=CHC(CH_3)_2O(C_2H_4O)_aH$, $H_2C=C(CH_3)CH_2O(C_2H_4O)_aCH_3$, $H_2C=C(CH_3)CH_2O(C_2H_4O)_aC(O)CH_3$, $H_2C=C(CH_3)CH_2O(C_2H_4O)_a(C_3H_6O)_bH$, $H_2C=C(CH_3)CH_2O(C_2H_4O)_a(C_3H_6O)_bCH_3$, $H_2C=C(CH_3)CH_2O(C_2H_4O)_aC(O)CH_3$, $HC≡CCH_2O(C_2H_4O)_aH$, $HC≡CCH_2O(C_2H_4O)_aCH_3$, $HC≡CCH_2O(C_2H_4O)_aC(O)CH_3$, $HC≡CCH_2O(C_2H_4O)_a(C_3H_6O)_bH$, $HC≡CCH_2O(C_2H_4O)_a(C_3H_6O)_bCH_3$, and $HC≡CCH_2O(C_2H_4O)_aC(O)CH_3$, wherein a and b are the same as those described above.

The aforementioned organopolysiloxane can be produced by mixing the aforementioned components (a), (b) and (c), and optionally the aforementioned component (d), if necessary. The mixing means is not restricted, and any known mixing means such as a ribbon blender, a rotation/revolution mixer, a pulverizer/mixer or the like, can be used. The mixing order is not restricted. The aforementioned components can be mixed once, or two or three types of the aforementioned components are mixed beforehand, followed by mixing the remaining components. In addition, the temperature at the time of mixing is not particularly restricted, and is appropriately selected from room temperature to 200° C. For example, the aforementioned components (a) and (c) or the aforementioned components (b) and (c) are mixed while heating to about 50° C. to 150° C., followed by mixing optional remaining components such as the aforementioned component (d) and the like. Thereby, better mixing may be achieved.

In the aforementioned mixture, a hydrosilylation reaction proceeds at room temperature or by heating to produce the organopolysiloxane used in the present invention. In order to rapidly carry out the reaction, heating is preferably carried out. The heating temperature is preferably 300° C. or less, and preferably ranges from 20° C. to 200° C., and more preferably ranges from 50° C. to 150° C.

The aforementioned hydrosilylation reaction may be carried out in the presence of an organic solvent. As the organic solvent, a silicone-based solvent such as decamethylpentacyclosiloxane or the like, or a non-silicone-based solvent such as an alcohol-based solvent such as isopropyl alcohol or the like; an aromatic hydrocarbon-based solvent such as toluene, xylene or the like; an ether-based solvent such as dioxane, THF, or the like; an aliphatic hydrocarbon-based solvent; a carboxylic ester-based solvent; a ketone-based solvent; a chlorinated hydrocarbon-based solvent; or the like can be used. Use of the silicone-based solvent is preferable.

In the case of using a non-silicone-based organic solvent, after the hydrosilylation reaction, a less volatile diluent such as dipropylene glycol is added and stripping is carried out under reduced pressure. Thereby, the aforementioned organic solvent is preferably removed by distillation.

The aforementioned organopolysiloxane can be represented by the following average composition formula (1):

$$M_aD_bD^{Link}_cT_dT^{Link}_eQ_f \quad (1)$$

wherein
M represents an $R_3SiO_{1/2}$ unit;
D represents an $R_2SiO_{2/2}$ unit;
T represents an $RSiO_{3/2}$ unit;
Q represents a $SiO_{4/2}$ unit;
$D^{Link}$ represents an $RASiO_{2/2}$ unit;
$T^{Link}$ represents an $ASiO_{3/2}$ unit;
R represents an organic group selected from a substituted or non-substituted, and linear or branched monovalent hydrocarbon group having 1 to 30 carbon atoms, and a group represented by $-C_jH_{2j}O(C_kH_{2k}O)_mR'$ group, wherein j is an integer ranging from 2 to 20, k is an integer ranging from 2 to 4, m is an integer ranging from 2 to 100, R' is a hydrogen atom, a substituted or non-substituted, and linear or branched monovalent hydrocarbon group having 1 to 30 carbon atoms, or an acetyl group;
A is a divalent linking group having a group represented by the following formula (2), (3), (4) or (5):

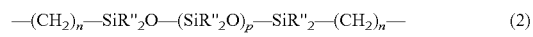
$$-(CH_2)_n-SiR''_2O-(SiR''_2O)_p-SiR''_2-(CH_2)_n- \quad (2)$$

$$-C_sH_{2s}O-(C_tH_{2t}O)_u-C_sH_{2s}- \quad (3)$$

$$-C_vH_{2v}- \quad (4)$$

$$-SiR''_2O-(SiR''_2O)_p-SiR''_2- \quad (5)$$

wherein each R'' independently represents a substituted or non-substituted, and linear or branched monovalent hydrocarbon group having 1 to 30 carbon atoms, and having no aliphatic unsaturated group; n is an integer ranging from 2 to 20; p is an integer ranging from 0 to 500; u is an integer ranging from 2 to 100; s is an integer ranging from 2 to 20; t is an integer ranging from 2 to 4; and v is an integer ranging from 2 to 20, a≥0, b≥0, c≥0, d≥0, e≥0, and f≥0, with the proviso that a+b+c+d+e+f=1, and c+e ranges from 0.001 to 0.6.

As the substituted or non-substituted, and linear or branched monovalent hydrocarbon group having 1 to 30 carbon atoms, the same groups as the aforementioned monovalent hydrocarbon groups can be used.

As the substituted or non-substituted, and linear or branched monovalent hydrocarbon group having 1 to 30 carbon atoms, and having no aliphatic unsaturated group, the same groups as the aforementioned monovalent saturated hydrocarbon groups or monovalent aromatic hydrocarbon groups can be used.

In the aforementioned average composition formula, c+e ranges from 0.001 to 0.6, and the present ratio of $D^{Link}$ and $T^{Link}$ which are crosslinking units is reduced. Therefore, the organopolysiloxane represented by the aforementioned average composition formula has a microcrosslinking three-dimensional network structure.

The viscosity of the aforementioned organopolysiloxane can be indicated as a complex viscosity. The term complex viscosity means a viscosity η* measured on the basis of dynamic viscoelastic properties. The aforementioned complex viscosity η* is calculated by the following equation from a storage elastic modulus (G') and a loss elastic modulus (G"). The complex viscosity in the present invention corresponds to a value obtained in the case of measuring by means of a viscoelastic measurement apparatus under the conditions of the circumstance temperature of 25° C. and frequency of 10 Hz.

$$\text{Complex elastic modulus } G^* = \sqrt{G'^2 + G''^2}$$

$$\text{Complex viscosity: } \eta^* = \frac{G^*}{\omega} = \frac{G^*}{2\pi f}$$

wherein ω represents an angular velocity (rad/s); and ω=2πf, wherein f is a frequency (Hz).

The viscosity of the aforementioned organopolysiloxane preferably ranges from 1,000 mPa·s to 1,000,000 mPa·s, more preferably ranges from 3,000 mPa·s to 500,000 mPa·s, and further more preferably ranges from 5,000 mPa·s to 300,000 mPa·s. In the case of the aforementioned organopolysiloxane being a mixture of two or more types of organopolysiloxanes, the viscosity thereof indicates the viscosity of the aforementioned mixture.

The aforementioned organopolysiloxane exhibits a film-forming sensation and an elastic sensation while the organopolysiloxane is a liquid having fluidity, and for this reason, a distinct elastomeric feeling to the touch is exhibited. Therefore, the aforementioned organopolysiloxane is suitable as an oil-based raw material for a novel silicone elastomer-based cosmetic. In addition, the aforementioned organopolysiloxane can be produced without using an emulsifier. For this reason, the production steps can be simplified.

The cosmetic of the present invention essentially comprises the aforementioned liquid organopolysiloxane. Therefore, the cosmetic of the present invention exhibits not only superior cosmetic properties such as water resistance, makeup durability and the like which are commonly provided by the organopolysiloxanes or the compositions thereof, but also exhibits a superior sensation during use such as a smoothing sensation, compatibility with the skin or the like. The blending amount of the aforementioned (A) liquid organopolysiloxane is not particularly restricted, and can be, for example, an amount ranging from 0.1% by weight (mass) to 40% by weight (mass), preferably ranging from 1% by weight (mass) to 30% by weight (mass), and more preferably ranging from 5% by weight (mass) to 20% by weight (mass), with respect to the weight (mass) of the cosmetic of the present invention.

The cosmetic of the present invention preferably comprises at least one (B) oil agent which is liquid at 25° C. in addition to the aforementioned (A) liquid organopolysiloxane.

The aforementioned (B) oil agent which is liquid at 25° C. is not particularly restricted, and any oil agent can be used therefor, as long as the oil agent has fluidity at 25° C. For example, both a silicone oil and a non-silicone oil such as a hydrocarbon oil or the like can be used. In view of miscibility, as the aforementioned component (B), a silicone oil is preferable. The aforementioned component (B) may be a mixture of two or more types of oil agents.

As the silicone oil of the aforementioned component (B), for example, a cyclic or linear silicone oil which is liquid at room temperature can be used. As examples of cyclic silicones, which are liquid at room temperature, mention may be made of octamethylcyclotetrasiloxane, decamethylcyclopentasiloxane, tetradecamethylcyclohexasiloxane and the like. As examples of linear silicone oils which are liquid at room temperature, mention may be made of, for example, dimethylpolysiloxane (viscosity: 0.65 to 10 cSt/25° C.) and the like. As examples of hydrocarbon oils which are liquid at room temperature, mention may be made of isoparaffin-based hydrocarbons having a boiling point ranging from 60 to 350° C. at a normal pressure. For example, Isoper A, Isoper C, Isoper D, Isoper E, Isoper G, Isoper H, Isoper K, Isoper L, and Isoper M (trademarks), manufactured by Exxon, Shellsol 71 (trademark) manufacture by Shell, Solutol 100, Solutol 130, and Solutol 220 (trademarks) manufactured by Phillips, Parleam 4, Parleam EX, and Parleam 6 (trademarks) manufactured by NOF corporation, and the like.

A mixing ratio of the aforementioned (A) liquid organopolysiloxane and the aforementioned at least one (B) oil agent which is liquid at room temperature in the cosmetic of the present invention is not particularly restricted, and for example, any ratio ranging from 1:99 to 99:1, from 10:90 to 90:10, or from 20:80 to 80:20 can be used for mixing. In view of solubility of the aforementioned (A) liquid organopolysiloxane, the amount of the aforementioned at least one (B) oil agent which is liquid at 25° C. is preferably 50% by weight (mass) or more, more preferably 60% by weight (mass) or more, and furthermore preferably 70% by weight (mass) or more, with respect to the total amount of the cosmetic.

It is preferable that the aforementioned (A) liquid organopolysiloxane and the aforementioned at least one (B) oil agent which is liquid at 25° C. be mixed beforehand to form an organopolysiloxane composition. The aforementioned composition can be produced by mixing the aforementioned component (A) and component (B), as well as other optional components, if necessary. The mixing means is not restricted, and any known mixing means such as a ribbon blender, a rotation/revolution mixer, a pulverizer mixer and the like, can be used. The mixing order is not restricted. In addition, the temperature at the time of mixing is not particularly restricted, and preferably ranges from 10° C. to 100° C., and more preferably ranges from 20° C. to 50° C., in order to control loss due to volatilization of the aforementioned component (B).

The aforementioned composition comprises a liquid oil agent having fluidity at room temperature in the same manner as that of the liquid organopolysiloxane, together with the liquid organopolysiloxane having fluidity at room temperature. They are both in the form of a liquid, and for this reason, they can be uniformly mixed. Therefore, a composition having an oil phase having a superior uniform outer appearance without substantially the presence of the organopolysiloxane in the form of gel particles can be obtained. The aforementioned organopolysiloxane composition contains a uniform oil phase, and for this reason, superior feeling to the touch (in particular, a smoothing sensation and a compatible sensation with respect to the skin) may also be exhibited. Therefore, the aforementioned organopolysiloxane composition is suitable as an oil-based raw material for use in a cosmetic.

The cosmetic of the present invention can comprise at least one (c) oil agent other than the aforementioned component (B), together with the aforementioned (A) liquid organopolysiloxane, and the aforementioned (B) oil agent which is liquid at 25° C. Here, the "oil agent" is generally used as a component of a cosmetic, and is not particularly restricted. The aforementioned (C) oil agent is usually in the form of a liquid at 5° C. to 100° C., may be in the form of a solid such as a wax, and may be in the form of a viscous gum or paste with a high viscosity described below. The aforementioned (C) oil agent can be used as a single type or in combination with two or more types thereof.

The aforementioned (C) oil agent is preferably at least one selected from (C1) a silicone-based oil agent and (C2) a non-silicone-based oil agent selected from organic oils. The types, viscosity and the like of these oil agents can be appropriately selected in accordance with types and usages of the cosmetics.

The aforementioned (C1) silicone-based oil agent is, in general, hydrophobic, and the molecular structure thereof may be linear, cyclic, or branched. Alternatively, although the functional group of the silicone-based oil agent is, in general, a methyl group or a hydroxyl group, the silicone-based oil agent may be an organo-modified silicone in which a part or all parts thereof is/are replaced with functional groups. The organo-modified silicone may have an alkylene chain, an aminoalkylene chain or a polyether chain in addition to the polysiloxane bond as a main chain, and may comprise a so-called block copolymer. In addition, the aforementioned organo-modified group (functional group) may be present at one or both of the terminals or the side chain of the polysiloxane chain. More particularly, as examples thereof, mention may be made of amino-modified silicones, aminopolyether-modified silicones, epoxy-modified silicones, carboxyl-modified silicones, amino acid-modified silicones, acryl-modified silicones, phenol-modified silicones, amidoalkyl-modified silicones, polyamide-modified silicones, aminoglycol-modified silicones, alkoxy-modified silicones, C8-30 higher alkyl-modified silicones, and alkyl-modified silicone resins.

As the linear organopolysiloxanes, organopolysiloxanes represented by the following general formula (6):

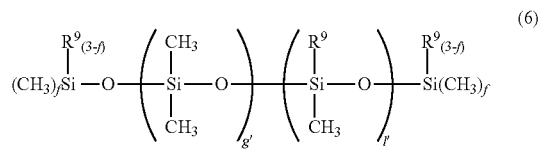

(6)

wherein
$R^9$ is a hydrogen atom, or a group selected from a hydroxyl group, a substituted or non-substituted monovalent hydrocarbon group, an alkoxy group, a polyoxyalkylene group, and a polyorganosiloxane group; f denotes an integer ranging from 0 to 3; g' is an integer ranging from 0 to 10,000; and l' is an integer ranging from 0 to 10,000, with the proviso that 1≥g'+l'≥10,000, can be used. The viscosity of the linear organopolysiloxanes at 25° C. is not particularly restricted, and may usually range from 0.65 to 1,000,000 mm²/sec, which corresponds to the viscosity of a so-called silicone oil. On the other hand, the organopolysiloxane may have an ultra high viscosity which corresponds to that of a silicone gum.

As examples of substituted or non-substituted monovalent hydrocarbon groups, mention may be made of linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cyclopentyl group, a cyclohexyl group and the like; aryl groups having 6 to 30 carbon atoms such as a phenyl group, a tolyl group, a xylyl group, a naphthyl group and the like; and substituted groups thereof, in which hydrogen atoms binding to carbon atoms of the aforementioned groups are at least partially substituted by a halogen atom such as a fluorine atom, or an organic group such as an epoxy group, an acyl group, a carboxyl group, an amino group, an amide group, a (meth)acryl group, a mercapto group, a carbinol group, a phenol group or the like. As examples of alkoxy groups, mention may be made of an alkoxy group having 1 to 30 carbon atoms such as a methoxy group, an ethoxy group, a propoxy group or the like.

As examples of silicone oils, mention may be made of, for example, a dimethylpolysiloxane in which both molecular terminals are capped with trimethylsiloxy groups (dimethylsilicone with a low viscosity such as 2 mPa·s or 6 mPa·s to dimethylsilicone with a high viscosity such as 1,000,000 mPa·s, and in addition, a dimethylsilicone with an ultra-high viscosity), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl(trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl(3,3,3-trifluoropropyl)siloxane and dimethylsiloxane in which both molecular terminals are capped with trimethylsiloxy groups, an α,ω-diethoxypolydimethylsiloxane, a higher alkoxy-modified silicone, a higher fatty acid-modified silicone, dimethiconol, a siloxane with a low molecular weight such as a 1,1,1,3,5,5,5-heptamethyl-3-octyltrisiloxane, a 1,1,1,3, 5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, or the like, a dimethylpolysiloxane in which both molecular terminals are capped with trimethylsilyl groups, an α,ω-dihydroxypolydimethylsiloxane, and the like.

In the cosmetic of the present invention, a so-called silicone gum having 1,000,000 mm²/s or more, which has ultra-high viscosity, can also be used as a silicone oil. The silicone gum is a linear diorganopolysiloxane having an ultra-high degree of polymerization, and is also referred to as a silicone raw rubber or an organopolysiloxane gum. The silicone gum possesses a high degree of polymerization, and for this reason, it has a measurable degree of plasticity. In view of this, the silicone gum is different from the aforementioned oil silicones. The aforementioned silicone gum can be blended in the cosmetic according to the present invention as it is, or as a liquid gum dispersion (an oil dispersion of the silicone gum) in which the silicone gum is dispersed in an oil silicone.

As examples of the aforementioned silicone raw rubber, mention may be made of substituted or non-substituted organopolysiloxanes having a dialkylsiloxy unit (D unit) such as dimethylpolysiloxane, methylphenylpolysiloxane, aminopolysiloxane, methylfluoroalkyl polysiloxane and the like, or those having a slightly-crosslinking structure thereof and the like. As representative examples thereof, there are those represented by the following general formula:

$$R^{10}(CH_3)_2SiO\{(CH_3)_2SiO\}_s\{(CH_3)R^{12}SiO\}_t Si(CH_3)_2R^{10}$$

wherein $R^{12}$ is a group selected from a vinyl group, a phenyl group, an alkyl group having 6 to 20 carbon atoms, an aminoalkyl group having 3 to 15 carbon atoms, a perfluoroalkyl group having 3 to 15 carbon atoms, and a quaternary ammonium salt group-containing alkyl group having 3 to 15 carbon atoms; the terminal group $R^{10}$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms; s=2,000 to 6,000; t=0 to 1,000; and s+t=2,000 to 6,000. Among these, a dimethylpolysiloxane raw rubber having a degree of polymerization ranging from 3,000 to 20,000 is preferable. In addition, an amino-modified methylpolysiloxane raw rubber having a 3-aminopropyl group, an N-(2-aminoethyl)-3-aminopropyl group or the like on the side chain or the terminal of the molecule is preferable. In addition, in the present invention, the silicone gum can be used alone or in combination with two or more types thereof, as necessary.

The silicone gum has an ultra-high degree of polymerization. For this reason, the silicone gum can exhibit a superior retention property on hair or skin, and can form a protective film with a superior aeration property. For this reason, the silicone gum is a component, which can particularly provide glossiness and luster on skin or hair and can impart a texture with tension on the entire skin or hair during use and after use.

The blending amount of the silicone gum may range from 0.05% by weight (mass) to 30% by weight (mass) and may preferably range from 1% by weight (mass) to 15% by weight (mass), with respect to the total amount of the cosmetic. When the silicone gum is used as an emulsion composition prepared via a step of preliminarily emulsifying (including emulsion polymerization), the silicone gum can be easily blended, and can stably be blended in the cosmetic of the present invention. If the blending amount of the silicone gum is below the aforementioned lower limit, an effect of imparting a specific feeling to the touch or glossiness with respect to skin or hair may be insufficient.

As cyclic organopolysiloxanes, for example, organopolysiloxanes represented by the following general formula (7):

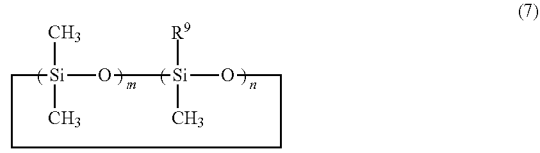

(7)

wherein
$R^9$ is the same as defined above;
m is an integer ranging from 0 to 8; and
n is an integer ranging from 0 to 8, with the proviso that $3 \geq m+n \geq 8$,
can be used.

As examples of cyclic organopolysiloxanes, mention may be made of hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl)tetramethylcyclotetrasiloxane and the like.

As branched organopolysiloxanes, for example, organosilanes represented by the following general formula (8):

(8)

wherein
$R^9$ is the same as defined above;
p is an integer ranging from 1 to 4;
branched organopolysiloxanes with a low-molecular-weight, and so-called silicone resins in the form of a liquid, a solid or the like can be used.

As branched organopolysiloxanes, mention may be made of a siloxane with a low-molecular-weight such as methyltristrimethylsiloxysilane, ethyltristrimethylsiloxysilane, propyltristrimethylsiloxysilane, tetrakistrimethylsiloxysilane, phenyltristrimethylsiloxysilane or the like; or a silicone resin of a highly branched molecular structure, a net-like molecular structure or a cage-like molecular structure may be used. A silicone resin containing at least a monoorganosiloxy unit (T unit) and/or a siloxy unit (Q unit) is preferable. The aforementioned silicone resins having branched units possess a net-like structure. In the case of applying the silicone resins to skin, hair or the like, a uniform film is formed and protective effects with respect to dryness and low temperature are provided. In addition, the silicone resins having branched units tightly adhere to skin, hair or the like, and can provide glossiness and a transparent impression to skin, hair or the like.

Hereinafter, a higher alkyl-modified silicone, an alkyl-modified silicone resin and a polyamide-modified silicone resin, which are particularly preferable as the organo-modified silicones, are described. The higher alkyl-modified silicone is in the form of a wax at room temperature, and is a useful component as a part of a base material of an oil-based solid cosmetic. Therefore, the higher alkyl-modified silicones can be preferably used in the cosmetics of the present invention. As examples of the aforementioned higher alkyl-modified silicone waxes, mention may be made of a methyl(long chain alkyl)polysiloxane having both molecular terminals capped with trimethylsiloxy groups, a copolymer of a methyl(long chain alkyl)siloxane and a dimethylpolysiloxane having both molecular terminals capped with trimethylsiloxy groups, a dimethylpolysiloxane modified with long chain alkyls at both terminals, and the like. As examples of commercially available products thereof, mention may be made of, AMS-C30 Cosmetic Wax, 2503 Cosmetic Wax and the like (manufactured by Dow Corning Corporation, in the USA).

In the cosmetic of the present invention, the higher alkyl-modified silicone wax preferably has a melting point of 60° C. or higher in view of a cosmetic durability effect and stability at increased temperatures.

The alkyl-modified silicone resin is a component for imparting sebum durability, a moisture-retaining property, and a fine texture feeling to the touch to the cosmetic, and one in the form of a wax at room temperature can be preferably used. For example, a silsesquioxane resin wax described in Published Japanese Translation No. 2007-532754 of the PCT International Application may be mentioned. As commercially available products thereof, SW-8005 C30 RESIN WAX (manufactured by Dow Corning Corporation in the USA) and the like may be mentioned.

As examples of polyamide-modified silicones, mention may be made of, for example, siloxane-based polyamide compounds described in U.S. Pat. No. 5,981,680 (Japanese Unexamined Patent Application, First Publication No. 2000-038450) and Published Japanese Translation No. 2001-512164 of the PCT International Application. As examples of commercially available products, mention may be made of 2-8178 Gellant, 2-8179 Gellant and the like (manufactured by Dow Corning Corporation, in the USA). The aforementioned polyamide-modified silicones are also useful as an oil-based raw material, and in particular, a thickening/gelling agent of a silicone oil.

As the aforementioned (C2) organic oil agent, (C2-1) a higher alcohol, (C2-2) a hydrocarbon oil, (C2-3) a fatty acid ester oil, and (C2-4) a higher fatty acid, fats and oils, or a fluorine-based oil agent are representative. In the present invention, the aforementioned (C2) organic oil agent is not particularly restricted, but a higher alcohol, a hydrocarbon oil, a fatty acid ester oil and a higher fatty acid are preferable.

The aforementioned (C2-1) higher alcohol is, for example, a higher alcohol having 10 to 30 carbon atoms. The aforementioned higher alcohol is a saturated or unsaturated monovalent aliphatic alcohol, and the moiety of the hydrocarbon group thereof may be linear or branched, but a linear one is preferable. As examples of higher alcohols having 10 to 30 carbon atoms, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol and the like. In the present invention, use of a higher alcohol having a melting point ranging from 40 to 80° C. or use of a combination of plural higher alcohols so as to have a melting point thereof ranging from 40 to 70° C. is preferable. The aforementioned higher alcohols can form an aggregate which is a so-called alpha gel, together with a surfactant. Thereby, the higher alcohols may possess a function of increasing viscosity of a preparation, and stabilize an emulsion. For this reason, they are, in particular, useful as a base agent of a cosmetic.

As examples of the aforementioned (C2-2) hydrocarbon oils, mention may be made of liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene and the like.

As examples of the aforementioned (C2-3) fatty acid ester oils, mention may be made of hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of *macadamia* nut oil fatty acid, phytosteryl ester of *macadamia* nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like. Lanolin and lanolin derivatives can also be used as the fatty acid ester oils.

As examples of the aforementioned (C2-4) higher fatty acids, mention may be made of, for example, lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As the aforementioned (C) oil agent, a silicone-based oil agent and a non-silicone-based oil agent may be used in combination. By use of the combination, in addition to a refreshing feeling to the touch which the silicone oils inherently possess, the moisture of skin, hair or the like can be maintained and a moisturizing sensation (also referred to as a moisturizing feeling to the touch) can be provided to the cosmetics of the present invention. In addition, an advantage in that stability of the cosmetics over time is not impaired can be obtained. Furthermore, by a cosmetic comprising a hydrocarbon oil and/or a fatty acid ester oil and a silicone oil, the aforementioned moisturizing components (namely, the hydrocarbon oils and/or fatty acid ester oils) can be stably and uniformly applied on skin or hair. For this reason, effects of retaining moisture on the skin of the moisturizing components are improved. Therefore, a cosmetic comprising both a non-silicone-based oil agent and a silicone-based oil agent has an advantage in that an increased moisturizing feeling to the touch can be provided, as compared with a cosmetic comprising only a non-silicone-based oil agent (such as a hydrocarbon oil, a fatty acid ester oil or the like).

In the present invention, in addition to the aforementioned oil agents, fats and oils, higher fatty acids, fluorine-based oils and the like may be used as the aforementioned (C) oil agents, and they may be used in combination of two or more types thereof. In particular, fats and oils derived from vegetables provide a healthy image derived from natural products and exhibit a superior moisture-retaining property and superior compatibility with skin or hair. For this reason, they are preferably used in a cosmetic of the present invention.

As fats and oils, as examples of natural animal or vegetable fats and oils and semi-synthetic fats and oils, mention may be made of avocado oil, linseed oil, almond oil, ibota wax, *perilla* oil, olive oil, cacao butter, kapok wax, kaya oil, carnauba wax, liver oil, candelilla wax, beef tallow, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, olive oil, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, *macadamia* nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, POE cholesterol ether, monostearyl glycerol ether (batyl alcohol), monooleyl glycerol ether (selachyl alcohol), egg yolk oil and the like, with the proviso that POE means polyoxyethylene.

As examples of fluorine-based oils, mention may be made of perfluoropolyether, perfluorodecalin, perfluorooctane and the like.

The blending amount of the aforementioned (C) oil agent in the cosmetic of the present invention is not particularly restricted, and preferably ranges from 0.1% by weight (mass) to 90% by weight (mass), more preferably ranges from 0.5% by weight (mass) to 70% by weight (mass), furthermore preferably ranges from 1% by weight (mass) to 50% by weight (mass), and in particular, preferably ranges from 5% by weight (mass) to 25% by weight (mass).

The cosmetic of the present invention can preferably comprise (D) a surfactant. The aforementioned (D) surfactant can be used as a single type or in combination with two or more types thereof, in accordance with the purpose of the cosmetic.

Types of the aforementioned (D) surfactants are not particularly restricted, and can be at least one type selected from the group consisting of (D1) anionic surfactants, (D2) cationic surfactants, (D3) nonionic surfactants, (D4) amphoteric surfactants and (D5) semi-polar surfactants.

As examples of the aforementioned (D1) anionic surfactants, mention may be made of saturated or unsaturated fatty acid salts such as sodium laurate, sodium stearate, sodium oleate, sodium linoleate and the like; alkylsulfuric acid salts; alkylbenzenesulfonic acids such as hexylbenzenesulfonic acid, octylbenzenesulfonic acid, dodecylbenzenesulfonic acid and the like, as well as salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamidesulfuric acid salts; alkyl- or alkenylphosphoric acid salts; alkylamidephosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. As examples of salts, mention may be made of alkali metal salts such as a sodium salt and the like, alkaline earth metal salts such as a magnesium salt and the like, alkanolamine salts such as a triethanolamine salt and the like, and an ammonium salt.

As examples of the aforementioned (D2) cationic surfactants, mention may be made of alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE) oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, stearic diethylaminoethylamide, stearic dimethylaminopropylamide, behenic amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

As examples of the aforementioned (D3) nonionic surfactants, mention may be made of polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylene glycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. A polyoxyalkylene-modified silicone, a polyglycerol-modified silicone, or a glycerol-modified silicone in which an alkyl branch, a linear silicone branch, a siloxane dendrimer branch or the like may be possessed together with a hydrophilic group at the same time, if necessary, can also be preferably used.

The organo-modified silicone already described as the aforementioned (C) oil agent may possess an aspect as a nonionic emulsifier depending on the structure thereof, in addition to an aspect as an oil agent. Namely, the organo-modified silicone oils such as a polyoxyalkylene-modified silicone, a polyglycerol-modified silicone, a glycerol-modified silicone and the like, possessing both a hydrophilic moiety and a hydrophobic moiety in a molecule possess a function as a nonionic surfactant. They may function as an auxiliary agent for improving stability of the aforementioned (D3) nonionic surfactant and may improve stability of the entire preparation. Therefore, they can be used in combination.

As examples of the aforementioned (D4) amphoteric surfactants, mention may be made of imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. More particularly, as examples thereof, mention may be made of imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt and the like; alkylbetaine-type amphoteric surfactants such as lauryl dimethylaminoacetic acid betaine, myristyl betaine and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine and the like.

As examples of the aforementioned (D5) semi-polar surfactants, mention may be made of alkylamine oxide-type surfactants, alkylamine oxides, alkylamide amine oxides, alkylhydroxyamine oxides and the like. Alkyldimethylamine oxides having 10 to 18 carbon atoms, alkoxyethyl dihydroxyethylamine oxides having 8 to 18 carbon atoms and the like are preferably used. More particularly, as examples thereof, mention may be made of dodecyldimethylamine oxide, dimethyloctylamine oxide, diethyldecylamine oxide, bis-(2-hydroxyethyl) dodecylamine oxide, dipropyltetradecylamine oxide, methylethylhexadecylamine oxide, dodecylamidopropyl dimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The blending amount of the aforementioned (D) surfactants in the cosmetic of the present invention is not particularly restricted. In order to improve a cleansing property, the surfactants can be blended in an amount ranging from 0.1% by weight (mass) to 90% by weight (mass) and preferably ranging from 1% by weight (mass) to 50% by weight (mass) in the total amount of the cosmetic composition. In view of a cleansing property, the amount is preferably 25% by weight (mass) or more.

The cosmetic of the present invention can further comprise (E) an alcohol. As the aforementioned (E) alcohols, one or more types of polyhydric alcohols and/or a monovalent lower alcohols can be used. As examples of lower alcohols, mention may be made of ethanol, isopropanol, n-propanol, t-butanol, s-butanol and the like. Ethanol is preferable. As examples of polyhydric alcohols, mention may be made of divalent alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, octylene glycol and the like; trivalent alcohols such as glycerol, trimethylol propane, 1,2,6-hexanetriol and the like; polyhydric alcohols having 4 or more valences such as pentaerythritol, xylitol and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol and the like. In addition to the aforementioned low-molecule polyhydric alcohols, polyhydric alcohol polymers such as diethylene glycol, dipropylene glycol, triethylene glycol, propylene glycol, tetraethylene glycol, diglycerol, polyethylene glycol, triglycerol, tetraglycerol, polyglycerol and the like may be mentioned. Among these, 1,3-propanediol, 1,3-butylene glycol, sorbitol, dipropylene glycol, glycerol, and polyethylene glycol are, in particular, preferable.

The blending amount of the aforementioned (E) alcohols preferably ranges from 0.1% by weight (mass) to 50% by weight (mass) with respect to the total amount of the cosmetic. Alcohols can be blended in an amount ranging from about 5% by weight (mass) to 30% by weight (mass) with respect to the total amount of the cosmetic in order to improve storage stability of the cosmetic. This is one preferable mode for carrying out the present invention.

The cosmetic of the present invention preferably further comprises (F1) a thickening agent and/or (F2) a gelling agent. They can be used as a single type or two or more types thereof if necessary.

As an aqueous thickening agent and/or gelling agent, a water-soluble polymer is preferably used. As the aforementioned water-soluble polymer, any one of amphoteric, cationic, anionic, nonionic, and water-swellable clay minerals can be used as long as they are commonly used in a cosmetic. One type or two or more types of water-soluble polymers can be used. The aforementioned water-soluble polymers have an effect of thickening a hydrous component, and for this reason, they are useful in the case of obtaining a hydrous cosmetic, and in particular, in the form of a gel hydrous cosmetic, a water-in-oil emulsion cosmetic, and an oil-in-water emulsion cosmetic.

As examples of natural water-soluble polymers, mention may be made of vegetable-based polymers such as gum Arabic, tragacanth gum, galactan, guar gum, carob gum, karaya gum, carrageenan, pectin, agar, quince seed, algal colloid, starch (rice, corn, potato, or wheat), glycyrrhizinic acid and the like; microorganism-based polymers such as xanthan gum, dextran, succinoglucan, pullulan, and the like; and animal-based polymers such as collagen, casein, albumin, gelatin, and the like. In addition, as examples of semi-synthetic water-soluble polymers, mention may be made of, for example, starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate and the like. As examples of synthetic water-soluble polymers, mention may be made of, for example, vinyl-based polymers such as polyvinyl alcohol, polyvinyl methyl ether-based polymer, polyvinylpyrrolidone, carboxyvinyl polymer (CARBOPOL 940, or CARBOPOL 941; manufactured by The Lubrizol Corporation); polyoxyethylene-based polymers such as polyethylene glycol 20,000, polyethylene glycol 6,000, polyethylene glycol 4,000 and the like; copolymer-based polymers such as a copolymer of polyoxyethylene and polyoxypropylene, PEG/PPG methyl ether and the like; acryl-based polymers such as poly(sodium acrylate), poly(ethyl acrylate), polyacrylamide and the like; polyethylene imines; cationic polymers and the like. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride. They may be any one of natural ones and synthesized ones.

As examples of components which can be preferably blended in a cosmetic, mention may be made of, in particular, a cationic water-soluble polymers. As examples of the aforementioned cationic water-soluble polymers, mention may be made of quaternary nitrogen-modified polysaccharides such as cation-modified cellulose, cation-modified hydroxyethylcellulose, cation-modified guar gum, cation-modified locust bean gum, cation-modified starch and the like; dimethyldiallylammonium chloride derivatives such as a copolymer of dimethyldiallylammonium chloride and acrylamide, poly(dimethylmethylene piperidinium chloride) and the like; vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride and the like; and methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, methacryloylethyl trimethylammonium chloride and methoxy polyethylene glycol methacrylate, and the like.

In addition, as a component which can be preferably blended in a cosmetic, an amphoteric water-soluble polymer can be mentioned. More particularly, as examples of amphoteric water-soluble polymers, mention may be made of amphoterized starches; dimethyldiallylammonium chloride derivatives such as a copolymer of acrylamide, acrylic acid, and dimethyldiallylammonium chloride, and a copolymer of acrylic acid and dimethyldiallylammonium chloride; and methacrylic acid derivatives such as polymethacryloylethyl dimethylbetaiffe, a copolymer of methacryloyloxyethyl carboxybetaine and alkyl methacrylate, a copolymer of octylacrylamide, hydroxypropyl acrylate and butylaminoethyl methacrylate, and a copolymer of N-methacryloyloxyethyl N,N-dimethylammonium α-methylcarboxybetaine and alkyl methacrylate.

The water-soluble polymers can also be blended in order to improve a sensation during use of cosmetics such as feeling to the touch with respect to the skin, hair and the like, conditioning effects and the like.

As examples of oil-soluble thickening and/or gelling agents, mention may be made of metallic soaps such as aluminum stearate, magnesium stearate, zinc myristate and the like; amino acid derivatives such as N-lauroyl-L-glutamic acid, α,γ-di-n-butylamine and the like; dextrin fatty acid esters such as dextrin palmitate, dextrin stearate, dextrin 2-ethylhexanoate palmitate and the like; sucrose fatty acid esters such as sucrose palmitate, sucrose stearate and the like; benzylidene derivatives of sorbitol such as monobenzylidene sorbitol, dibenzylidene sorbitol and the like; and the like.

As the aforementioned (F1) thickening and/or (F2) gelling agent, an organo-modified clay mineral can be used. The organo-modified clay mineral can be used as a gelling agent for the oil agent(s) in the same manner as described in the aforementioned oil-soluble thickening and/or gelling agent. As examples of organo-modified clay minerals, mention may be made of, for example, dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate and the like. As examples of commercially available products thereof, mention may be made of Benton 27 (benzyldimethylstearylammonium chloride-treated hectorite, manufactured by Nationalred Co.), Benton 38 (distearyldimethylammonium chloride-treated hectorite, manufactured by Nationalred Co.) and the like.

The usage amount of the aforementioned (F1) thickening and/or (F2) gelling agent in the cosmetic of the present invention is not particularly restricted, and may preferably range from 0.5 to 50 parts by weight (mass), and more preferably range from 1 to 30 parts by weight (mass), with respect to 100 parts by weight (mass) of the oil agent(s). The ratio thereof in the cosmetic preferably ranges from 0.01% by weight (mass) to 30% by weight (mass), more preferably ranges from 0.1% by weight (mass) to 20% by weight (mass), and furthermore preferably ranges from 1% by weight (mass) to 10% by weight (mass).

By thickening or gelling the oil agent(s) in the cosmetic of the present invention, the viscosity or hardness of the cosmetic can be made appropriate, and the outer appearance, blending properties, and the sensation during use can be improved. In addition, a desirable formulation and/or a desirable form of the cosmetic can be achieved. In addition, there are advantages in view of qualities in that an oily sensation (oily and sticky feeling to the touch) can be further totally controlled, and a retaining property can be further improved.

The cosmetic of the present invention can further comprise (G1) powder and/or (G2) coloring agent. "Powder" in the present invention is that commonly used as a component of a cosmetic, and includes white and colored pigments and extender pigments. The white and colored pigments are used in coloring a cosmetic, and on the other hand, the extender pigments are used in improvement in a feeling to the touch of a cosmetic and the like. As the aforementioned (G1) powder in the present invention, white or colored pigments and extender pigments which are commonly used in cosmetics can be used without any restrictions. One type or two or more types of powders may be preferably blended. Here, "(G2) coloring agent" means a non-powder coloring agent.

With respect to the aforementioned (G1) powders, there is no restriction on the form thereof (sphere, bar, needle, plate, amorphous, spindle or the like), the particle size (aerosol, microparticle, pigment-grade particle, or the like), and the particle structure (porous, non-porous or the like) thereof. The average primary particle size of the powders preferably ranges from 1 nm to 100 μm.

As examples of the aforementioned (G1) powders and/or (G2) coloring agents, mention may be made of, for example, inorganic powders, organic powders, surfactant metal salt powders (metallic soaps), colored pigments, pearl pigments, metal powder pigments and the like. In addition, hybrid products of the aforementioned pigments can also be used.

More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like.

As examples of organic powders, mention may be made of polyamide powder, polyester powder, polyethylene powder, polypropylene powder, polystyrene powder, polyurethane powder, benzoguanamine powder, polymethylbenzoguanamine powder, polytetrafluoroethylene powder, poly (methyl methacrylate) powder, cellulose, silk powder, nylon powder, nylon 12, nylon 6, silicone powder, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine and the like.

As examples of surfactant metal salt powders, mention may be made of zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like.

As examples of colored pigments, mention may be made of inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, laked pigments of natural pigments such as carminic acid, laccaic acid, carthamin, brazilin, crocin and the like.

As examples of pearl pigments, mention may be made of titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like.

As examples of metal powder pigments, mention may be made of powders of metals such as aluminum, gold, silver, copper, platinum, stainless steel, and the like.

In addition, in the aforementioned (G1) powders and/or (G2) coloring agents, a part or all parts thereof may, in particular, preferably be subjected to a surface treatment such as a water-repellent treatment, a hydrophilic treatment or the like. In addition, composited products in which the aforementioned powders are mutually composited may be used. In addition, surface-treated products in which the aforementioned powders have been subjected to a surface treatment with a general oil agent, a silicone compound, a fluorine compound, a surfactant, a thickening agent or the like can also be used. One type thereof or two or more types thereof can be used, as necessary.

The water-repellant treatments are not particularly restricted. The aforementioned (G1) powders and/or (G2) coloring agents can be treated with various types of water-repellant surface treatment agents. As examples thereof, mention may be made of organosiloxane treatments such as a methylhydrogenpolysiloxane treatment, a silicone resin treatment, a silicone gum treatment, an acryl silicone treatment, a fluorinated silicone treatment and the like; metallic soap treatments such as a zinc stearate treatment and the like; silane treatments such as a silane coupling agent treatment, an alkylsilane treatment and the like; fluorine compound treatments such as a perfluoroalkylsilane treatment, a perfluoroalkyl phosphate treatment, a perfluoro polyether treatment and the like; amino acid treatments such as an N-lauroyl-L-lysine treatment and the like; oil agent treatments such as a squalane treatment and the like; acryl treatments such as an alkyl acrylate treatment and the like. The aforementioned treatments can be used in combination of two or more types thereof.

As the aforementioned (G1) powders, silicone elastomer powders can also be used. The silicone elastomer powder is a crosslinked product of a linear diorganopolysiloxane mainly formed from a diorganosiloxane unit (D unit). The silicone elastomer powder can be preferably produced by crosslink-reacting an organohydrogenpolysiloxane having a silicon-binding hydrogen atom at the side chain or the terminal and a diorganopolysiloxane having an unsaturated hydrocarbon group such as an alkenyl group or the like at the side chain or the terminal, in the presence of a catalyst for a hydrosilylation reaction. The silicone elastomer powder has an increased flexibility and elasticity, and exhibits a superior oil-absorbing property, as compared with a silicone resin powder formed from T units and Q units. For this reason, the silicone elastomer powder absorbs sebum on the skin and can prevent makeup running.

The silicone elastomer powders can be in various forms such as a spherical form, a flat form, an amorphous form and the like. The silicone elastomer powders may be in the form of an oil dispersant. In the cosmetic of the present invention, silicone elastomer powders in the form of particles, which have a primary particle size observed by an electron microscope and/or an average primary particle size measured by a laser diffraction/scattering method ranging from 0.1 to 50 μm, and in which the primary particle is in a spherical form, can be preferably blended. In addition, the silicone elastomer constituting the silicone elastomer powders may have a hardness preferably not exceeding 80, and more preferably not exceeding 65, when measured by means of a type A durometer according to JIS K 6253 "Method for determining hardness of vulcanized rubber or thermoplastic rubber".

The aforementioned silicone elastomer powders can be used in the cosmetic of the present invention, in the form of an aqueous dispersion. As examples of commercially available products of the aforementioned aqueous dispersions, mention may be made of, for example, "BY 29-129" and "PF-2001 PIF Emulsion" manufactured by Dow Corning Toray Co., Ltd., and the like.

The silicone elastomer powders may be subjected to a surface treatment with a silicone resin, silica or the like. As examples of the aforementioned surface treatments, mention may be made of, for example, those described in Japanese Unexamined Patent Application, First Publication No. H02-243612; Japanese Unexamined Patent Application, First Publication No. H08-12545; Japanese Unexamined Patent Application, First Publication No. H08-12546; Japanese Unexamined Patent Application, First Publication No. H08-12524; Japanese Unexamined Patent Application, First Publication No. H09-241511; Japanese Unexamined Patent Application, First Publication No. H10-36219; Japanese Unexamined Patent Application, First Publication No. H11-193331; Japanese Unexamined Patent Application, First Publication No. 2000-281523 and the like. As the silicone elastomer powders, crosslinking silicone powders listed in "Japanese Cosmetic Ingredients Codex (JCIC)" correspond thereto. As commercially available products, there are Trefil E-506S, Trefil E-508, 9701 Cosmetic Powder, and 9702 Powder, manufactured by Dow Corning Toray Co., Ltd., and the like. The aforementioned silicone elastomer powder may be surface-treated. As examples of the surface treatment agents, mention may be made of methylhydrogenpolysiloxane, silicone resins, metallic soap, silane coupling agents, inorganic oxides such as silica, titanium oxide and the like and fluorine compounds such as perfluoroalkylsilane, perfluoroalkyl phosphoric ester salts and the like.

The blending amount of the aforementioned (G1) powder and/or (G2) coloring agent in the cosmetic of the present invention is not particularly restricted, and may preferably range from 0.1% by weight (mass) to 50% by weight (mass), more preferably range from 1% by weight (mass) to 30% by weight (mass), and furthermore preferably range from 5% by weight (mass) to 15% by weight (mass) with respect to the total amount of the cosmetic.

The cosmetic of the present invention can further comprise (H) a UV-ray protective component. The aforementioned (H) UV-ray protective component is preferably hydrophobic so that the component is completely insoluble in water at room temperature or the solubility thereof with respect to 100 g of water is below 1% by weight (mass). The aforementioned (H) UV-ray protective component is a component for blocking or diffusing UV rays. Among UV-ray protective components, there are inorganic UV-ray protective components and organic UV-ray protective components. If the cosmetics of the present invention are to have sunscreening effects, at least one type of inorganic or organic UV-ray protective component, and in particular, an organic UV-ray protective component is preferably contained.

The inorganic UV-ray protective components may be components in which the aforementioned inorganic powder pigments, metal powder pigments and the like are blended as UV-ray dispersants. As examples thereof, mention may be made of metal oxides such as titanium oxide, zinc oxide, cerium oxide, titanium suboxide, iron-doped titanium oxides and the like; metal hydroxides such as iron hydroxides and the like; metal flakes such as platy iron oxide, aluminum flake and the like; and ceramics such as silicon carbide and the like. Among these, at least one type of a material selected from fine particulate metal oxides and fine particulate metal hydroxides with an average particle size ranging from 1 to 100 nm in the form of granules, plates, needles, or fibers is, in particular, preferable. The aforementioned powders are preferably subjected to conventional surface treatments such as fluorine compound treatments, among which a perfluoroalkyl phosphate treatment, a perfluoroalkylsilane treatment, a perfluoropolyether treatment, a fluorosilicone treatment, and a fluorinated silicone resin treatment are preferable; silicone treatments, among which a methylhydrogenpolysiloxane treatment, a dimethylpolysiloxane treatment, and a vapor-phase tetramethyltetrahydrogencyclotetrasiloxane treatment are preferable; silicone resin treatments, among which a trimethylsiloxysilicic acid treatment is preferable; pendant treatments which are methods of adding alkyl chains after the vapor-phase silicone treatment; silane coupling agent treatments; titanium coupling agent treatments; silane treatments among which an alkylsilane treatment and an alkylsilazane treatment are preferable; oil agent treatments; N-acylated lysine treatments; polyacrylic acid treatments; metallic soap treatments in which a stearic acid salt or a myristic acid salt is preferably used; acrylic resin treatments; metal oxide treatments and the like. Multiple treatments described above are preferably carried out. For example, the surface of the fine particulate titanium oxide can be coated with a metal oxide such as silicon oxide, alumina or the like, and then, a surface treatment with an alkylsilane can be carried out. The total amount of the material used for the surface treatment may preferably range from 0.1% by weight (mass) to 50% by weight (mass) based on the amount of the powder.

The organic UV-ray protective components are generally lipophilic. More particularly, as examples of the aforementioned organic UV-ray protective components, mention may be made of benzoic acid-based UV-ray absorbers such as paraminobenzoic acid (hereinafter, referred to as PABA), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, 2-[4-(diethylamino)-2-hydroxybenzoyl]benzoic acid hexyl ester (trade name: Uvinul A Plus) and the like; anthranilic acid-based UV-ray absorbers such as homomethyl N-acetylanthranilate and the like; salicylic acid-based UV-ray absorbers such as amyl salicylate, menthyl salicylate, homomethyl salicylate, octyl salicylate, phenyl salicylate, benzyl salicylate, p-isopropanolphenyl salicylate and the like; cinnamic acid-based UV-ray absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxycinnamate, 3-methyl-4-[methylbis(trimethylsiloxy)silyl]butyl 3,4,5-trimethoxycinnamate, dimethicodiethyl benzal malonate (trade name: Parsol SLX (INCI name=polysilicone-15) and the like; benzophenone-based UV-ray absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, hydroxy-4-n-octoxybenzophenone, 4-hydroxy-3-carboxybenzophenone and the like; 3-(4'-methylbenzylidene)-d,l-camphor; 3-benzylidene-d,l-camphor; urocanic acid; ethyl urocanate; 2-phenyl-5-methylbenzoxazole; benzotriazole-based UV-ray absorbers such as 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzaladine, dianisoylmethane, 4-methoxy-4'-t-butylbenzoylmethane, 5-(3,3-dimethyl-2-norbonylidene)-3-pentan-2-one, 2,2'-methylenebis(6-(2H-benzotriazol-2-yl)-4-(1,1,3,3-tetramethylbutyl)phenol) (trade name: trademark TINOSORB M) and the like; triazine-based UV-ray absorbers such as 2,4,6-tris[4-(2-ethylhexyloxycarbonyl)anilino]1,3,5-triazine (INCI: octyltriazone), 2,4-bis{[4-(2-ethyl-hexyloxy)-2-hydroxy]phenyl}-6-(4-methoxyphenyl)-1,3,5-triazine (INCI: bis-ethylhexyloxyphenol methoxyphenyl triazine, trade name: trademark TINOSORB S) and the like; 2-ethylhexyl 2-cyano-3,3-diphenylprop-2-enoate (INCI: octocrylene) and the like.

Furthermore, hydrophobic polymer powders containing the aforementioned organic UV-ray protective components inside thereof can also be used. The polymer powder may be hollow or not, may have an average primary particle size thereof ranging from 0.1 to 50 μm and may have a particle size distribution thereof of either broad or sharp. As examples of the polymers, mention may be made of acrylic resins, methacrylic resins, styrene resins, polyurethane resins, polyethylene, polypropylene, polyethylene terephthalate, silicone resins, nylons, acrylamide resins, and silylated polypeptide resins. Polymer powders containing the organic UV-ray protective components in an amount ranging from 0.1% by weight (mass) to 30% by weight (mass) with respect to the amount of the powder are preferable. Polymer powders containing 4-tert-butyl-4'-methoxydibenzoylmethane, which is a UV-A absorber, are particularly preferable.

The aforementioned (H) UV-ray protective components which can be preferably used in the cosmetics of the present invention may be at least one type of compound selected from the group consisting of fine particulate titanium oxide, fine particulate zinc oxide, 2-ethylhexyl paramethoxycinnamate, 4-tert-butyl-4'-methoxydibenzoylmethane, benzotriazole-based UV-ray absorbers and triazine-based UV-ray absorbers. The aforementioned (H) UV-ray protective components are commonly used and easily available, and exhibit superior effects of preventing ultraviolet rays. For these reasons, the aforementioned UV-ray protective components are preferably used. In particular, inorganic UV-ray protective components and organic UV-ray protective components are preferably used in combination. In addition, UV-A protective components and UV-B protective components are further preferably used in combination.

In the cosmetic of the present invention, the aforementioned (H) UV-ray protective component(s) may be blended in a total amount preferably ranging from 0.1% by weight (mass) to 40.0% by weight (mass), and more preferably ranging from 0.5% by weight (mass) to 15.0% by weight (mass), with respect to the total amount of the cosmetic can be blended.

In the cosmetics of the present invention, other components usually used in cosmetics for hair can be blended within a range which does not impair the effects of the present invention, such as organic resins, humectants, Preservatives, anti-microbial agents, perfumes, salts, oxidants or antioxidants, pH adjusting agents, chelating agents, algefacients, anti-inflammatory agents, physiologically active components (such as whitening agents, cell activators, agents for ameliorating skin roughness, blood circulation accelerators, astringents, antiseborrheic agents and the like), vitamins, amino acids, nucleic acids, hormones, clathrate compounds, natural plant extract components, seaweed extract components, herb components, water, volatile solvents and the like. The other components are not particularly restricted thereto. They can be appropriately used alone or in combination with two or more types thereof.

As examples of organic resins, mention may be made of polyvinyl alcohol, polyvinyl pyrrolidone, poly(alkyl acrylate) copolymers, and the like. The organic resin possesses a superior property of forming a film. For this reason, by blending the organic resin in the cosmetic for hair of the present invention, a strong coating film can be formed at the applied part, and durability such as sebum resistance and rub resistance or the like can be improved.

As examples of humectants, mention may be made of, for example, hyaluronic acid, chondroitin sulfate, pyrrolidone carboxylic acid salts, polyoxyethylene methylglucoside, polyoxypropylene methylglucoside, and the like. Needless to say, the aforementioned polyhydric alcohols exhibit a function of retaining moisture on the skin or hair.

As examples of the preservatives, mention may be made of, for example, alkyl paraoxybenzoates, benzoic acid, sodium benzoate, sorbic acid, potassium sorbate, phenoxyethanol and the like. As examples of the antimicrobial agents, mention may be made of benzoic acid, salicylic acid, carbolic acid, sorbic acid, alkyl paraoxybenzoates, parachloromethacresol, hexachlorophene, benzalkonium chloride, chlorhexidine chloride, trichlorocarbanilide, trichlosan, photosensitizers, isothiazolinone compounds such as 2-methyl-4-isothiazolin-3-one, 5-chloro-2-methyl-4-isothiazolin-3-one and the like, amine oxides such as dimethyl laurylamine oxide, dihydroxyethyl laurylamine oxide and the like, and the like.

In addition, as examples of anti-microbial agents, mention may be made of apolactoferrin; phenol-based compounds such as resorcinol; anti-microbial or fungicidal basic proteins or peptides such as iturin-based peptides, surfactin-based peptides, protamine or salts thereof (protamine sulfate and the like) and the like; polylysines such as $\epsilon$-polylysine or salts thereof, and the like; anti-microbial metal compounds which can produce a silver ion, a copper ion or the like; antimicrobial enzymes such as protease, lipase, oxydoreductase, carbohydrase, transferase, phytase and the like; and the like.

As examples of perfume, mention may be made of perfume extracted from flowers, seeds, leaves, and roots of various plants; perfume extracted from seaweeds; perfume extracted from various parts or secretion glands of animals such as musk and sperm oil; or artificially synthesized perfume such as menthol, musk, acetate, and vanilla. The conventional perfume can be selected and blended in an appropriate amount in accordance with the formulations of the cosmetics for hair in order to provide a certain aroma or scent to the cosmetics, or in order to mask unpleasant odor.

As examples of oxidants, mention may be made of, for example, hydrogen peroxide, peroxidized urea, alkali metal salts of bromic acid, and the like. As examples of antioxidants, mention may be made of, for example, tocopherol, butylhydroxyanisole, dibutylhydroxytoluene, phytic acid and the like. As the antioxidants, ascorbic acid and/or ascorbic acid derivatives may be used. As examples of ascorbic acid derivatives which can be used, mention may be made of, for example, sodium ascorbate, potassium ascorbate, calcium ascorbate, ammonium ascorbate, erythorbic acid, sodium erythorbate, sodium ascorbyl phosphate, ascorbyl citrate, ascorbyl acetate, ascorbyl tartarate, ascorbyl palmitate, ascorbyl stearate, ascorbyl glucoside and the like. In addition, as the antioxidants, the reductants may be used. For example, sulfurous acid, bisulfurous acid, thiosulfuric acid, thiolactic acid, thioglycolic acid, L-cysteine, N-acetyl-L-cysteine and salts thereof can be appropriately used.

As examples of pH adjusting agents, mention may be made of, for example, lactic acid, citric acid, glycolic acid, succinic acid, tartaric acid, dl-malic acid, potassium carbonate, sodium hydrogencarbonate, ammonium carbonate, ammonium hydrogencarbonate and the like. In addition, inorganic alkalized agents such as ammonia and the like, and organic alkalized agents such as isopropanolamine, monoethanolamine, diethanolamine, triethanolamine, 2-amino-2-methyl-1-propanolamine and the like can also be used. The blending amount of the pH adjustors is not particularly restricted, and may preferably range from 0.01% by weight (mass) to 20% by weight (mass) and more preferably range from 0.1% by weight (mass) to 10% by weight with respect to the total weight (mass) of the composition.

As examples of chelating agents, mention may be made of, for example, alanine, sodium edetate, sodium polyphosphate, sodium metaphosphate, phosphoric acid and the like.

As examples of algefacients, mention may be made of l-menthol, camphor and the like.

As examples of physiologically active components, mention may be made of, for example, vitamins, amino acids, nucleic acids, hormones, components extracted from natural vegetables, seaweed extracted components, herbal medicine components, whitening agents such as placenta extracts, arbutin, glutathione, saxifrageous extracts and the like; cell activators such as royal jelly, and the like; agents for ameliorating skin roughness; blood circulation accelerators such as nonylic acid vanillylamide, benzyl nicotinate, beta-butoxyethyl nicotinate, capsaicin, gingerone, cantharide tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; anti-inflammatory agents such as $\epsilon$-aminocaproic acid, glycyrrhizinic acid, $\beta$-glycyrrhetinic acid, lysozyme chloride, guaiazulene, hydrocortisone, allantoin, tranexamic acid, azulene and the like; and the like.

As examples of vitamins, mention may be made of vitamin As such as vitamin A oil, retinol, retinol acetate, retinol palmitate and the like; vitamin Bs such as vitamin B2s such as riboflavin, riboflavin butyrate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate and the like; pantothenic acids such as calcium pantothenate, D-pantothenyl alcohol, pantothenyl ethyl ether, acetyl pantothenyl ethyl ether and the like; and the like.

As examples of amino acids, mention may be made of glycine, valine, leucine, isoleucine, serine, threonine, phenylalanine, arginine, lysine, aspartic acid, glutamate, cystine, cysteine, methionine, tryptophan and the like.

As examples of nucleic acids, mention may be made of deoxyribonucleic acid and the like.

As examples of hormones, mention may be made of estradiol, ethenyl estradiol and the like.

Natural vegetable extracted components, seaweed extracted components and herbal medicine components are not particularly restricted, and one or more types of components having effects such as whitening effects, anti-ageing effects, effects of ameliorating ageing, effects of beautifying skin, anti-microbial effects, preservatives effects and the like can be preferably blended.

As detailed examples thereof, mention may be made of, for example, *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa* multiflora extract, *Echinacea angustifolia* leaf extract, *Scutellaria baicalensis* root extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extract, *Sasa veitchii* extract, *Sophora angustifolia* extract, walnut extract, grapefruit extract, *Clematis vitalba* leaf extract, chlorella extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis idaea* extract, *Asiasarum sieboldi* extract, *Bupleurum falcatum* extract, umbilical extract, *Salvia* extract, *Crocus sativus* flower extract, sasa bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriobotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma-jobi* seed extract, *Artemisia princeps* extract, lavender extract, apple extract, lettuce extract, lemon extract, *Astragalus sinicus* extract, rose extract, rosemary extract, *Roman chamomile* extract, royal jelly extract, and the like. The aforementioned extracts may be water-soluble or oil-soluble.

The cosmetic of the present invention may further comprise (I) water. Therefore, the cosmetic of the present invention can be in the form of an oil-in-water emulsion or a water-in-oil emulsion. In this case, the cosmetic of the present invention exhibits superior emulsion stability and a superior sensation during use.

Water is not particularly restricted as long as it does not include any harmful components for human bodies and is clean. As examples thereof, mention may be made of tap water, purified water, and mineral water. In addition, in the cosmetic for hair, and in particular, the cosmetic for hair in the form of an emulsion composition of the present invention, the blending amount of water preferably ranges from 2 to 98% by weight (mass), with respect to the total weight (mass) of the cosmetic.

In the cosmetic of the present invention, depending on the formulations and the purposes thereof, volatile solvents such as light isoparaffins, ethers, LPG, N-methylpyrrolidone, next-generation chlorofluorocarbons, and the like, can be blended in addition to water.

The aforementioned organopolysiloxane composition of the present invention may be blended in the cosmetic, as it is, or alternatively, may be blended therein as an emulsion obtained by using water and a surfactant of the aforementioned component (D) beforehand. In addition, an emulsion may be produced by using an oil agent of the aforementioned component (C) or a part thereof, water and the surfactant of the aforementioned component (D), in addition to the aforementioned organopolysiloxane composition of the present invention, and then the emulsion may be blended in a cosmetic. The form of the emulsion must be adapted to the form of the cosmetic to be blended. For example, in the case of a cosmetic in the form of an oil-in-water emulsion, if the same type of oil-in-water emulsion of the organopolysilicone composition is prepared, the emulsion can be blended in the cosmetic as it is. In this case, as the surfactant of the aforementioned component (D) used in the preparation for the emulsion of the organopolysiloxane composition of the present invention, an appropriate one is preferably selected in order to maintain stability of the blending system, and prevent from impairing feeling to the touch.

The cosmetic of the present invention may be an emulsion. In this case, the emulsion may be not only an oil-in-water emulsion or water-in-oil emulsion, but also a multiple emulsion or microemulsion thereof. The form of the emulsion (oil-in-water type or water-in-oil type) and the particle size of the emulsion can be appropriately selected or adjusted, in accordance with the types of the cosmetics.

In the case in which the cosmetic of the present invention is in the form of an oil-in-water emulsion, the dispersion phase of the aforementioned cosmetic is liquid particles obtained by emulsifying the aforementioned organopolysiloxane composition of the present invention or a mixture of the aforementioned (C) oil agent therewith by means of the surfactant of the aforementioned component (D). The average particle size thereof can be measured by a conventional measurement device using a laser diffraction/scattering method or the like. The cosmetic in the form of an oil-in-water emulsion may be a transparent microemulsion in which the average particle size of the dispersion phase measured is 0.1 µm or less, or may be a milky emulsion having a large particle size so that the average particle size exceeds 4 µm. In addition, in order to improve stability and transparency of the outer appearance of the emulsion, the emulsion particles can be miniaturized. In particular, in order to improve the adhesive property with respect to the hair or skin or a sensation during use, an emulsion having an average particle size ranging from 0.5 to 20 µm can be selected, and is preferable. For example, in the case of a microemulsion, stability is improved, and in the case of a cleansing cosmetic, foam quality is improved. In the case of a normal particle size ranging from submicrons to 4 µm, superior usability is exhibited, good balance between a blending effect and stability is exhibited, and preparation is easily carried out. In addition, in the case of a large particle size of several microns or more, and for example, ranging from 4 to 5 µm, improvements of adhesive properties to hair and a sensation during use may be expected.

The cosmetic of the present invention in the form of an oil-in-water emulsion or a water-in-oil emulsion can be produced by mixing components of the aforementioned cosmetic using a mechanical force by means of an apparatus such as a homomixer, a paddle mixer, a Henschel mixer, a homodisper, a colloid mill, a propeller stirrer, a homogenizer, an in-line type continuous emulsifier, an ultrasonic emulsifier, a vacuum kneader or the like.

The cosmetic of the present invention in the form of an emulsion comprises the organopolysiloxane composition of the present invention as an essential component. For this reason, a superior sensation during use can be exhibited although the cosmetic has a dispersion phase. In addition, inside of the dispersion phase is uniform, and superior stability is exhibited.

The cosmetics of the present invention can comprise any combinations of the aforementioned all components, if necessary, as long as the cosmetics comprise the aforementioned liquid organopolysiloxane. Namely, the cosmetics of the present invention can comprise any combinations of components (C) to (H) as described below, together with the aforementioned liquid organopolysiloxane composition.

(C) Oil agents
(D) Surfactants
(E) Alcohols
(F) Thickening and/or gelling agents
(G) Powders and/or coloring agents
(H) UV-ray protective components Among the combinations of components (C) to (H), combinations of the components preferably used in the present invention are described below.

(C)+{at least one selected from the group consisting of (D), (E), (F), (G) and (H)};
(C)+(D)+{at least one selected from the group consisting of (E), (F), (G) and (H)};
(C)+(D)+(E)+{at least one selected from the group consisting of (F), (G) and (H)};
(C)+(D)+(F)+{at least one selected from the group consisting of (E), (G) and (H)};
(C)+(D)+(G)+{at least one selected from the group consisting of (E), (F) and (H)};
(C)+(D)+(H)+{at least one selected from the group consisting of (E), (F) and (G)};
(C)+(D)+(E)+(F)+{(G) or (H)};
(C)+(E)+{at least one selected from the group consisting of (D), (F), (G) and (H)};
(C)+(E)+(F)+{at least one selected from the group consisting of (D), (G) and (H)};
(C)+(E)+(G)+{at least one selected from the group consisting of (D), (F) and (H)};
(C)+(E)+(H)+{at least one selected from the group consisting of (D), (F) and (G)};
(C)+(F)+{at least one selected from the group consisting of (D), (E), (G) and (H)};
(C)+(F)+(G)+{at least one selected from the group consisting of (D), (E) and (H)};
(C)+(F)+(H)+{at least one selected from the group consisting of (D), (E) and (G)};
(C)+(G)+{at least one selected from the group consisting of (D), (E), (F) and (H)}; and
(C)+(G)+(H)+{at least one selected from the group consisting of (D), (E) and (F)}.

The cosmetics of the present invention generally comprise water.

The forms of the cosmetics of the present invention are not particularly restricted, and may be in the form of liquids, creams, solids, pastes, gels, powders, lamellas, mousses, sprays, sheets, and the like, in addition to emulsions.

The cosmetic compositions of the present invention can be used in cosmetics for skin such as skin cleansing products, skin care products, makeup products, antiperspirant products, deodorant products, UV protective products and the like; cosmetics for hair such as hair cleansing products, hair styling products, hair coloring products, hair tonic products, hair rinse products, hair conditioning products, hair treatment products, and the like; and products for use in bathing, and the like. In particular, the cosmetic of the present invention are preferably used in skin care products, hair products, antiperspirant products, deodorant products, makeup products or UV protective products.

The aforementioned cosmetic for skin may be used at any part of the scalp, face including lips, eyebrows, and cheek, fingers, nails, and entire bodies. More particularly, as examples thereof, mention may be made of a skin cleansing product such as cleansing gel, cleansing cream, cleansing foam, cleansing milk, cleansing lotion, face cleansing cream, eye markup remover, face cleansing foam, liquid soap for use on entire bodies, hand soap, gel soap, solid soap, facial rinse, body rinse, shaving cream, enamel remover, cosmetic against acne or the like; a skin care product such as skin cream, scalp treatment, skin milk, milky lotion, emulsion, cosmetic lotion, humectant, serum, facial mask, body powder, essence, shaving lotion, a composition for use during massaging or the like; a makeup cosmetic such as foundation, makeup base, finishing powder, face powder, lipstick, lip cream, lip paste, lip gloss, eye shadow, eyeliner, eye cream, eyebrow pencil, cosmetic for eyelashes, eyebrow brush, mascara, blusher, cheek cosmetic such as cheek color or cheek rouge, manicure, pedicure, nail color, nail lacquer, enamel remover, nail polish or the like; an antiperspirant product such as deodorant or the like; and a product for controlling UV rays such as sun screening preparation, preparation for sunburn (suntan preparation) or the like.

As examples of the aforementioned cosmetics for hair, mention may be made of a hair cleansing preparation such as shampoo, rinse-in-shampoo or the like; a hair styling product such as hair oil, hair curl retaining preparation, setting preparation, hair cream, hair spray, hair liquid, hair wax or the like; a coloring product for hair such as hair dye composition, hair color spray, hair color rinse, hair color stick, or the like; pilatory product such as hair tonic, hair treatment, hair pack or the like; a hair rinse or conditioner product such as oil rinse, cream rinse, treatment rinse, hair conditioner, hair treatment, or the like. In addition, as examples of the aforementioned cosmetics for bathing, mention may be made of bath oil, bath salts, and bath foam.

A container for housing the aforementioned cosmetic is not particularly restricted. As examples thereof, mention may be made of a jar, a pump, a tube, a bottle, a pressurized can discharging container, a pressure tight aerosol container, a light shield container, a compact container, a metal dish, a stick container, a bringing up container, a spray container, a container with partitions, equipped with a mixture discharging port, and the like. In the case of the tube, separation may easily occur in a common silicone-based preparation. In contrast, in the cosmetics of the present invention, tendency of the phase separation is controlled, and superior stability are exhibited. Therefore, there is an advantage in that even if the cosmetics of the present invention are filled in the aforementioned tube containers, the cosmetics can be stably stored.

EXAMPLES

Hereinafter, the present invention is described in detail with reference to examples. It should be understood that the present invention is not restricted to the examples. In the composition formulae described below, an $Me_3SiO$ group (or a $Me_3Si$ group) is indicated as "M", and an $Me_2SiO$ group is indicated as "D", and units in which a methyl group (Me) in M and D is modified by any substituent are respectively indicated as "$M^R$" and "$D^R$". For example, in the case of replacing a methyl group in M and D with a hydrogen atom or a vinyl group, they are respectively indicated as "$M^H$" and "$D^H$", or "$M^{Vi}$" and "$D^{Vi}$".

"Fluidity", "loss factor" and "complex viscosity" used below were measured as follows.

Figure 4:
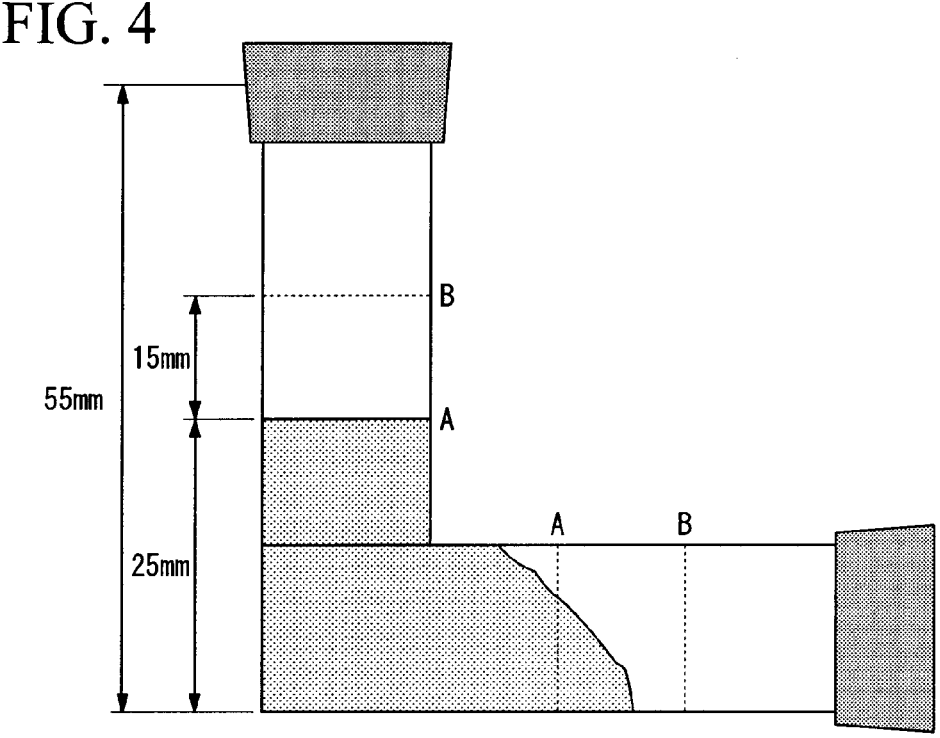
FIG. 4 shows a drawing showing a method for measuring fluidity in the examples.

Fluidity
As shown in FIG. 4, a screw tube (laboran screw tube bottle No. 5, manufactured by AS ONE Corporation) with a volume of 20 mL, having marked lines (hereinafter, "A line" and "B line") at the heights of 25 mm and 40 mm from the bottom of the tube was prepared, and a sample was placed therein to the A line. Subsequently, the tube was hermetically sealed and stored for 24 hours in a thermostatic chamber at 25° C. At 25° C., the aforementioned screw tube was horizontally laid. The sample in which a period until the tip of the sample reached the B line was within 96 hours was evaluated as "liquid".

Loss Factor
A loss factor, tan δ, was measured by means of an ARES viscoelasticity measurement apparatus (manufactured by Reometric Scientific Inc.). The measurement conditions were 25° C., 40 mm parallel plate, gap 0.5 mm, strain 10%, and frequency 10 Hz.

Complex Viscosity
A complex viscosity was measured by means of an ARES viscoelasticity measurement apparatus (manufactured by Reometric Scientific Inc.). The measurement conditions were 25° C., 40 mm parallel plate, gap 0.5 mm, strain 10%, and frequency 10 Hz.

Synthesis Example 1

Synthesis of Silicone Compound No. 1

0.26 parts by weight (mass) of a methylhydrogenpolysiloxane represented by the following average composition formula: $M-D_3-D^H_5-M$, 7.50 parts by weight (mass) of a methylhydrogenpolysiloxane represented by the following average composition formula: $M^H-D_{17}-M^H$, 92.24 parts by weight (mass) of a methylvinylpolysiloxane represented by the following average composition formula: $M^{Vi}-D_{150}-M^{Vi}$, and 300 parts by weight (mass) of a decamethylpentacyclosiloxane (SH 245, manufactured by Dow Corning Toray Co., Ltd.) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 100° C. to 120° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 1.9, and the complex viscosity was 123,600 mPa·s.

Synthesis Example 2

Synthesis of Silicone Compound No. 2

0.69 parts by weight (mass) of a methylhydrogenpolysiloxane represented by the following average composition formula: $M-D_3-D^H_5-M$, 99.12 parts by weight (mass) of a methylvinylpolysiloxane represented by the following average composition formula: $M^{Vi}-D_{150}-M^{Vi}$, and 25 parts by weight (mass) of a decamethylpentacyclosiloxane (SH 245, manufactured by Dow Corning Toray Co., Ltd.) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 100° C. to 120° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 3.4, and the complex viscosity was 6,410 mPa·s.

Synthesis Example 3

Synthesis of Silicone Compound No. 3

7.2 parts by weight (mass) of 1-dodecene, 9.8 parts by weight (mass) of a methylhydrogenpolysiloxane represented by the following average composition formula: $M$-$D_3$-$D^H_5$-$M$, 83.0 parts by weight (mass) of a methylvinylpolysiloxane represented by the following average composition formula: $M^{Vi}$-$D_{40}$-$M^{Vi}$, and 100 parts by weight (mass) of a decamethylpentacyclosiloxane (SH 245, manufactured by Dow Corning Toray Co., Ltd.) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 1.7, and the complex viscosity was 8,950 mPa·s.

Synthesis Example 4

Synthesis of Silicone Compound No. 4

7.2 parts by weight (mass) of 1-hexadecene, 5.5 parts by weight (mass) of a methylhydrogenpolysiloxane represented by the following average composition formula: $M$-$D_3$-$D^H_5$-$M$, 87.3 parts by weight (mass) of a methylvinylpolysiloxane represented by the following average composition formula: $M^{Vi}$-$D_{40}$-$M^{Vi}$, and 100 parts by weight (mass) of a decamethylpentacyclosiloxane (SH 245, manufactured by Dow Corning Toray Co., Ltd.) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was stirred while the inner temperature was maintained at 70° C. to 90° C. Subsequently, 87.3 parts by weight (mass) of a methylvinylpolysiloxane represented by the following average composition formula: $M^{Vi}$-$D_{40}$-$M^{Vi}$ was placed therein, and the mixture was stirred under a nitrogen atmosphere until a uniform mixture was obtained. Subsequently, the mixture was allowed to stand for 2 hours at the inner temperature ranging from 70° C. to 90° C. The reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 8.7, and the complex viscosity was 230 mPa·s.

Synthesis Example 5

Synthesis of Silicone Compound No. 5

43.3 parts by weight (mass) of a methylhydrogenpolysiloxane represented by the following average composition formula: $M$-$D_{55}$-$D^H_7$-$M$, 15.7 parts by weight (mass) of a methylvinylpolysiloxane represented by the following average composition formula: $M^{Vi}$-$D_{150}$-$M^{Vi}$ were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was slowly stirred while the inner temperature was maintained at 40° C. After it was confirmed that a change in viscosity was not observed and the reaction was completed, 41.0 parts by weight (mass) of an allylpolyoxyalkylene represented by an average composition formula: $C_3H_5[OC_2H_4]_{11}OCH_3$ was placed therein, and stirred for 2 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 3.0, and the complex viscosity was 16,000 mPa·s.

Synthesis Example 6

Synthesis of Silicone Compound No. 6

66.3 parts by weight (mass) of a methylhydrogenpolysiloxane represented by the following average composition formula: $M$-$D_{170}$-$D^{R*1}_{21}$-$D^H_2$-$M$, $D^{R*1}$ representing an allylpolyoxyalkylene residue represented by an average composition formula: $—C_3H_6[OC_2H_4]_{18}[OC_3H_6]_{18}OH$, 8.5 parts by weight (mass) of a methylvinylpolysiloxane represented by the following average composition formula: $M^{Vi}$-$D_{150}$-$M^{Vi}$, and 20 parts by weight (mass) of toluene were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was stirred for 2 hours at the inner temperature ranging from 70° C. to 90° C. In addition, 25.2 parts by weight (mass) of an allylpolyoxyalkylene represented by an average composition formula: $C_3H_5[OC_2H_4]_{18}[OC_3H_6]_{18}OH$ was placed therein, and stirred for 2 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, turbid crosslinked organopolysiloxane was obtained. The fluidity of the obtained crosslinked organopolysiloxane was "liquid", the loss factor (tan δ) was 5.4, and the complex viscosity was 12,600 mPa·s.

Synthesis Example 7

Synthesis of Silicone Compound No. 7

1.0 part by weight (mass) of a methylhydrogenpolysiloxane represented by the following average composition formula: $M$-$D_{6.7}$-$D^H_{2.8}$-$M$, 49.0 parts by weight (mass) of a polysiloxane copolymer having an alkenyl group, represented by the following average composition formula: $C_6H_{11}$-$D_{40}$-$C_6H_{12}$-$D_{40}$-$C_6H_{11}$, and 50 parts by weight (mass) of a decamethylpentacyclosiloxane (SH 245, manufactured by Dow Corning Toray Co., Ltd.) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 8.0, and the complex viscosity was 7,210 mPa·s.

Synthesis Example 8

Synthesis of Silicone Compound No. 8

67.7 parts by weight (mass) of a methylhydrogenpolysiloxane represented by the following average composition formula: $M\text{-}D_{13}\text{-}D^H_{5.5}\text{-}M$, 32.3 parts by weight (mass) of 1,5-hexadiene, and 100 parts by weight (mass) of hydrogenated polyisobutene (PARLEAM (trade name) 4, manufactured by NOF Corporation) were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 9.0, and the complex viscosity was 2,130 mPa·s.

Synthesis Example 9

Synthesis of Silicone Compound No. 9

14.9 parts by weight (mass) of a methylhydrogenpolysiloxane represented by the following average composition formula: $M\text{-}D_{13}\text{-}D^H_{5.5}\text{-}M$, 85.1 parts by weight (mass) of a dimethallylpolyoxyalkylene represented by an average composition formula: $C_4H_7[OC_2H_4]_{10}[OC_3H_6]_{7.6}OC_4H_7$, and 200 parts by weight (mass) of toluene were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was allowed to stand for 3 hours at the inner temperature ranging from 70° C. to 90° C. The disappearance of the Si—H bond was confirmed by IR spectrum, and the development of the reaction was confirmed. Subsequently, the reaction mixture was heated under reduced pressure to remove components with low boiling points. Thereby, a pale yellow, transparent crosslinked organopolysiloxane was obtained. The fluidity of the obtained crosslinked organopolysiloxane was "liquid", the loss factor (tan δ) was 1.9, and the complex viscosity was 7,510 mPa·s.

Comparative Synthesis Example 1

Synthesis of Silicone Compound RE 1

69.2 parts by weight (mass) of a methylhydrogenpolysiloxane represented by the following average composition formula: $M\text{-}D_{40}\text{-}D^H_2\text{-}M$, 20.8 parts by weight (mass) of a methylvinylpolysiloxane represented by the following average composition formula: $M^{Vi}\text{-}D_{10}\text{-}M^{Vi}$ were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was stirred for one hour at the inner temperature of 80° C. The obtained product in the form of a gel was pulverized and kneaded under shearing force. Thereby, a pale yellow, translucent crosslinked organopolysiloxane in the form of a gel was obtained. The fluidity of the obtained crosslinked organopolysiloxane was not "liquid", the loss factor (tan δ) was 0.2, and the complex viscosity was 28,890 mPa·s.

Comparative Synthesis Example 2

Synthesis of Silicone Compound RE 2

12.5 parts by weight (mass) of a methylhydrogenpolysiloxane represented by the following average composition formula: $M\text{-}D_{94}\text{-}D^H_6\text{-}M$, and 1.0 part by weight (mass) of 1,5-hexadiene were placed in a reactor, and the mixture was stirred under a nitrogen atmosphere until a uniform mixture was obtained. Subsequently, 0.004 parts by weight (mass) of a platinum catalyst was added thereto and stirred until a uniform mixture was obtained. Subsequently, the mixture was stirred for one hour at the inner temperature of 80° C. The obtained product in the form of a gel was kneaded under shearing force. Thereby, a pale yellow, translucent crosslinked organopolysiloxane in the form of a gel was obtained. The fluidity of the obtained crosslinked organopolysiloxane was not "liquid", the loss factor (tan δ) was 0.1, and the complex viscosity was 104,600 mPa·s.

Figure 5:
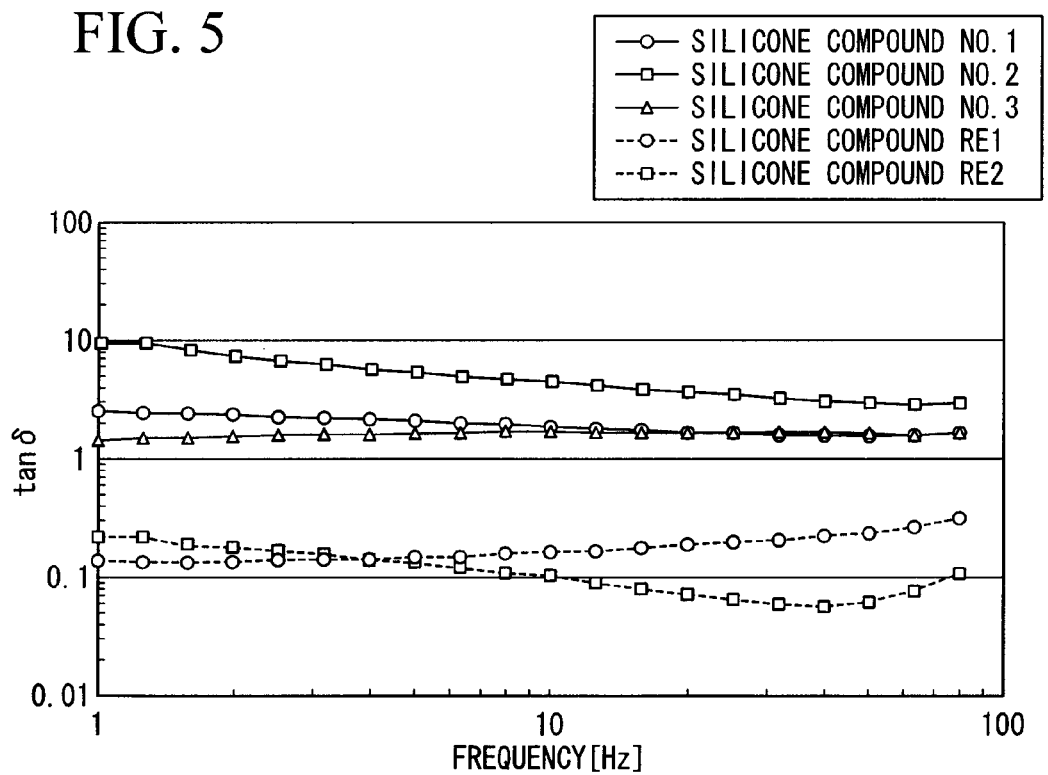
FIG. 5 shows a graph showing the relationship between the frequency and the loss factor (tan δa) of Silicone Compounds Nos. 1 to 3, Silicone Compound RE 1 and Silicone Compound RE 2.
Figure 6:
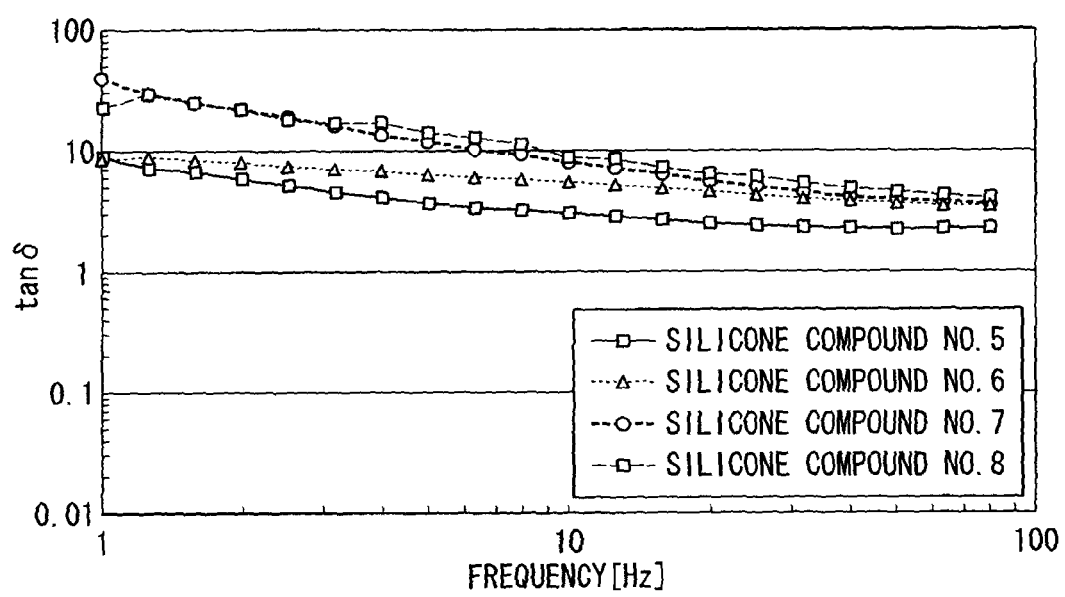
FIG. 6 shows a graph showing the relationship between the frequency and the loss factor (tan δa) of Silicone Compounds Nos. 5 to 8.

The average composition formulae, representative physical property values, feeling to the touch and impression at the time of application to the skin of "Silicone Compound No. 1" to "Silicone Compound No. 9", "Silicone Compound RE 1" and "Silicone Compound RE 2" are shown in Table 1. Furthermore, the relationship between the frequency and the loss factor (tan δa) is shown in FIGS. 5 and 6.

TABLE 1

| Silicone Compound | Average composition formula of main chain | Outer appearance | tan δ | Feeling to the touch and impression |
|---|---|---|---|---|
| Silicone Compound No. 1 | $M\text{—}D_3\text{—}D^{Link}_5\text{—}M$<br>Link = $M^{Vi}\text{—}D_{150}(\text{—}X\text{—}D_{17}\text{—}X\text{—}D_{150})_2\text{—}M^{Vi}$<br>X = $M\text{—}C_2H_4\text{—}M$ | Pale yellow, transparent liquid | 1.9 | At the time of applying on the skin, the product was softer than a gum or gel, provided a natural film-forming sensation with an elastic sensation, and a thermal sensation. |

TABLE 1-continued

| Silicone Compound | Average composition formula of main chain | Outer appearance | tan δ | Feeling to the touch and impression |
|---|---|---|---|---|
| Silicone Compound No. 2 | $M-D_3-D^{Link}_5-M$<br>$LINK = M^{Vi}-D_{150}-M^{Vi}$ | Pale yellow, transparent liquid | 3.4 | At the time of applying on the skin, the product provided a natural film-forming sensation with an elastic sensation, in addition to softness, and a thermal sensation. A uniform sensation was exhibited, and good compatibility with the skin was provided. |
| Silicone Compound No. 3 | $M-D_3-D^{Link}_2-D^{R1}_3-M$<br>$Link = M^{C2H4}-D_{40}-M^{C2H4}$<br>$R1 = C_{12}H_{25}$ | Pale yellow, transparent liquid | 1.7 | At the time of applying on the skin, the product provided a good spreading property, a natural film-forming sensation with an elastic sensation, in addition to softness, and a thermal sensation. A uniform sensation was exhibited, and good compatibility with the skin was provided. |
| Silicone Compound No. 4 | $M-D_3-D^{Link}_1-D^{R1}_4-M$<br>$Link = M^{C2H4}-D_{40}-M^{C2H4}$<br>$R1 = C_{16}H_{33}$ | Pale yellow, transparent liquid | 8.7 | At the time of applying on the skin, the product provided a good spreading property, a natural film-forming sensation with an elastic sensation, in addition to softness, and a thermal sensation. A uniform sensation was exhibited, and good compatibility with the skin was provided. A slight glossy sensation was exhibited. |
| Silicone Compound No. 5 | $M-D_{55}-D^{Link}_{0.3}-D^{R1}_{6.7}-M$<br>$Link = M^{C2H4}-D_{40}-M^{C2H4}$<br>$R1 = C_3H_6[OC_2H_4]_{11}OCH_3$ | Pale yellow, transparent liquid | 3.0 | At the time of applying on the skin, the product provided a good spreading property, a natural film-forming sensation with an elastic sensation, in addition to softness, and a thermal sensation. A uniform sensation was exhibited, and good compatibility with the skin was provided. A moisturizing sensation was exhibited. |
| Silicone Compound No. 6 | $M-D_{170}-D^{Link}_{1.2}-D^{R*1}_{21.8}-M$<br>$Link = M^{C2H4}-D_{150}-M^{C2H4}$<br>$R1 = C_3H_6[OC_2H_4]_{18}[OC_3H_6]_{18}OH$ | Pale yellow, transparent liquid | 5.4 | At the time of applying on the skin, the product provided a good spreading property, a natural film-forming sensation with an elastic sensation, in addition to softness, and a thermal sensation. A uniform sensation was exhibited, and good compatibility with the skin was provided. A moisturizing sensation was exhibited. |
| Silicone Compound No. 7 | $M-D_{6.7}-D^{Link}_{2.8}-M$<br>$Link = C_6H_{12}-D_{40}-C_6H_{12}-D_{40}-C_6H_{12}$ | Pale yellow, transparent liquid | 8.0 | At the time of applying on the skin, the product provided a good spreading property, a natural film-forming sensation with an elastic sensation, in addition to softness, and a thermal sensation. A uniform sensation was exhibited, and good compatibility with the skin was provided. A slight glossy sensation was exhibited. |
| Silicone Compound No. 8 | $M-D_{13}-D^{Link}_{5.5}-M$<br>$Link = C_6H_{12}$ | Pale yellow, transparent liquid | 9.0 | At the time of applying on the skin, the product provided a good spreading property, a natural film-forming sensation with an elastic sensation, in addition to softness, and a thermal sensation. A uniform sensation was exhibited, and good compatibility with the skin was provided. A slight glossy sensation was exhibited. |
| Silicone Compound No. 9 | $M-D_{13}-D^{Link}_{5.5}-M$<br>$Link = C_4H_8[OC_2H_4]_{10}[OC_3H_6]_{7.6}OC_4H_8$ | Pale yellow, transparent liquid | 1.9 | At the time of applying on the skin, the product provided a good spreading property, a natural film-forming sensation with an elastic sensation, in addition to softness, and a thermal sensation. A uniform sensation was exhibited, and good compatibility with the skin was provided. A moisturizing sensation was exhibited. |
| Silicone Compound RE 1 | $M-D_{40}-D^{Link}_2-M$<br>$Link = M^{C2H4}-D_{10}-M^{C2H4}$ | Pale yellow, translucent gel | 0.2 | Even if spreading the product to the skin was tried, deviation of the non-uniform gel was observed, and a poor spreading property was exhibited. A thinly spread part of the product on the skin exhibited a strong non-smooth sensation, and a poor adhesive sensation with the skin was exhibited. An unnatural texture with a sensation of pressure was strongly exhibited. |

TABLE 1-continued

| Silicone Compound | Average composition formula of main chain | Outer appearance | tan δ | Feeling to the touch and impression |
|---|---|---|---|---|
| Silicone Compound RE 2 | M—$D_{94}$—$D^{Link}_{6}$—M LINK = $C_6H_{12}$ | Pale yellow, translucent gel | 0.1 | Even if spreading the product to the skin was tried, deviation of the non-uniform gel was observed, and a poor spreading property was exhibited. A poor adhesive sensation with the skin, and an unnatural texture with a sensation of pressure were strongly exhibited. |

Figure 2:
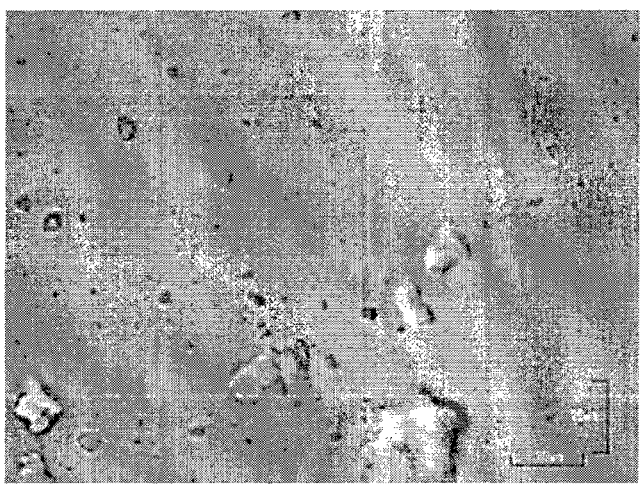
FIG. 2 shows an electron microscope photograph of a mixture of Silicone Compound RE 1 and decamethylpentacyclosiloxane (D5) (mixing ratio=2:8 (D5)).
Figure 3:
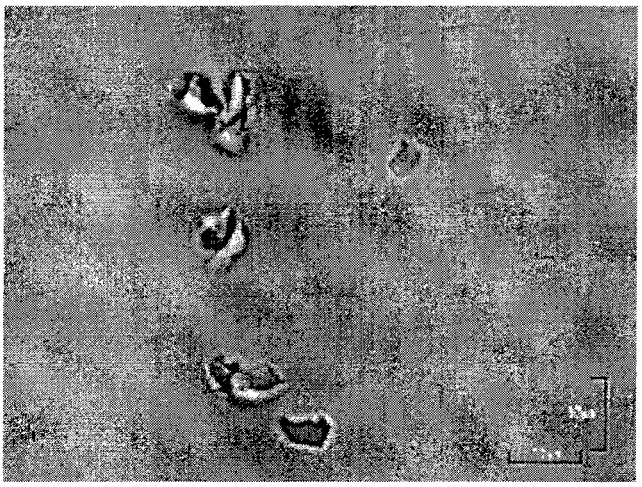
FIG. 3 shows an electron microscope photograph of a mixture of Silicone Compound RE 2 and decamethylpentacyclosiloxane (D5) (mixing ratio=2:8 (D5)).

Next, microscope photographs of mixtures obtained by mixing each of Silicone Compound No. 1, Silicone Compound RE 1 and Silicone Compound RE 2 with decamethylpentacyclosiloxane (D5) (mixing ratio=2:8 (O5)) are respectively shown in FIG. 1 to FIG. 3.

As shown in FIG. 1, Silicone Compound No. 1 has a low degree of crosslinking, and for this reason, Silicone Compound No. 1 is mixed with an oil agent well, and a uniform oil phase can be formed. In contrast, in Silicone Compound RE 1 and Silicone Compound RE 2, gel particles are present in the oil phase, and for this reason, the oil phases are not uniform as shown in FIG. 2 and FIG. 3.

Next, presence or absence of particles in each of the aforementioned mixtures was measured at 25° C. by means of monodispersion mode analysis using an analyzer for submicron particles (COULTER MODEL N4 MD, manufactured by Coulter Electronics Ltd.). In addition average particle size of the emulsion particles was measured by means of a dynamic optical diffusion method. The results are shown in Table 2.

TABLE 2

|  | Silicone Compound No. 1 | Silicone Compound RE 1 | Silicone Compound RE 2 |
|---|---|---|---|
| Average particle size | No particle | 3 μm or more | 3 μm or more |

Evaluation for Feeling to the Touch

Examples 1 and 2 and Comparative Examples 1 to 4

Feeling to the touch of each of compositions obtained by mixing and uniformizing components 1 to 7 shown in Table 3 by means of a dental mixer (MIGMA, manufactured by MIKRONA) was evaluated. In order to secure the objectivity, a smoothing sensation and an adhesive sensation were evaluated on the basis of the evaluation criteria described below. The results are shown in Table 3. In the table, "parts" indicates "parts by weight (mass)".

Evaluation Criteria

A composition to be evaluated was applied on the arm of each of 10 panelists. At the start of the application of the composition, and at the completion of the application in which the panelist felt that the composition was sufficiently applied, a natural smoothing sensation (natural feeling to the touch without roughness, a tensile sensation, or an unpleasant sensation) and an adhesion sensation to the skin were evaluated. Each panelist answered a questionnaire on each evaluation category. In the case of the evaluation category evaluated as superiority by the panelist, 5 points were given, and in the case of the evaluation category evaluated as inferiority by the panelist, 1 point was given. In the case of the evaluation category evaluated as interlevels by the panelist, 2, 3, or 4 points were given. The average points obtained thereby were used as evaluation results of the sensation during use.

TABLE 3

| No. | Component | Example 1 | Example 2 | Comparative Example 1 | Comparative Example 2 | Comparative Example 3 | Comparative Example 4 |
|---|---|---|---|---|---|---|---|
| 1 | Silicone Compound No. 1 | 20 | — | — | — | — | — |
| 2 | Silicone Compound No. 2 | — | 20 | — | — | — | — |
| 3 | Silicone Compound RE 1 | — | — | 20 | — | — | — |
| 4 | Silicone Compound RE 2 | — | — | — | 20 | — | — |
| 5 | Silicone gum*[1] | — | — | — | — | 20 | — |
| 6 | Dimethicone (100 mm²/s)*[2] | — | — | — | — | — | 20 |
| 7 | Decamethylcyclopentasiloxane*[3] | 80 | 80 | 80 | 80 | 80 | 80 |

| Evaluation category | | Evaluation results (points) | | | | | |
|---|---|---|---|---|---|---|---|
| Natural smoothing sensation | At the start of application | 4.8 | 4.5 | 4.0 | 3.6 | 4.4 | 2.9 |
| | At the completion of application | 4.4 | 4.2 | 2.8 | 2.7 | 2.9 | 2.5 |
| Adhesion sensation to the skin | At the start of application | 4.5 | 4.3 | 4.2 | 4.1 | 3.6 | 2.4 |
| | At the completion of application | 4.1 | 4.4 | 2.0 | 2.1 | 1.7 | 2.1 |

*[1]Product name: SGM 36 (manufactured by Dow Corning Toray Co., Ltd.)
*[2]Product name: SH 200-100 cs (manufactured by Dow Corning Toray Co., Ltd.)
*[3]Product name: SH 245 (manufactured by Dow Corning Toray Co., Ltd.)

As shown in Table 3, the mixture of Silicone Compound No. 1 or Silicone Compound No. 2 and decamethylpentacyclosiloxane exhibited both a good natural smoothing sensation and a good adhesion sensation to the skin. In contrast, the mixture of Silicone Compound RE 1 or Silicone Compound RE 2 and decamethylpentacyclosiloxane exhibited a strong rough sensation and a poor adhesion sensation to the skin at the completion of the application, and an unnatural texture with a sensation of pressure was strongly imparted. In addition, the mixture of the silicone gum having no crosslinking structure (Comparative Example 3) or dimethicone (Comparative Example 4) and decamethylpentacyclosiloxane exhibited a poor compatibility with respect to the skin since the mixture was diffused at the time of application, and a natural smooth sensation after the completion of the application was hardly imparted.

Examples 3 to 5 and Comparative Examples 5 to 8

W/O emulsion liquid foundations were prepared with the compositions shown in Table 4, and cosmetic properties thereof were functionally evaluated. Each of the evaluation categories in the functional tests was evaluated on the basis of the following evaluation criteria in order to ensure objectivity. The results are shown in Table 4. In the table, "parts" indicates "parts by weight (mass)".

Evaluation Criteria

A composition to be evaluated was applied on the arm of each of 10 panelists. At the start of the application of the composition, a natural smoothing sensation (natural feeling to the touch without roughness, a tensile sensation, or an unpleasant sensation), a spreading property on the skin, an adhesion sensation to the skin, absence of stickiness (absence of a sticky sensation when the application part was contacted with fingers at the completion of the application), and softness of the film (softness or a following property to the skin when the application part was contacted by fingers at the completion of the application) were evaluated. In addition, cosmetic durability was evaluated 6 hours after the completion of the application (under usual living conditions). Each panelist answered a questionnaire on each evaluation category. In the case of the evaluation category evaluated as superiority by the panelist, 5 points were given, and in the case of the evaluation category evaluated as inferiority by the panelist, 1 point was given. In the case of the evaluation category evaluated as interlevels by the panelist, 2, 3, or 4 points were given. The average points obtained thereby were used as evaluation results of the sensation during use.

TABLE 4

| No. | Component | Example | | | Comparative Example | | | |
|---|---|---|---|---|---|---|---|---|
| | | 3 | 4 | 5 | 5 | 6 | 7 | 8 |
| 1 | Copolymer of dimethylpolysiloxane and polyoxyalkylene*[1] | 2.0 | 2.0 | 2.0 | 2.0 | 2.0 | 2.0 | 2.0 |
| 2 | Dimethylpolysiloxane*[2] | 15.0 | 15.0 | 15.0 | 15.0 | 15.0 | 15.0 | 15.0 |
| 3 | Decamethylcyclopentasiloxane | 10.0 | 10.0 | 10.0 | 10.0 | 10.0 | 10.0 | 10.0 |
| 4 | Silicone Compound No. 1 | 6.5 | — | — | — | — | — | — |
| 5 | Silicone Compound No. 3 | — | 6.5 | — | — | — | — | — |
| 6 | Silicone Compound No. 7 | — | — | 6.5 | — | — | — | — |
| 7 | Silicone Compound RE 1 | — | — | — | 6.5 | — | — | — |
| 8 | Silicone Compound RE 2 | — | — | — | — | 6.5 | — | — |
| 9 | Silicone gum*[4] | — | — | — | — | — | 6.5 | — |
| 10 | Dimethicone*[5] (100 mm$^2$/s) | — | — | — | — | — | — | 6.5 |
| 11 | Silicone-treated titanium oxide | 1.2 | 1.2 | 1.2 | 1.2 | 1.2 | 1.2 | 1.2 |
| 12 | Octylsilane-treated yellow iron oxide | 0.1 | 0.1 | 0.1 | 0.1 | 0.1 | 0.1 | 0.1 |
| 13 | Octylsilane-treated red iron oxide | 0.08 | 0.08 | 0.08 | 0.08 | 0.08 | 0.08 | 0.08 |
| 14 | Octylsilane-treated black iron oxide | 0.02 | 0.02 | 0.02 | 0.02 | 0.02 | 0.02 | 0.02 |
| 15 | Silicone-treated sericite | 3.6 | 3.6 | 3.6 | 3.6 | 3.6 | 3.6 | 3.6 |
| 16 | Silicone-treated mica | 5.0 | 5.0 | 5.0 | 5.0 | 5.0 | 5.0 | 5.0 |
| 17 | Octylsilane-treated talc | 5.0 | 5.0 | 5.0 | 5.0 | 5.0 | 5.0 | 5.0 |
| 18 | Silicone-treated microparticulate titanium oxide | 2.0 | 2.0 | 2.0 | 2.0 | 2.0 | 2.0 | 2.0 |
| 19 | Silicone-treated microparticulate zinc oxide | 3.0 | 3.0 | 3.0 | 3.0 | 3.0 | 3.0 | 3.0 |
| 20 | Ethanol | 5.0 | 5.0 | 5.0 | 5.0 | 5.0 | 5.0 | 5.0 |
| 21 | Magnesium sulfate | 1.0 | 1.0 | 1.0 | 1.0 | 1.0 | 1.0 | 1.0 |
| 22 | Glycerol | 2.0 | 2.0 | 2.0 | 2.0 | 2.0 | 2.0 | 2.0 |
| 23 | Purified water | 38.5 | 38.5 | 38.5 | 38.5 | 38.5 | 38.5 | 38.5 |
| | Total parts | 100.0 | 100.0 | 100.0 | 100.0 | 100.0 | 100.0 | 100.0 |
| | Evaluation category | Evaluation results (points) | | | | | | |
| | Natural smoothing sensation at the start of the application | 4.0 | 4.6 | 4.8 | 1.5 | 1.3 | 3.5 | 2.1 |

TABLE 4-continued

|  |  | Example | | | Comparative Example | | | |
| --- | --- | --- | --- | --- | --- | --- | --- | --- |
| No. | Component | 3 | 4 | 5 | 5 | 6 | 7 | 8 |
|  | Spreading property on skin | 4.7 | 4.5 | 4.4 | 1.6 | 1.5 | 4.0 | 3.7 |
|  | Adhesion sensation to skin | 4.2 | 4.4 | 4.4 | 3.9 | 4.0 | 2.9 | 1.7 |
|  | Absence of stickiness | 4.0 | 4.7 | 4.5 | 1.3 | 1.5 | 2.7 | 3.8 |
|  | Softness of the film | 4.0 | 4.2 | 4.6 | 2.0 | 1.2 | 3.8 | 2.8 |
|  | Cosmetic durability | 4.0 | 4.4 | 4.3 | 3.9 | 4.0 | 2.6 | 1.2 |

[1] Product name: SS-2910 (manufactured by Dow Corning Toray Co., Ltd.)
[2] Product name: SH 200-6 cs (manufactured by Dow Corning Toray Co., Ltd.)
[3] Product name: SH 245 (manufactured by Dow Corning Toray Co., Ltd.)
[4] Product name: SGM 36 (manufactured by Dow Corning Toray Co., Ltd.)
[5] Product name: SH 200-100 cs (manufactured by Dow Corning Toray Co., Ltd.)

Preparation Method for W/O Emulsion Liquid Foundation

A mixture obtained by mixing and pulverizing Components 11 to 19 beforehand was added to an oil phase obtained by mixing Components 1 to 10 at room temperature, followed by dispersing them by means of a disper. A mixture obtained by mixing Components 20 to 23 which were aqueous phase components was added thereto while stirring, to emulsify the mixture. Thereby, a W/O emulsion liquid foundation was prepared.

The W/O emulsion liquid foundations in accordance with Examples 3 to 5 strongly provided a natural smoothing sensation without roughness, a tensile sensation, or an unpleasant sensation, and exhibited both superior usage effects at the time of application such as a spreading property and an adhesion sensation to the skin, and superior usage effects at the completion of the application such as absence of a sticky sensation at the time of contacting the application part with fingers, softness of the film, a following property to the skin and cosmetic durability, as compared with those of W/O emulsion liquid foundations in accordance with Comparative Examples 5 to 8.

Examples 6 to 8 and Comparative Examples 9 to 12

Hair conditioners having the compositions shown in Table 5 were prepared, and cosmetic properties thereof were functionally evaluated. In order to ensure objectivity, evaluation was carried out on the basis of the evaluation criteria described below. The results are also shown in Table 5. In the table, "parts" indicates "parts by weight (mass)".

Evaluation Criteria

A commercially available bundle of Chinese hair (manufactured by Beaulax Co., Ltd., 30 cm, 4 g) was subjected to a bleaching treatment for 10 minutes at room temperature, followed by cleansing the bundle with a 10% solution of sodium laureth sulfate. First, 10 panelists evaluated first, as usage effects during wetting, a sensation during use at the time of putting the composition on the palm of a hand, and then applying on hair (smoothness during spreading and lightness or heaviness), smoothness at the time of rinsing the hair by combing with the fingers in running water ten times, feeling to the touch (smoothness and a coating sensation) at the time of drying with a towel. Subsequently, 10 panelists evaluated, as usage effects during drying, conditioning effects after drying (natural smoothness and final combability with fingers). Each panelist answered a questionnaire on each evaluation category. In the case of the evaluation category evaluated as superiority by the panelist, 5 points were given, and in the case of the evaluation category evaluated as inferiority by the panelist, 1 point was given. In the case of the evaluation category evaluated as interlevels by the panelist, 2, 3, or 4 points were given. The average points obtained thereby were used as evaluation results of the sensation during use.

TABLE 5

|  |  | Example | | | Comparative Example | | | |
| --- | --- | --- | --- | --- | --- | --- | --- | --- |
| No. | Component | 6 | 7 | 8 | 9 | 10 | 11 | 12 |
| 1 | Cetanol | 5.6 | 5.6 | 5.6 | 5.6 | 5.6 | 5.6 | 5.6 |
| 2 | Stearyltrimonium chloride | 2.0 | 2.0 | 2.0 | 2.0 | 2.0 | 2.0 | 2.0 |
| 3 | Behentrimonium chloride | 1.0 | 1.0 | 1.0 | 1.0 | 1.0 | 1.0 | 1.0 |
| 4 | Mineral oil | 1.0 | 1.0 | 1.0 | 1.0 | 1.0 | 1.0 | 1.0 |
| 5 | Decamethylcyclopentasiloxane[1] | 4.5 | 4.5 | 4.5 | 4.5 | 4.5 | 4.5 | 4.5 |
| 6 | Phenyltrimethicone[2] | 1.0 | 1.0 | 1.0 | 1.0 | 1.0 | 1.0 | 1.0 |
| 7 | Silicone Compound No. 1 | 0.5 | — | — | — | — | — | — |
| 8 | Silicone Compound No. 3 | — | 0.5 | — | — | — | — | — |
| 9 | Silicone Compound No. 7 | — | — | 0.5 | — | — | — | — |
| 10 | Silicone Compound RE 1 | — | — | — | 0.5 | — | — | — |
| 11 | Silicone Compound RE 2 | — | — | — | — | 0.5 | — | — |
| 12 | Silicone gum[3] | — | — | — | — | — | 0.5 | — |
| 13 | Dimethicone (100 mm2/s)[4] | — | — | — | — | — | — | 0.5 |
| 14 | Methylisothiazolinone | 0.1 | 0.1 | 0.1 | 0.1 | 0.1 | 0.1 | 0.1 |
| 15 | EDTA-2Na | 0.1 | 0.1 | 0.1 | 0.1 | 0.1 | 0.1 | 0.1 |
| 16 | Purified water | 82.2 | 82.2 | 82.2 | 82.2 | 82.2 | 82.2 | 82.2 |
|  | Total parts | 100.0 | 100.0 | 100.0 | 100.0 | 100.0 | 100.0 | 100.0 |

TABLE 5-continued

|  |  | Example | | | Comparative Example | | | |
|---|---|---|---|---|---|---|---|---|
| No. | Component | 6 | 7 | 8 | 9 | 10 | 11 | 12 |
|  | Evaluation category | Evaluation results (points) | | | | | | |
| WET | Sensation during use, at the time of applying to the hair | 3.8 | 4.8 | 4.4 | 1.2 | 1.2 | 3.7 | 3.2 |
|  | Smoothness during rinsing in running water | 4.9 | 4.9 | 4.8 | 4.1 | 3.5 | 3.5 | 3.4 |
|  | Feeling to the touch during drying with a towel | 4.0 | 4.8 | 4.2 | 3.3 | 3.9 | 3.2 | 3.9 |
| DRY | Conditioning effects after drying | 4.7 | 4.9 | 4.0 | 3.9 | 3.7 | 3.6 | 2.6 |
|  | Refreshing sensation after drying | 4.8 | 4.6 | 3.6 | 1.8 | 3.0 | 3.7 | 1.3 |

*[1])Product name: SH 245 (manufactured by Dow Corning Toray Co., Ltd.)
*[2])Product name: SH 556 (manufactured by Dow Corning Toray Co., Ltd.)
*[3])Product name: SGM 36 (manufactured by Dow Corning Toray Co., Ltd.)
*[4])Product name: SH 200-100 cs (manufactured by Dow Corning Toray Co., Ltd.)

Preparation Method for a Hair Conditioner
(1) Components No. 1 to No. 13 were placed in a beaker with a volume of 200 mL, and heated and dissolved at 80° C. under stirring with a propeller mixer.
(2) Separately, Components No. 15 and No. 16 were heated and dissolved at 80° C.
(3) The solution obtained in the aforementioned (2) was added to the solution obtained in the aforementioned (1) while stirring, and the mixture was emulsified.
(4) The emulsion obtained in the aforementioned (3) was cooled while stirring, and Component No. 14 was added thereto at 40° C. or less.

The hair conditioners of Examples 6 to 8 were superior than the hair conditioners of Comparative Examples 9 to 12 in view of
usage effects during wetting, such as
(A) a sensation during use at the time of applying on hair (smoothness during spreading and lightness or heaviness),
(B) smoothness at the time of rinsing the hair in running water, and
(C) feeling to the touch (smoothness and a coating sensation) at the time of drying with a towel, and usage effects during drying, such as
(D) conditioning effects after drying (natural smoothness and final combability with fingers).

Examples 9 to 11 and Comparative Examples 13 to 16

Shampoos were prepared with the compositions shown in Table 6, and the cosmetic properties thereof were functionally evaluated. Each of the evaluation categories in the functional tests was evaluated on the basis of the following evaluation criteria in order to ensure objectivity. The results are shown in Table 6. In the table, "parts" indicates "parts by weight (mass)".

Evaluation Criteria
Ten panelists made the hair sufficiently wet with warm water, put an appropriate amount of the composition to be evaluated (the same as the amount of a shampoo in which the panelist usually used for shampooing) on the hand, and sufficiently shampooed the hair, followed by evaluating. First, the panelists evaluated, as usage effects during wetting, a sensation during use at the time of applying the composition to the hair (foam quality and a foaming property), smoothness during rinsing in running water, and feeling to the touch during drying with a towel (smoothness and a coating sensation), and evaluated, as usage effects during drying, a conditioning effect after drying (natural smoothness and finish combability with fingers). Each panelist answered a questionnaire on each evaluation category. In the case of the evaluation category evaluated as superiority by the panelist, 5 points were given, and in the case of the evaluation category evaluated as inferiority by the panelist, 1 point was given. In the case of the evaluation category evaluated as interlevels by the panelist, 2, 3, or 4 points were given. The average points obtained thereby were used as evaluation results of the sensation during use.

TABLE 6

|  |  | Example | | | Comparative Example | | | |
|---|---|---|---|---|---|---|---|---|
| No. | Component | 9 | 10 | 11 | 13 | 14 | 15 | 16 |
| 1 | Sodium POE (2) lauryl ether sulfate (70% by weight (mass) aqueous solution) | 17.86 | 17.86 | 17.86 | 17.86 | 17.86 | 17.86 | 17.86 |
| 2 | Cocamidopropylbetaine (30% by weight (mass) aqueous solution) | 8.33 | 8.33 | 8.33 | 8.33 | 8.33 | 8.33 | 8.33 |
| 3 | Cetanol | 0.5 | 0.5 | 0.5 | 0.5 | 0.5 | 0.5 | 0.5 |

TABLE 6-continued

|  |  | Example | | | Comparative Example | | | |
| --- | --- | --- | --- | --- | --- | --- | --- | --- |
| No. | Component | 9 | 10 | 11 | 13 | 14 | 15 | 16 |
| 4 | Cationated cellulose (2% by weight (mass) aqueous solution) | 25.0 | 25.0 | 25.0 | 25.0 | 25.0 | 25.0 | 25.0 |
| 5 | Cationated guar gum | 0.05 | 0.05 | 0.05 | 0.05 | 0.05 | 0.05 | 0.05 |
| 6 | Copolymer-type cationic polymer of dimethyldiallylammonium halide and acrylamide (9% by weight (mass) aqueous solution) | 1.67 | 1.67 | 1.67 | 1.67 | 1.67 | 1.67 | 1.67 |
| 7 | Sodium benzoate | 0.3 | 0.3 | 0.3 | 0.3 | 0.3 | 0.3 | 0.3 |
| 8 | Glycol distearate | 1.0 | 1.0 | 1.0 | 1.0 | 1.0 | 1.0 | 1.0 |
| 9 | O/W emulsion[*1)] obtained by emulsifying a mixture of Silicone Compound No. 1 and dimethyl-polysiloxane (2 cs) | 4.0 | — | — | — | — | — | — |
| 10 | O/W emulsion[*1)] obtained by emulsifying a mixture of Silicone Compound No. 3 and dimethyl-polysiloxane (2 cs) | — | 4.0 | — | — | — | — | — |
| 11 | O/W emulsion[*1)] obtained by emulsifying a mixture of Silicone Compound No. 7 and dimethyl-polysiloxane (2 cs) | — | — | 4.0 | — | — | — | — |
| 12 | O/W emulsion[*1)] obtained by emulsifying a mixture of Silicone Compound RE 1 and dimethylpolysiloxane (2 cs) | — | — | — | 4.0 | — | — | — |
| 13 | O/W emulsion[*1)] obtained by emulsifying a mixture of Silicone Compound RE 2 and dimethyl-polysiloxane (2 cs) | — | — | — | — | 4.0 | — | — |
| 14 | O/W emulsion[*1)] obtained by emulsifying a mixture of silicone gum[*2)] and dimethylpolysiloxane (2 cs) | — | — | — | — | — | 4.0 | — |
| 15 | O/W emulsion[*1)] obtained by emulsifying a mixture of dimethicone (100 mm$^2$/s)[*3)] and dimethyl-polysiloxane (2 cs) | — | — | — | — | — | — | 4.0 |
| 16 | Citric acid | 0.05 | 0.05 | 0.05 | 0.05 | 0.05 | 0.05 | 0.05 |
| 17 | Purified water | 41.24 | 41.24 | 41.24 | 41.24 | 41.24 | 41.24 | 41.24 |
|  | Total parts | 100.0 | 100.0 | 100.0 | 100.0 | 100.0 | 100.0 | 100.0 |
|  | Evaluation category | Evaluation results (points) | | | | | | |
| WET | Foam quality and foaming property | 4.0 | 4.8 | 4.5 | 1.1 | 1.2 | 4.0 | 3.8 |
|  | Smoothness during rinsing in running water | 4.7 | 4.9 | 4.8 | 4.0 | 3.2 | 3.3 | 3.5 |
|  | Feeling to the touch during drying with a towel | 3.7 | 4.5 | 4.6 | 3.1 | 3.3 | 3.1 | 3.6 |
| DRY | Conditioning effects after drying | 4.7 | 4.5 | 4.5 | 2.0 | 2.8 | 3.0 | 2.2 |

[*1)]O/W emulsion comprising 60% by weight (mass) of a liquid obtained by mixing and uniformizing a silicone compound (10 parts) and a dimethylpolysiloxane (2 cs) (90 parts), produced by emulsifying the formulation shown in Table 7 described below.
[*2)]Product name: SGM 36 (manufactured by Dow Corning Toray Co., Ltd.)
[*3)]Product name: SH 200-100 cs (manufactured by Dow Corning Toray Co., Ltd.)

TABLE 7

| Name of raw material | Type of raw material | Parts by weight (mass) |
|---|---|---|
| Mixture of silicone compound and dimethylpolysiloxane (2 cs) (10:90) | Oil agent | 60.0 |
| POE (4) lauryl ether | Nonionic emulsifier | 2.1 |
| POE (25) lauryl ether | Nonionic emulsifier | 2.9 |
| Cetyl trimethylammonium chloride (30% by weight (mass) aqueous solution) | Cationic emulsifier | 0.5 |
| Sodium benzoate | Preservatives | 0.5 |
| Citric acid | pH adjustor | 0.2 |
| Purified water | Water | 33.8 |
| Total | | 100.0 |

Preparation Method for a Shampoo (1) Components No. 1 to No. 3, Components No. 7 to No. 8, and Component No. 17 were placed in a beaker with a volume of 200 mL, and the mixture was stirred by means of a propeller mixer and completely dissolved while the temperature was maintained at 70° C.
(2) Components No. 4 to No. 6 were added to the solution obtained in the aforementioned step (1) while the temperature was maintained at 70° C., and the mixture was completely dissolved.
(3) Components No. 9 to No. 15 were added thereto at 55° C. while the solution obtained in the aforementioned step (2) was stirred.
(4) The mixture was cooled to room temperature, and Component No. 16 was added thereto while stirring.

It was verified that the shampoo compositions according to Examples 9 to 11 were superior, as compared with the shampoo compositions according to Comparative Examples 13 to 16, in view of both usage effects during wetting such as (A) cleansing effects such as foam quality and foaming property, (B) smoothness in the wetting state after rinsing, and (C) feeling to the touch at the time of drying with a towel (such as appropriately natural smoothness which was close to that of healthy hair without damage), and usage effects during drying such as (D) conditioning effects after drying (such as a moisturizing sensation, combability with fingers, and lightness and heaviness).

Hereinafter, particular formulations of cosmetics of the present invention are described as examples of the present invention. It should be understood that the present invention is not restricted thereto. In the series of Formulation Examples, in view of improvement of feeling to the touch to the skin or hair, Silicone Compound No. 3 is the most preferable. For this reason, in Formulation Examples, Silicone Compound No. 3 is used. Therefore, it should be understood that Silicone Compound 3 used in Formulation Examples can be replaced with another modified silicone according to the present invention (such as each of the aforementioned Silicone Compound Nos. 1, 2, and 4 to 9), and a mixture of two or more types of modified silicones according to the present invention can also be used.

Formulation Example 1

W/O Emulsion

The numerical value described after each component indicates part(s) by weight (mass).

| | (Components) | |
|---|---|---|
| 1. | Dimethylpolysiloxane (2 cSt) | 2.0 |
| 2. | Decamethylcyclopentasiloxane | 15.0 |
| 3. | Polyether-modifeid silicone (Note) | 5.0 |
| 4. | Cetyl isooctanoate | 5.0 |
| 5. | Trioctanoin | 9.0 |
| 6. | Silicone Compound No. 3 | 1.0 |
| 7. | Paraoxybenzoic ester | 0.1 |
| 8. | Sodium lactate | 0.5 |
| 9. | Purified water | remainder |

Note:
5200 Formulation Aid, manufactured by Dow Corning Corporation.

Preparation Procedure
Step 1: Components 1 to 6 are mixed and dispersed.
Step 2: A mixture of components 7 to 9 is added to the composition obtained in Step 1 to emulsify them at room temperature. A container is charged with the emulsion, and thereby, a product is obtained.

Formulation Example 2

W/O Emulsion

The numerical value described after each component indicates part(s) by weight (mass).

| | (Components) | |
|---|---|---|
| 1. | Methyltrimethicone | 12.0 |
| 2. | Dimethylpolysiloxane (6 cSt) | 7.0 |
| 3. | Silicone Compound No. 3 | 5.0 |
| 4. | Squalane | 5.0 |
| 5. | Neopentyl glycol dioctanoate | 3.0 |
| 6. | Alpha-monooleyl glyceryl ether | 1.0 |
| 7. | Polyether-modifeid silicone (Note) | 2.0 |
| 8. | Aluminum distearate | 0.2 |
| 9. | Magnesium sulfate | 0.7 |
| 10. | Glycerol | 5.0 |
| 11. | Preservatives | q.s. |
| 12. | Purified water | remainder |
| 13. | Perfume | q.s. |

Note:
SS-2910, manufactured by Dow Corning Toray Co., Ltd.

Preparation Procedure
Step 1: Components 1 to 8 are mixed.
Step 2: Components 9 to 12 are heated and dissolved.
Step 3: The composition obtained in Step 2 is gradually added to the composition obtained in Step 1 to emulsify them. The emulsion is cooled, and component 13 is added thereto. Thereby, an emulsion is obtained.

Formulation Example 3

W/O Emulsion

The numerical value described after each component indicates part(s) by weight (mass).

| | (Components) | |
|---|---|---|
| 1. | Stearic acid | 0.8 |
| 2. | Self-emulsion-type glycerol monostearate | 0.8 |
| 3. | Polyethylene glycol monostearate | 1.1 |

-continued

| | (Components) | |
|---|---|---|
| 4. | Cetostearyl alcohol | 0.6 |
| 5. | Decamethylcyclopentasiloxane | 3.0 |
| 6. | Silicone Compound No. 3 | 3.0 |
| 7. | Trioctanoin | 2.0 |
| 8. | Squalane | 2.0 |
| 9. | Paraoxybenzoic ester | 0.1 |
| 10. | Phenoxyethanol | 0.2 |
| 11. | 1,3-butylene glycol | 7.0 |
| 12. | Glycerol | 5.0 |
| 13. | Carboxyvinyl polymer | 0.04 |
| 14. | Xanthan gum | 0.02 |
| 15. | Potassium hydroxide | 0.04 |
| 16. | Purified water | remainder |

Preparation Procedure
Step 1: Components 1 to 8 are heated and dissolved.
Step 2: Components 9 to 16 are heated and dissolved.
Step 3: The composition obtained in Step 1 is gradually added to the composition obtained in Step 2 to emulsify them. The emulsion is cooled.

Formulation Example 4

Skin Care Cream

The numerical value described after each component indicates part(s) by weight (mass).

| | (Components) | |
|---|---|---|
| 1. | Stearic acid | 2.0 |
| 2. | Cetostearyl alcohol | 1.8 |
| 3. | Glycol monostearate | 1.5 |
| 4. | Sorbitan stearate | 0.5 |
| 5. | Polyoxyethylene sorbitan monooleate (20 EO) | 0.5 |
| 6. | Liquid paraffin | 10.0 |
| 7. | Decamethylcyclopentasiloxane | 3.0 |
| 8. | Dimethylpolysiloxane (6 cSt) | 2.0 |
| 9. | Silicone Compound No. 3 | 3.0 |
| 10. | Glycerol trioctanoate | 3.0 |
| 11. | Triethanolamine | 1.5 |
| 12. | 1,3-butylene glycol | 10.0 |
| 13. | Purified water | remainder |

Preparation Procedure
Step 1: Components 1 to 10 are heated and dissolved.
Step 2: Components 11 to 13 are heated and dissolved.
Step 3: The composition obtained in Step 2 is gradually added to the composition obtained in Step 1 to emulsify them. The emulsion is cooled.

Formulation Example 5

W/O-Type Cream

The numerical value described after each component indicates part(s) by weight (mass).

| | (Components) | |
|---|---|---|
| 1. | Silicone Compound No. 3 | 2.0 |
| 2. | Liquid paraffin | 13.5 |
| 3. | Squalane | 4.0 |
| 4. | Macadamia nut oil | 3.3 |
| 5. | Polyether-modified silicone (Note) | 2.2 |
| 6. | Sodium citrate | 0.2 |
| 7. | Propylene glycol | 8.0 |

-continued

| | (Components) | |
|---|---|---|
| 8. | Glycerol | 3.0 |
| 9. | Preservatives | q.s. |
| 10. | Perfume | q.s. |
| 11. | Purified water | 60.8 |

Note:
5200 Formulation Aid, manufactured by Dow Corning Corporation.

Preparation Procedure
Step 1: Components 1 to 5 are mixed.
Step 2: Components 6 to 11 are mixed, and the mixture is added to the composition obtained in Step 1 to emulsify them.

Formulation Example 6

W/O-Type Cream

The numerical value described after each component indicates part(s) by weight (mass).

| | (Components) | |
|---|---|---|
| 1. | Dimethicone crosspolymer (Note 1) | 3.0 |
| 2. | Silicone Compound No. 3 | 2.0 |
| 3. | Liquid paraffin | 14.0 |
| 4. | Glyceryl tri-2-ethylhexanoate | 1.0 |
| 5. | Macadamia nut oil | 5.0 |
| 6. | Polyether-modified silicone (Note 2) | 1.0 |
| 7. | Silicone elastomer powder (Note 3) | 3.0 |
| 8. | Sodium citrate | 0.2 |
| 9. | Propylene glycol | 8.0 |
| 10. | Glycerol | 3.0 |
| 11. | Preservatives | q.s. |
| 12. | Perfume | q.s. |
| 13. | Purified water | 59.8 |

Note 1:
9011 Silicone Elastomer Blend, manufactured by Dow Corning Corporation.
Note 2:
5200 Formulation Aid, manufactured by Dow Corning Corporation.
Note 3:
Trefil E-506 S, manufactured by Dow Corning Toray Co., Ltd.

Preparation Procedure
Step 1: Components 1 to 7 are mixed.
Step 2: Components 8 to 13 are mixed, and the mixture is added to the composition obtained in Step 1 to emulsify them.

Formulation Example 7

W/O-Type Cream

The numerical value described after each component indicates part(s) by weight (mass).

| | (Components) | |
|---|---|---|
| 1. | Silicone Compound No. 3 | 3.5 |
| 2. | Decamethylcyclopentasiloxane | 10.0 |
| 3. | Dimethylpolysiloxane (6 cSt) | 18.0 |
| 4. | Polyether-modified silicone (Note 1) | 0.7 |
| 5. | Propylene glycol | 3.0 |
| 6. | Polyacrylamide-based mixture (Note 2) | 0.8 |
| 7. | Xanthan gum (2% aqueous solution) | 8.0 |

| (Components) | | |
|---|---|---|
| 8. | Preservatives | q.s. |
| 9. | Perfume | q.s. |
| 10. | Purified water | 42.5 |

Note 1:
SH 3771 M, manufactured by Dow Corning Corporation.
Note 2:
SEPIGEL 305, manufactured by Sepic.

Preparation Procedure
Step 1: Components 1 to 3 are mixed.
Step 2: Components 4 to 10 are mixed.
Step 3: The composition obtained in Step 1 is added to the composition obtained in Step 2 to emulsify them.

Formulation Example 8

W/O-Type Liquid Foundation

The numerical value described after each component indicates part(s) by weight (mass).

| (Components) | | |
|---|---|---|
| 1. | Polyether-modified silicone (Note 1) | 10.0 |
| 2. | Decamethylcyclopentasiloxane | 18.0 |
| 3. | Silicone Compound No. 3 | 8.0 |
| 4. | Dimethicone crosspolymer (Note 2) | 4.0 |
| 5. | Ethylhexyl 2-ethylhexanoate | 5.0 |
| 6. | Octylsilane-treated red iron oxide | 0.1 |
| 7. | Octylsilane-treated yellow iron oxide | 0.6 |
| 8. | Mica | 3.5 |
| 9. | Octylsilane-treated black iron oxide | 0.05 |
| 10. | Purified water | remainder |
| 11. | Polysolbate 20 | 0.2 |
| 12. | Preservatives | 0.5 |
| 13. | Xanthan gum | 0.5 |
| 14. | Magnesium sulfate | 0.4 |

Note 1:
5200 Formulation Aid, manufactured by Dow Corning Corporation.
Note 2:
9040 Silicone Elastomer Blend, manufactured by Dow Corning Corporation.

Preparation Procedure
Step 1: Components 1 to 9 are mixed and dispersed.
Step 2: Components 10 to 14 are mixed and dispersed.
Step 3: The composition obtained in Step 2 is added to the composition obtained in Step 1 to emulsify them.

Formulation Example 9

W/O-Type Liquid Foundation

The numerical value described after each component indicates part(s) by weight (mass).

| (Components) | | |
|---|---|---|
| 1. | Stearic acid | 2.4 |
| 2. | Propylene glycol stearate | 2.0 |
| 3. | Cetyl alcohol | 0.2 |
| 4. | Liquid lanolin | 2.0 |
| 5. | Liquid paraffin | 1.0 |
| 6. | Silicone Compound No. 3 | 2.0 |
| 7. | Isopropyl myristate | 8.5 |
| 8. | Purified water | remainder |
| 9. | Carboxymethylcellulose sodium | 0.2 |
| 10. | Bentonite | 0.5 |

| (Components) | | |
|---|---|---|
| 11. | Dipropylene glycol | 4.0 |
| 12. | Triethanolamine | 1.1 |
| 13. | Preservatives | q.s. |
| 14. | Titanium oxide | 8.0 |
| 15. | Mica | 4.0 |
| 16. | Color pigment | q.s. |
| 17. | Perfume | q.s. |

Preparation Procedure
Step 1: Components 8 to 16 are heated and subsequently mixed and dispersed.
Step 2: Components 1 to 7 are heated and subsequently mixed.
Step 3: The composition obtained in Step 2 is added to the composition obtained in Step 1 to emulsify them.
Subsequently, component 17 is added thereto, and the mixture is cooled to room temperature.

Formulation Example 10

W/O-Type Sunscreen Milk

The numerical value described after each component indicates part(s) by weight (mass).

| (Components) | | |
|---|---|---|
| 1. | 2-ethylhexyl paramethoxycinnamate | 4.0 |
| 2. | Hexyl diethylaminohydroxybenzoylbenzoate | 1.0 |
| 3. | Silicone-treated microparticulate titanium oxide | 5.0 |
| 4. | Silicone-treated microparticulate zinc oxide | 9.0 |
| 5. | Squalane | 15.0 |
| 6. | Dioctyl succinate | 5.0 |
| 7. | Silicone Compound No. 3 | 5.0 |
| 8. | Dimethylpolysiloxane (2 cSt) | 10.0 |
| 9. | Decamethylcyclopentasiloxane | 8.0 |
| 10. | Decamethylcyclopentasiloxane/(acrylate/polytrimethylsiloxy methacrylate) copolymer (Note 1) | 2.0 |
| 11. | Glycerol diisostearate | 2.0 |
| 12. | Polyether-modified silicone (Note 2) | 0.5 |
| 13. | Organo-modified montmorillonite | 0.5 |
| 14. | Purified water | remainder |
| 15. | 1,3-butylene glycol | 5.0 |

Note 1:
FA 4001 CM Silicone Acrylate, manufactured by Dow Corning Corporation.
Note 2:
SS-2910, manufactured by Dow Corning Corporation.

Preparation Procedure
Step 1: Components 3 and 4 are mixed with components 7 to 10, and the mixture is micro-pulverized.
Step 2: Components 1, 2, 5, 6, and 11 to 13 are added to the composition obtained in Step 1, and the mixture is heated and mixed.
Step 3: A mixture of components 14 and 15 is gradually added to the composition obtained in Step 2 to emulsify them.

Formulation Example 11

W/O-Type Sunscreen Milk

The numerical value described after each component indicates part(s) by weight (mass).

| | (Components) | |
|---|---|---|
| 1. | Microparticulate titanium oxide slurry (decamethylcyclopentasiloxane solution, solid content = 30%) | 10.0 |
| 2. | Microparticulate zinc oxide slurry (decamethylcyclopentasiloxane solution, solid content = 35%) | 30.0 |
| 3. | 2-ethylhexyl paramethoxycinnamate | 8.0 |
| 4. | Hexyl diethylaminohydroxybenzoylbenzoate | 2.0 |
| 5. | Silicone Compound No. 3 | 4.0 |
| 6. | Caprylyl methicone | 3.0 |
| 7. | Trimethylsiloxysilicic acid solution | 7.5 |
| 8. | Dimethylpolysiloxane (6 cSt) | 4.5 |
| 9. | Polyether-modified silicone (Note) | 1.0 |
| 10. | Isodecyl isononanoate | 1.0 |
| 11. | Silica | 2.5 |
| 12. | Purified water | remainder |
| 13. | Preservatives | q.s. |
| 14. | 1,3-propanediol | 2.0 |
| 15. | Aloe extract | 1.0 |

Note:
SS-2910, manufactured by Dow Corning Corporation.

Preparation Procedure
Step 1: Components 1 to 10 are mixed and dispersed.
Step 2: Components 11 to 15 are mixed.
Step 3: The composition obtained in Step 2 is added to the composition obtained in Step 1 to emulsify them.

Formulation Example 12

W/O-Type Sunscreen Cream

The numerical value described after each component indicates part(s) by weight (mass).

| | (Components) | |
|---|---|---|
| 1. | Polyether-modified silicone mixture (Note 1) | 10.0 |
| 2. | Sodium tri(POE)lauryl ether phosphate | 0.05 |
| 3. | Hexyl diethylaminohydroxybenzoylbenzoate | 2.0 |
| 4. | 2-ethylhexyl paramethoxycinnamate | 6.0 |
| 5. | Silicone Compound No. 3 | 3.0 |
| 6. | Dimethylpolysiloxane (6 cSt) | 2.0 |
| 7. | Phenyltrimethicone | 2.0 |
| 8. | Carbomer (2% by weight (mass) aqueous solution) | 22.5 |
| 9. | Purified water | remainder |
| 10. | Sodium hydroxide (1% by weight (mass) aqueous solution) | 10.5 |
| 11. | Polyoxypropylene methylglucoside | 0.4 |
| 12. | Ethanol | 2.0 |
| 13. | 1,3-butylene glycol | 5.0 |
| 14. | Glycerol | 5.0 |
| 15. | Preservatives | q.s. |
| 16. | (Dimethicone/vinyldimethicone) crosspolymer (Note 2) | 2.5 |

Note 1:
FB-2540, manufactured by Dow Corning Corporation.
Note 2:
BY29-129, manufactured by Dow Corning Corporation.

Preparation Procedure
Step 1: Components 8 to 15 are mixed.
Step 2: Components 1 to 7 are mixed.
Step 3: The composition obtained in Step 2 is added to the composition obtained in Step 1 to emulsify them.
Step 4: Component 16 is added to the composition obtained in Step 3, and the mixture is stirred and mixed.

Formulation Example 13

Eye Shadow

The numerical value described after each component indicates part(s) by weight (mass).

| | (Components) | |
|---|---|---|
| 1. | Sericite | 40.0 |
| 2. | Mica | 10.0 |
| 3. | Talc | remainder |
| 4. | Titanium oxide | 10.0 |
| 5. | Microparticulate titanium oxide | 5.0 |
| 6. | Magnesium stearate | 3.0 |
| 7. | Pigment | q.s. |
| 8. | Octyldodecanol | 3.0 |
| 9. | Dimethylpolysiloxane (6 cSt) | 4.0 |
| 10. | Silicone Compound No. 3 | 3.0 |
| 11. | Preservatives | q.s. |
| 12. | Perfume | q.s. |

Preparation Procedure
Step 1: Components 8 to 11 are mixed.
Step 2: Components 1 to 7 are mixed.
Step 3: The composition obtained in Step 1 is added to the composition obtained in Step 2 to emulsify them.
Step 4: Component 12 is added to the composition obtained in Step 3, and the mixture is stirred and mixed.

Formulation Example 14

Eyeliner

The numerical value described after each component indicates part(s) by weight (mass).

| | (Components) | |
|---|---|---|
| 1. | Silicone Compound No. 3 | 8.0 |
| 2. | Decamethylcyclopentasiloxane | 10.0 |
| 3. | Dimethylpolysiloxane (6 cSt) | 5.0 |
| 4. | Caprylyl methicone | 4.0 |
| 5. | Jojoba oil | 2.0 |
| 6. | Polyether-modified silicone (Note) | 1.0 |
| 7. | Silicone-treated black iron oxide | 20.0 |
| 8. | Ethanol | 5.0 |
| 9. | Preservatives | q.s. |
| 10. | Purified water | remainder |

Note:
SS-2910, manufactured by Dow Corning Toray Co., Ltd.

Preparation Procedure
Step 1: Components 1 to 5 are heated and mixed, and component 6 is added thereto to disperse therein.
Step 2: Components 7 to 9 are mixed.
Step 3: The composition obtained in Step 2 is added to the composition obtained in Step 1, and the mixture is uniformly heated.

Step 4: Component 10 is added to the composition obtained in Step 3, and the mixture is stirred and mixed.

Formulation Example 15

Humectant Cream

The numerical value described after each component indicates part(s) by weight (mass).

| (Components) | | |
|---|---|---|
| 1. | Silicone Compound No. 3 | 5.0 |
| 2. | Decamethylcyclopentasiloxane | 5.0 |
| 3. | Phenyltrimethicone | 3.0 |
| 4. | Liquid paraffin | 5.0 |
| 5. | Pentaerythritol tetra-2-ethylhexanoate | 3.0 |
| 6. | Cetyl 2-ethylhexanoate | 5.0 |
| 7. | Polyether-modified silicone (Note 1) | 1.0 |
| 8. | Silicone elastomer powder (Note 2) | 2.5 |
| 9. | Hydrophobic silica | 2.0 |
| 10. | Zinc stearate | 2.0 |
| 11. | Vitamin E acetate | 3.0 |
| 12. | Polyethylene glycol 400 | 1.0 |
| 13. | Sodium lactate | 1.0 |
| 14. | 1,3-butylene glycol | 5.0 |
| 15. | Preservatives | q.s. |
| 16. | Perfume | q.s. |
| 17. | Purified water | remainder |

Note 1:
SS-2910, manufactured by Dow Corning Toray Co., Ltd.
Note 2:
Trefil E-506S, manufactured by Dow Corning Toray Co., Ltd.

Preparation Procedure
Step 1: Components 1 to 7 and components 10 and 11 are uniformly mixed, and components 8 and 9 are added thereto and uniformly dispersed therein.
Step 2: Components 12 to 15 and components 17 are mixed and dissolved.
Step 3: The composition obtained in Step 2 is gradually added to the composition obtained in Step 1 to emulsify the mixture and cool the emulsion.
Step 4: Component 16 is added to the composition obtained in Step 3, and the mixture is stirred and mixed.

Formulation Example 16

Cream for after Shaving

The numerical value described after each component indicates part(s) by weight (mass).

| (Components) | | |
|---|---|---|
| 1. | Silicone Compound No. 3 | 15.0 |
| 2. | Decamethylcyclopentasiloxane | 20.0 |
| 3. | Polyether-modified silicone (Note 1) | 3.0 |
| 4. | Polyether-modified silicone (Note 2) | 5.0 |
| 5. | Polyethylene glycol 400 | 5.0 |
| 6. | Sodium L-glutamate | 2.0 |
| 7. | Allantoin | 0.1 |
| 8. | Aloe extract | q.s. |
| 9. | Preservatives | q.s. |
| 10. | Antioxidant | q.s. |
| 11. | Perfume | q.s. |
| 12. | Purified water | remainder |

Note 1:
SS-2910, manufactured by Dow Corning Toray Co., Ltd.
Note 2:
5200 Formulation Aid, manufactured by Dow Corning Corporation.

Preparation Procedure
Step 1: Components 1 to 5 and components 11 and 12 are heated and mixed.
Step 2: Components 6 to 10 are heated and mixed.
Step 3: The composition obtained in Step 2 is gradually added to the composition obtained in Step 1 to emulsify the mixture.

Formulation Example 17

Lipstick

The numerical value described after each component indicates part(s) by weight (mass).

| (Components) | | |
|---|---|---|
| 1. | Microcrystalline wax | 10.0 |
| 2. | Paraffin wax | 15.0 |
| 3. | Carnauba wax | 5.0 |
| 4. | Vaseline | 5.0 |
| 5. | Diisostearyl malate | 7.0 |
| 6. | Glyceryl triisostearate | 11.5 |
| 7. | Propylene glycol dicaprate | 7.0 |
| 8. | Inulin stearate (Note 1) | 2.0 |
| 9. | Silicone Compound No. 3 | 3.0 |
| 10. | Decamethylcyclopentasiloxane | 10.0 |
| 11. | Decamethylcyclopentasiloxane/(acrylate/ polytrimethylsiloxy methacrylate) copolymer (Note 2) | 3.0 |
| 12. | Dimethylpolysiloxane of trimethylsiloxy-silicic acid (100 mm$^2$/s) solution (active component = 33%) (Note 3) | 2.0 |
| 13. | Red No. 201 | 1.0 |
| 14. | Red No. 202 | 1.0 |
| 15. | Yellow No. 4 | 2.0 |
| 16. | Titanium oxide | 4.0 |
| 17. | Black iron oxide | 0.5 |
| 18. | Iron oxide titanium mica | 3.0 |
| 19. | Titanium mica | 2.0 |
| 20. | Purified water | 5.0 |
| 21. | 1,3-butylene glycol | 1.0 |
| 22. | Preservatives | q.s. |
| 23. | Perfume | q.s. |

Note 1:
Rheopearl ISL2, manufactured by Chiba Flour Milling Co., Ltd.
Note 2:
FA4001CM Silicone Acrylate, manufactured by Dow Corning Toray Co., Ltd.
Note 3:
DC 593, manufactured by Dow Corning Corporation.

Preparation Procedure
Step 1: Components 1 to 19 are heated, and then mixed and dissolved.
Step 2: Components 20 to 22 are mixed.
Step 3: The composition obtained in Step 2 is added to the composition obtained in Step 1, and the mixture is mixed.
Step 4: Component 23 is added to the composition obtained in Step 3, and an air-tight container is charged with the mixture.

Formulation Example 18

Lip Gloss

The numerical value described after each component indicates part(s) by weight (mass).

| | (Components) | |
|---|---|---|
| 1. | Silicone Compound No. 3 | 10.0 |
| 2. | Silicic anhydride (average primary particle size = 10 nm) | 1.5 |
| 3. | Diisostearyl malate | 15.0 |
| 4. | Stearyl alcohol | 4.0 |
| 5. | Methyltrimethicone | 1.0 |
| 6. | Phenyltrimethicone | 3.0 |
| 7. | Heavy liquid isoparaffin | remainder |
| 8. | Trimethylpentaphenyltrisiloxane | 1.0 |
| 9. | Squalane | 9.0 |
| 10. | Sunflower oil | 5.0 |
| 11. | Tricaprylyl glyceryl (=glyceryl tricaprate) | 5.0 |
| 12. | Vaseline | 5.0 |
| 13. | Microcrystalline wax | 2.0 |
| 14. | Red No. 202 | 0.8 |
| 15. | Titanium mica | 3.0 |

Preparation Procedure
Step 1: Components 1 to 15 are heated and mixed, and a container is charged with the mixture, followed by cooling.

Formulation Example 19

Lip Gloss

The numerical value described after each component indicates part(s) by weight (mass).

| | (Components) | |
|---|---|---|
| 1. | Polyamide-modified silicone (Note 1) | 19.0 |
| 2. | Silicone Compound No. 3 | 10.0 |
| 3. | Methylphenyl-modified silicone | 28.0 |
| 4. | Isononyl isononanoate | 38.0 |
| 5. | Trioctanoin | 2.0 |
| 6. | Titanium mica | 3.0 |

Note 1:
2-8178 gellant, manufactured by Dow Corning Corporation.

Preparation Procedure
Step 1: Components 1 to 6 are heated and mixed, and a container is charged with the mixture, followed by cooling.

Formulation Example 20

Mascara

The numerical value described after each component indicates part(s) by weight (mass).

| | (Components) | |
|---|---|---|
| 1. | Paraffin wax | 5.0 |
| 2. | Light liquid isoparaffin | remainder |
| 3. | Caprylmethicone | 0.5 |
| 4. | Silicone Compound No. 3 | 0.5 |
| 5. | Trioctanoin | 13.0 |
| 6. | Decamethylcyclopentasiloxane | 20.0 |
| 7. | Inulin stearate | 5.0 |
| 8. | Dimethicone crosspolymer (Note) | 10.0 |
| 9. | Fluorine compound-surface-treated black iron oxide | 6.0 |
| 10. | Sucrose fatty acid ester | 4.0 |
| 11. | Beeswax | 5.0 |
| 12. | Pentaerythritol rosinate | 5.0 |
| 13. | Preservatives | q.s. |
| 14. | Purified water | 5.0 |

Note:
9040 Silicone Elastomer Blend, manufactured by Dow Corning Corporation.

Preparation Procedure
Step 1: Components 1 to 12 are heated and then mixed and dispersed. Subsequently, a mixture of components 13 and 14 is added and emulsified. A container is charged with the emulsion.

Formulation Example 21

Cleansing Cream

The numerical value described after each component indicates part(s) by weight (mass).

| | (Components) | |
|---|---|---|
| 1. | Acrylic acid/alkyl methacrylate copolymer (Note) | 0.25 |
| 2. | Sodium hydroxide, 1% aqueous solution | 7.0 |
| 3. | Dipropylene glycol | 5.0 |
| 4. | Glycerol | 15.0 |
| 5. | Purified water | remainder |
| 6. | Sucrose fatty acid ester | 0.5 |
| 7. | Polyoxyethylene coconut oil fatty acid monoethanolamide (2 E.O.) | 0.5 |
| 8. | Tocopherol acetate | 0.1 |
| 9. | Preservatives | q.s. |
| 10. | Perfume | q.s. |
| 11. | Ethanol | 4.5 |
| 12. | Silicone Compound No. 3 | 0.5 |

Note:
Pemulen TR-1, manufactured by The Lubrizol Corporation.

Preparation Procedure
Step 1: Components 1 to 5 are mixed.
Step 2: Components 6 to 12 are uniformly mixed and dissolved.
Step 3: The mixture obtained in Step 2 is added to the mixture obtained in Step 1, and the entire mixture is mixed.

Formulation Example 22

Makeup Remover

The numerical value described after each component indicates part(s) by weight (mass).

| | (Components) | |
|---|---|---|
| 1. | Acrylic acid/alkyl methacrylate copolymer (Note) | 0.1 |
| 2. | Triethanolamine | 0.05 |
| 3. | Methyltrimethicone | 7.0 |
| 4. | Squalane | 1.0 |
| 5. | Silicone Compound No. 3 | 2.0 |
| 6. | Vitamin E acetate | 0.2 |
| 7. | Polyether-modified silicone | 0.5 |
| 8. | Sodium hyaluronate | 1.0 |
| 9. | Disodium edentate | 0.1 |
| 10. | Propylene glycol | 7.0 |
| 11. | Phenoxyethanol | q.s. |
| 12. | Purified water | remainder |

Note:
Pemulen TR-1, manufactured by The Lubrizol Corporation.

Preparation Procedure

Step 1: Components 1 and 2 and components 6 to 12 are uniformly mixed, and a mixture obtained by mixing components 3 to 5 is added thereto to emulsify them.

Formulation Example 23

Foundation Cream

The numerical value described after each component indicates part(s) by weight (mass).

| | (Components) | |
|---|---|---|
| 1. | Dimethylpolysiloxane (2 cSt) | 2.0 |
| 2. | Decamethylcyclopentasiloxane | 10.0 |
| 3. | Polyether-modified silicone (Note 1) | 3.0 |
| 4. | Cetyl isooctanoate | 5.0 |
| 5. | Silicone Compound No. 3 | 5.0 |
| 6. | 2-ethylhexyl paramethoxycinnamate | 2.0 |
| 7. | Silicone elastomer (Note 2) | 4.0 |
| 8. | Organo-modified bentonite | 0.5 |
| 9. | Barium sulfate | 2.0 |
| 10. | Talc | 1.0 |
| 11. | Nylon powder | 3.0 |
| 12. | Preservatives | q.s. |
| 13. | Xanthan gum | 0.1 |
| 14. | Magnesium L-ascorbyl phosphate | 0.3 |
| 15. | Purified water | remainder |

Note 1:
SS-2910, manufactured by Dow Corning Toray Co., Ltd.
Note 2:
9045 Silicone Elastomer Blend, manufactured by Dow Corning Corporation.

Preparation Procedure

Step 1: Components 1 to 11 are mixed and dispersed.
Step 2: A mixture of components 12 to 15 is added to the mixture obtained in Step 1, and they are emulsified at room temperature.

Formulation Example 24

Antiperspirant

The numerical value described after each component indicates part(s) by weight (mass).

| | (Components) | |
|---|---|---|
| 1. | Silicone elastomer (Note 1) | 20.0 |
| 2. | Dimethicone crosspolymer (Note 2) | 20.0 |
| 3. | Silicone Compound No. 3 | 15.0 |
| 4. | Decamethylcyclopentasiloxane | 15.0 |
| 5. | Aluminum Zirconium tetrachloride, hydrate | 20.0 |
| 6. | Dimethylpolysiloxane (6 cSt) | 10.0 |

Note 1:
9045 Silicone Elastomer Blend, manufactured by Dow Corning Corporation.
Note 2:
9011 Silicone Elastomer Blend, manufactured by Dow Corning Corporation Preparation Procedure Step 1: Components 1 to 4 and component 6 are mixed.
Step 2: Component 5 is added to the composition obtained in Step 1, and the mixture is mixed and dispersed.

Formulation Example 25

Shampoo

The numerical value described after each component indicates part(s) by weight (mass).

| | (Components) | |
|---|---|---|
| 1. | Purified water | remainder |
| 2. | Polyquaternium-10 | 0.3 |
| 3. | EDTA-2Na | 0.1 |
| 4. | Glycerol | 1.5 |
| 5. | Sodium laureth sulfate (27% aqueous solution) | 30.0 |
| 6. | Sodium laureth-6 carboxylate (24% aqueous solution) | 10.0 |
| 7. | Cocamidopropylbetaine, NaCl (30% aqueous solution) | 10.0 |
| 8. | Polyquaternium-7 | 0.27 |
| 9. | Preservatives | q.s. |
| 10. | Perfume | q.s. |
| 11. | Cocamido MEA | 2.0 |
| 12. | Emulsion of Silicone Compound No. 3 (Note) | 0.5 |
| 13. | Citric acid | q.s. |

Note:
O/W emulsion obtained by mixing Silicone Compound No. 3 and dimethylpolysiloxane (2 cSt) in a weight (mass) ratio of 1/9, and emulsifying the mixture so that the solid content is 30% by weight (mass).

Preparation Procedure

Step 1: Components 1 to 4 are heated, and subsequently, mixed and dissolved.
Step 2: Components 5 to 7 are added to the composition obtained in Step 1.
Step 3: The composition obtained in Step 2 is cooled, and components 8 to 12 are added thereto. Component 13 is added thereto, if necessary, to adjust the pH.

After Step 3, by further blending an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, and/or a water-soluble silicone oil such as a polyether-modified silicone or the like, or the like, the synergistic effects of respective components can be expected.

Formulation Example 26

Conditioner

The numerical value described after each component indicates part(s) by weight (mass).

| | (Components) | |
|---|---|---|
| 1. | Stearyltrimonium chloride | 1.44 |
| 2. | Cetyl alcohol | 2.4 |
| 3. | Octyl dodecanol | 0.5 |
| 4. | Cetyl ethylhexanoate | 0.6 |
| 5. | Squalane | 0.2 |
| 6. | Purified water | remainder |
| 7. | Glycerol | 2.0 |
| 8. | Preservatives | q.s. |
| 9. | Perfume | q.s. |
| 10. | Emulsion of Silicone Compound No. 3 (Note) | 3.0 |
| 11. | Citric acid | q.s. |

Note:
O/W emulsion obtained by mixing Silicone Compound No. 3 and dimethylpolysiloxane (2 cSt) in a weight (mass) ratio of 1/9, and emulsifying the mixture so that the solid content is 30% by weight (mass).

Preparation Procedure

Step 1: Components 1 to 5 are heated, and subsequently, mixed and dissolved.
Step 2: Components 6 and 7 are heated, and subsequently, mixed and dissolved.
Step 3: The composition obtained in Step 2 is added to the composition obtained in Step 1 to emulsify the mixture.
Step 4: The composition obtained in Step 3 is cooled, and components 8 to 10 are added thereto. Component 11 is added thereto, if necessary.

After Step 4, by further blending an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, and/or a water-soluble silicone oil such as a polyether-modified silicone or the like, or the like, the synergistic effects of respective components can be expected.

Formulation Example 27

Hair Treatment, Rinse-in-Type

The numerical value described after each component indicates part(s) by weight (mass).

| | (Components) | |
|---|---|---|
| 1. | Cetyl alcohol | 5.6 |
| 2. | Mineral oil | 1.0 |
| 3. | Stearyltrimonium chloride | 1.2 |
| 4. | Behentrimonium chloride | 0.64 |
| 5. | Cyclopentasiloxane | 2.0 |
| 6. | Dimethicone (2 cSt) | 1.0 |
| 7. | Dimethicone (5,000 cSt) | 1.0 |
| 8. | Phenylmethicone | 2.0 |
| 9. | Glycerol | 2.0 |
| 10. | EDTA-2Na | 0.1 |
| 11. | Purified water | remainder |
| 12. | Panthenol | 0.1 |
| 13. | Tocopherol | 0.04 |
| 14. | Lysine HCl | 0.02 |
| 15. | Glycine | 0.02 |
| 16. | Histidine | 0.02 |
| 17. | Silicone Compound No. 3 | 0.5 |
| 18. | Preservatives | q.s. |
| 19. | Perfume | q.s. |

Preparation Procedure
Step 1: Components 1 to 8 are heated, and subsequently, mixed and dissolved.
Step 2: Components 9 to 11 are heated, and subsequently, mixed and dissolved.
Step 3: The composition obtained in Step 2 is added to the composition obtained in Step 1 to emulsify the mixture.
Step 4: The composition obtained in Step 3 is cooled, and components 12 to 19 are added thereto.

In addition, in Step 1, by further adding an emulsion such as a dimethylpolysiloxane (dimethiconol) of which both terminals are capped with dimethylsilanol groups, an amino-modified silicone, an aminopolyether-co-modified silicone or the like, in addition to components 1 to 8, the synergistic effects of respective components can be expected.

Formulation Example 28

Hair Treatment, Leave-on-Type

The numerical value described after each component indicates part(s) by weight (mass).

| | (Components) | |
|---|---|---|
| 1. | Cetyl alcohol | 4.0 |
| 2. | Mineral oil | 1.0 |
| 3. | Stearyltrimonium chloride | 1.0 |
| 4. | Behentrimonium chloride | 0.2 |
| 5. | Cyclopentasiloxane | 1.2 |
| 6. | Dimethicone (2 cSt) | 0.6 |
| 7. | Dimethicone (5,000 cSt) | 0.6 |
| 8. | Phenylmethicone | 1.2 |
| 9. | Glycerol | 2.0 |
| 10. | EDTA-2Na | 0.1 |
| 11. | Purified water | remainder |
| 12. | Panthenol | 0.1 |
| 13. | Tocopherol | 0.04 |
| 14. | Lysin HCl | 0.02 |
| 15. | Glycine | 0.02 |
| 16. | Histidine | 0.02 |
| 17. | Silicone Compound No. 3 | 0.3 |
| 18. | Preservatives | q.s. |
| 19. | Perfume | q.s. |

Preparation Procedure

Step 1: Components 1 to 8 are heated, and subsequently, mixed and dissolved.

Step 2: Components 9 to 11 are heated, and subsequently, mixed and dissolved.

Step 3: The composition obtained in Step 2 is added to the composition obtained in Step 1 to emulsify the mixture.

Step 4: The composition obtained in Step 3 is cooled, and components 12 to 19 are added thereto.

In addition, in Step 1, by further adding a dimethylpolysiloxane (dimethiconol) of which both terminals are capped with dimethylsilanol groups, an amino-modified silicone, an aminopolyether-co-modified silicone or the like, in addition to components 1 to 9, the synergistic effects of respective components can be expected.

Formulation Example 29

Hair Mist

The numerical value described after each component indicates part(s) by weight (mass).

| | (Components) | |
|---|---|---|
| 1. | Purified water | remainder |
| 2. | Sorbitol | 0.6 |
| 3. | Creatine | 0.2 |
| 4. | Urea | 1.0 |
| 5. | 1,3-butylene glycol | 2.0 |
| 6. | Preservatives | q.s. |
| 7. | Ethanol | 15.0 |
| 8. | Glycereth-25 PCA isosteate | 0.5 |
| 9. | Perfume | q.s. |
| 10. | PEG/PPG-30/10 dimethicone, DPG (Note) | 1.0 |
| 11. | Silicone Compound No. 3 | 1.0 |
| 12. | Bisethoxydiglycol cyclohexanedicarboxylate | 2.0 |
| 13. | Hydroxypropyltrimonium starch chloride | 1.0 |

Note:
BY 25-338, manufactured by Dow Corning Toray Co., Ltd.

Preparation Procedure

Step 1: Components 1 to 6 are mixed and dissolved.

Step 2: Components 7 to 10 are mixed and dissolved.

Step 3: The composition obtained in Step 2 is added to the composition obtained in Step 1 to solubilize them.

Step 4: Components 11 to 13 are added to the composition obtained in Step 3, and the mixture is mixed and dissolved.

Formulation Example 30

Foam for Use on Hair

The numerical value described after each component indicates part(s) by weight (mass).

Liquid

| | (Components) | |
|---|---|---|
| 1. | Copolymer of polyvinylpyrrolidone and vinyl acetate | 5.0 |
| 2. | Diethylsulfate salt of copolymer of vinylpyrrolidone and N,N-dimethylamino-ethylmethacrylic acid | 0.5 |
| 3. | Phenyltrimethicone | 2.0 |
| 4. | Silicone Compound No. 3 | 1.0 |
| 5. | Ethanol | 12.0 |
| 6. | Preservatives | q.s. |
| 7. | Perfume | q.s. |
| 8. | Purified water | remainder |
| | Formulation | |
| 9. | Liquid | 95.0 |
| 10. | Liquid petroleum gas (LPG) | 5.0 |

Preparation Procedure

Step 1: Components 1 to 8 are mixed and dissolved.
Step 2: The composition (Liquid=Component 9) obtained in Step 1 is placed in a container (can), and a valve is loaded. Subsequently, Component 10 is placed therein.

In addition, in Step 1, a copolymer of acrylate and polytrimethylsiloxy methacrylate (such as FA 4001 CM (30% decamethylcyclopentasiloxane solution), manufactured by Dow Corning Toray Co., Ltd.) may be added as a film-forming agent, in addition to components 1 to 8.

Formulation Example 31

Hair Spray

The numerical value described after each component indicates part(s) by weight (mass).

Liquid:

| | (Components) | |
|---|---|---|
| 1. | Ethyl alcohol | remainder |
| 2. | Alkanolamine liquid of acrylic resin (active ingredient = 50%) | 7.0 |
| 3. | Cetyl alcohol | 0.1 |
| 4. | Silicone Compound No. 3 | 0.5 |
| 5. | Perfume | q.s. |
| | Formulation | |
| 6. | Liquid | 50.0 |
| 7. | Dimethyl ether | 50.0 |

Preparation Procedure

Step 1: Components 2 to 5 are added to component 1, and the mixture is mixed and dissolved.
Step 2: The composition obtained in Step 1 is filtered.
Step 3: The composition (Liquid=Component 6) obtained in Step 2 is placed in a container (can), and a valve is loaded. Subsequently, the container is charged with component 7.

Formulation Example 32

Hair Wax

The numerical value described after each component indicates part(s) by weight (mass).

| | (Components) | |
|---|---|---|
| 1. | Diethylhexyl succinate | 10.0 |
| 2. | Squalane | 1.0 |
| 3. | Shear butter | 1.0 |
| 4. | Silicone Compound No. 3 | 2.0 |
| 5. | Candelilla wax | 5.5 |
| 6. | Microcrystalline wax | 6.0 |
| 7. | Carnauba wax | 6.0 |
| 8. | Ceteth-6 | 6.0 |
| 9. | Ceteth-10 | 6.0 |
| 10. | Glyceryl stearate (SE) soap impurities | 1.5 |
| 11. | Hydroxystearic acid | 4.5 |
| 12. | Purified water | remainder |
| 13. | 1,3-butylene glycol | 3.0 |
| 14. | Sodium hydroxide | q.s. |
| 15. | PEG-90M | q.s. |
| 16. | Preservatives | q.s. |

Preparation Procedure

Step 1: Components 1 to 11 are heated, and subsequently, mixed and dissolved.
Step 2: Components 12 to 14 are heated, and subsequently, mixed and dissolved.
Step 3: The composition obtained in Step 2 is added to the composition obtained in Step 1, and the mixture is emulsified.
Step 4: Components 15 and 16 are successively added to the composition obtained in Step 3.

Formulation Example 33

Cream for Use on Hair

The numerical value described after each component indicates part(s) by weight (mass).

| | (Components) | |
|---|---|---|
| 1. | Vaseline | 4.0 |
| 2. | Cetyl ethylhexanoate | 3.0 |
| 3. | Silicone Compound No. 3 (Note) | 2.0 |
| 4. | Dimethicone (350 cSt) | 1.0 |
| 5. | PEG-40 hydrogenated castor oil | 1.0 |
| 6. | Polyacrylamide | 1.0 |
| 7. | Purified water | remainder |
| 8. | Glycerol | 3.0 |
| 9. | Hydroxyethylcellulose | 0.1 |
| 10. | Ethanol | 3.0 |
| 11. | Preservatives | q.s. |

Note:
Decamethylcyclopentasiloxane solution of Silicone Compound No. 3 (active ingredient = 10% by weight (mass)).

Preparation Procedure

Step 1: Components 1 to 5 are heated, and subsequently, mixed and dissolved.
Step 2: Components 6 to 9 are heated, and subsequently, mixed and dissolved.
Step 3: The composition obtained in Step 2 is added to the composition obtained in Step 1, and the mixture is emulsified.
Step 4: Components 10 and 11 are successively added to the composition obtained in Step 3.

In addition, in Step 1, by further adding a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, in addition to components 1 to 5, the synergistic effects of respective components can be expected.

Formulation Example 34

Lotion for Use on Hair

The numerical value described after each component indicates part(s) by weight (mass).

| | (Components) | |
|---|---|---|
| 1. | Carbomer | 0.4 |
| 2. | Hydroxyethylcellulose | 0.1 |
| 3. | PEG-6 | 1.5 |
| 4. | Purified water | remainder |
| 5. | Ethanol | 3.5 |
| 6. | PEG-40 hydrogenated castor oil | 0.5 |
| 7. | Trilaureth-4 phosphate | 0.1 |
| 8. | Cetyl ethylhexanoate | 2.0 |
| 9. | Emulsion of Silicone Compound No. 3 (Note 1) | 1.2 |
| 10. | Emulsion of dimethicone (Note 2) | 2.5 |
| 11. | Preservatives | q.s. |
| 12. | Sodium hydroxide | q.s. |

Note 1:
O/W emulsion obtained by mixing Silicone Compound No. 3 and dimethylpolysiloxane (2 cSt) in a weight (mass) ratio of 1/9, and emulsifying the mixture so that the solid content is 30% by weight (mass).
Note 2:
FZ-4150 (active ingredient = 30% by weight (mass)), manufactured by Dow Corning Toray Co., Ltd.

Preparation Procedure
Step 1: Components 1 to 4 are heated, and subsequently, mixed and dissolved.
Step 2: Components 5 to 7 are heated, and subsequently, mixed and dissolved.
Step 3: The composition obtained in Step 2 is added to the composition obtained in Step 1, and the mixture is emulsified.
Step 4: Components 8 to 12 are added to the composition obtained in Step 3.

In addition, in Step 4, by adding an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, a water-soluble silicone oil such as a polyether-modified silicone or the like, or the like, in addition to components 8 to 12, the synergistic effects of respective components can be expected.

Formulation Example 35

Oil for Use on Hair

The numerical value described after each component indicates part(s) by weight (mass).

| | (Components) | |
|---|---|---|
| 1. | Cyclopentasiloxane solution of dimethicone (Note) | remainder |
| 2. | Silicone Compound No. 3 | 3.0 |
| 3. | Dimethicone (350 cSt) | 2.0 |
| 4. | Decamethylcyclopentasiloxane | 28.0 |

Note:
BY 11-003, manufactured by Dow Corning Toray Co., Ltd.

Preparation Procedure
Step 1: Components 1 to 4 are appropriately heated, and subsequently, mixed and dissolved.

Formulation Example 36

Hair Color of Oxidation Type

The numerical value described after each component indicates part(s) by weight (mass).
First Agent

| | (Components) | |
|---|---|---|
| 1. | Steareth-2 | 3.0 |
| 2. | Steareth-21 | 2.0 |
| 3. | Stearyl PPG-15 | 5.0 |
| 4. | Cetostearyl alcohol | 4.0 |
| 5. | Behenyl alcohol | 2.0 |
| 6. | Silicone Compound No. 3 | 2.0 |
| 7. | Behenyltrimethylammonium chloride | 0.8 |
| 8. | Purified water | remainder |
| 9. | EDTA-2Na | 0.5 |
| 10. | Anhydrous sodium sulfite | 0.5 |
| 11. | Sodium ascorbate | 0.1 |
| 12. | 1,3-butylene glycol | 3.0 |
| 13. | p-phenylenediamine | 0.25 |
| 14. | p-aminophenol | 0.1 |
| 15. | m-aminophenol | 0.05 |
| 16. | Polyquaternium-39 | 0.3 |
| 17. | Ammonium hydrogen carbonate | 2.0 |
| 18. | Strong aqueous ammonia | 5.0 |

Preparation Procedure
Step 1: Components 1 to 7 are heated, and subsequently, mixed and dissolved.
Step 2: Components 8 to 15 are heated, and subsequently, mixed and dissolved.
Step 3: The composition obtained in Step 1 is added to the composition obtained in Step 2, and the mixture is emulsified.
Step 4: Components 16 to 18 are successively added to the composition obtained in Step 3.

Second Agent

| | (Components) | |
|---|---|---|
| 1. | Cetostearyl alcohol | 4.5 |
| 2. | Sodium laurylsulfate | 0.5 |
| 3. | Preservatives | q.s. |
| 4. | Etidronic acid | 0.1 |
| 5. | Disodium hydrogen phosphate | 0.3 |
| 6. | Purified water | remainder |
| 7. | Hydrogen peroxide solution (35% aqueous solution) | 17.14 |
| 8. | Phosphoric acid | q.s. |

Preparation Procedure
Step 1: Component 1 is heated and dissolved.
Step 2: Components 2 to 6 are heated, and subsequently, mixed and dissolved.
Step 3: The component obtained in Step 1 is added to the composition obtained in Step 2, and the mixture is emulsified.
Step 4: The composition obtained in Step 3 is cooled. Component 7 is added thereto and Component 8 is added thereto, if necessary.

Formulation Example 37

Hair Manicure

The numerical value described after each component indicates part(s) by weight (mass).

| | (Components) | |
|---|---|---|
| 1. | Black No. 401 | 0.4 |
| 2. | Violet No. 401 | 0.1 |
| 3. | Orange No. 205 | 0.3 |
| 4. | Benzyl alcohol | 5.0 |
| 5. | Citric acid | 0.5 |
| 6. | Hydroxyethylcellulose | 2.0 |
| 7. | Stearyltrimethylammonium chloride | 0.5 |
| 8. | PEG-40 hydrogenated castor oil | 0.5 |
| 9. | Silicone Compound No. 3 | 1.0 |
| 10. | Ethanol | 10.0 |
| 11. | Preservatives | q.s. |
| 12. | Perfume | q.s. |
| 13. | Purified water | remainder |
| 14. | Sodium citrate | q.s. |

Preparation Procedure
Step 1: Components 1 to 13 are mixed and dissolved.
Step 2: Component 14 is added to the composition obtained in Step 1, and thereby, the pH of the mixture is adjusted.

Formulation Example 38

Preparation for Permanent Waving

The numerical value described after each component indicates part(s) by weight (mass).
First Agent

| | (Components) | |
|---|---|---|
| 1. | EDTA-2Na | 0.1 |
| 2. | Etidronic acid | 0.1 |
| 3. | Preservatives | q.s. |
| 4. | Purified water | remainder |
| 5. | PEG-40 hydrogenated castor oil | 0.6 |
| 6. | Perfume | 0.3 |
| 7. | Ammonium thioglycolate (50% aqueous solution) | 13.0 |
| 8. | Strong aqueous ammonia | 1.0 |
| 9. | Monoethanolamine | 1.2 |
| 10. | Ammonium hydrogen carbonate | 2.0 |
| 11. | Emulsion of Silicone Compound No. 3 (Note) | 0.5 |
| 12. | Phosphoric acid | q.s. |

Note:
O/W emulsion obtained by mixing Silicone Compound No. 3 and dimethylpolysiloxane (2 cSt) in a weight (mass) ratio of 1/9, and emulsifying the mixture so that the solid content is 30% by weight (mass).

Preparation Procedure
Step 1: Components 1 to 4 are appropriately heated, and subsequently, mixed and dissolved.
Step 2: Components 5 and 6 are heated, and subsequently, mixed and dissolved.
Step 3: The composition obtained in Step 2 is added to the composition obtained in Step 1.
Step 4: Components 7 to 11 are successively added to a composition obtained in Step 3. Component 12 is added thereto, if necessary.
Second Agent

| | (Components) | |
|---|---|---|
| 1. | Polyquaternium-10 | 0.4 |
| 2. | EDTA-2Na | 0.1 |
| 3. | Preservatives | q.s. |
| 4. | Sodium dihydrogen phosphate | 0.05 |
| 5. | Disodium hydrogen phosphate | 0.5 |
| 6. | Purified water | remainder |

-continued

| | (Components) | |
|---|---|---|
| 7. | Sodium bromate | 8.0 |
| 8. | pH adjustor | q.s. |

Preparation Procedure
Step 1: Components 1 to 6 are appropriately heated, and subsequently, mixed and dissolved.
Step 2: Component 7 is added to a composition obtained in Step 1. Component 8 is added thereto, if necessary.

The invention claimed is:

1. A cosmetic comprising a liquid organopolysiloxane having fluidity at 25° C. and having a crosslinked three-dimensional network structure represented by the following average composition formula (1):

$$M_a D_b D^{Link}_c T_d T^{Link}_e Q_f \tag{1}$$

wherein
M represents an $R_3SiO_{1/2}$ unit;
D represents an $R_2SiO_{2/2}$ unit;
T represents an $RSiO_{3/2}$ unit;
Q represents a $SiO_{4/2}$ unit;
$D^{Link}$ represents an $RASiO_{2/2}$ unit;
$T^{Link}$ represents an $ASiO_{3/2}$ unit;
R represents a substituted or non-substituted, and linear or branched monovalent hydrocarbon group having 1 to 30 carbon atoms; and
A is a divalent linking group having a group represented by the following formula (2), (4) or (5):

$$-(CH_2)_n-SiR''_2O-(SiR''_2O)_p-SiR''_2-(CH_2)_n- \tag{2}$$

$$-C_vH_{2v}- \tag{4}$$

$$-SiR''_2O-(SiR''_2O)_p-SiR''_2- \tag{5}$$

wherein each R" independently represents a substituted or non-substituted, and linear or branched monovalent hydrocarbon group having 1 to 30 carbon atoms, and having no aliphatic unsaturated group; n is an integer ranging from 2 to 20; p is an integer ranging from 0 to 500; and v is an integer ranging from 2 to 20,
and wherein a≥0, b≥0, c≥0, d≥0, e≥0, and f≥0, with the proviso that a+b+c+d+e+f=1, and c+e ranges from 0.001 to 0.6.

2. The cosmetic according to claim 1, wherein said liquid organopolysiloxane has a loss factor, tan δ, at a shear frequency of 10 Hz, which is 1 or more.

3. The cosmetic according to claim 1, wherein said liquid organopolysiloxane is obtained by at least reacting
(a) at least one organopolysiloxane and/or at least one unsaturated aliphatic hydrocarbon, having more than one unsaturated bond on average per molecule,
(b) at least one organohydrogenpolysiloxane having more than one silicon atom-binding hydrogen atom on average per molecule, and
(c) a catalyst for a hydrosilylation reaction.

4. A cosmetic comprising a liquid organopolysiloxane having a crosslinked three-dimensional network structure, represented by the following average composition formula (1):

$$M_a D_b D^{Link}_c T_d T^{Link}_e Q_f \tag{1}$$

wherein
M represents an $R_3SiO_{1/2}$ unit;
D represents an $R_2SiO_{2/2}$ unit;
T represents an $RSiO_{3/2}$ unit;
Q represents a $SiO_{4/2}$ unit;

$D^{Link}$ represents an $RASiO_{2/2}$ unit;
$T^{Link}$ represents an $ASiO_{3/2}$ unit;
R represents a substituted or non-substituted, and linear or branched monovalent hydrocarbon group having 1 to 30 carbon atoms; and
A is a divalent linking group having a group represented by the following formula (2), (4) or (5):

$$—(CH_2)_n—SiR''_2O—(SiR''_2O)_p—SiR''_2—(CH_2)_n— \quad (2)$$

$$—C_vH_{2v}— \quad (4)$$

$$—SiR''_2O—(SiR''_2O)_p—SiR''_2— \quad (5)$$

wherein each R" independently represents a substituted or non-substituted, and linear or branched monovalent hydrocarbon group having 1 to 30 carbon atoms, and having no aliphatic unsaturated group; n is an integer ranging from 2 to 20; p is an integer ranging from 0 to 500; and v is an integer ranging from 2 to 20, and wherein a≥0, b≥0, c≥0, d≥0, e≥0, and f≥0, with the proviso that a+b+c+d+e+f=1, and c+e ranges from 0.001 to 0.6.

5. The cosmetic according to claim 1, further comprising, in addition to said (A) liquid organopolysiloxane, (B) at least one oil agent which is liquid at 25° C.

6. The cosmetic according to claim 5, comprising a uniform oil phase, and/or substantially comprising no gel particles in said oil phase.

7. The cosmetic according to claim 5, wherein said (B) oil agent has compatibility with said (A) liquid organopolysiloxane.

8. The cosmetic according to claim 5, wherein said (B) oil agent is a silicone oil.

9. The cosmetic according to claim 5, further comprising (C) at least one oil agent other than said (B) oil agent.

10. The cosmetic according to claim 1, further comprising (D) at least one surfactant.

11. The cosmetic according to claim 1, further comprising (E) at least one alcohol.

12. The cosmetic according to claim 1, further comprising (F1) at least one thickening agent and/or (F2) at least one gelling agent.

13. The cosmetic according to claim 1, further comprising (G1) at least one powder and/or (G2) at least one coloring agent.

14. The cosmetic according to claim 1, further comprising (H) at least one UV-protective component.

15. The cosmetic according to claim 1, further comprising (I) water.

16. A skin care product, a hair product, an antiperspirant product, a deodorant product, a makeup product, or a UV-protective product, which comprises the cosmetic as recited in claim 1.

17. The cosmetic according to claim 2, wherein said liquid organopolysiloxane is obtained by at least reacting
(a) at least one organopolysiloxane and/or at least one unsaturated aliphatic hydrocarbon, having more than one unsaturated bond on average per molecule,
(b) at least one organohydrogenpolysiloxane having more than one silicon atom-binding hydrogen atom on average per molecule, and
(c) a catalyst for a hydrosilylation reaction.

18. The cosmetic according to claim 4, further comprising, in addition to said (A) liquid organopolysiloxane, (B) at least one oil agent which is liquid at 25° C.

19. The cosmetic according to claim 18, comprising a uniform oil phase, and/or substantially comprising no gel particles in said oil phase.

* * * * *